US012642769B2

(12) United States Patent
Ito et al.

(10) Patent No.: US 12,642,769 B2
(45) Date of Patent: Jun. 2, 2026

(54) DELIVERY CARRIER INTO CELL

(71) Applicant: Kabusikikaisya ITO, Tokyo (JP)

(72) Inventors: Shinobu Ito, Nishitokyo (JP); Hideko Kanazawa, Tokyo (JP)

(73) Assignee: Kabusikikaisya ITO, Tokyo (JP)

( * ) Notice: Subject to any disclaimer, the term of this patent is extended or adjusted under 35 U.S.C. 154(b) by 803 days.

(21) Appl. No.: 17/787,099

(22) PCT Filed: Jul. 16, 2020

(86) PCT No.: PCT/JP2020/027737
§ 371 (c)(1),
(2) Date: Jun. 17, 2022

(87) PCT Pub. No.: WO2021/131116
PCT Pub. Date: Jul. 1, 2021

(65) Prior Publication Data

US 2023/0055665 A1 Feb. 23, 2023

(30) Foreign Application Priority Data

Dec. 23, 2019 (JP) ................................ 2019-231014

(51) Int. Cl.

| | |
|---|---|
| ***A61K 9/1273*** | (2025.01) |
| ***A61K 8/02*** | (2006.01) |
| ***A61K 8/11*** | (2006.01) |
| ***A61K 8/14*** | (2006.01) |
| ***A61K 8/67*** | (2006.01) |
| ***A61K 9/51*** | (2006.01) |
| ***A61K 31/07*** | (2006.01) |
| ***A61K 31/713*** | (2006.01) |
| ***A61K 41/00*** | (2020.01) |
| ***A61K 47/22*** | (2006.01) |
| ***A61K 47/24*** | (2006.01) |
| ***A61K 47/28*** | (2006.01) |
| ***A61K 47/44*** | (2017.01) |
| ***A61P 17/10*** | (2006.01) |
| ***A61Q 19/02*** | (2006.01) |
| ***A61Q 19/08*** | (2006.01) |
| ***C11D 3/20*** | (2006.01) |
| ***C11D 3/386*** | (2006.01) |

(52) U.S. Cl.
CPC .......... *A61K 9/1273* (2013.01); *A61K 8/0241* (2013.01); *A61K 8/11* (2013.01); *A61K 8/14* (2013.01); *A61K 8/671* (2013.01); *A61K 9/5123* (2013.01); *A61K 9/5146* (2013.01); *A61K 31/07* (2013.01); *A61K 31/713* (2013.01); *A61K 41/0042* (2013.01); *A61K 47/22* (2013.01); *A61K 47/24* (2013.01); *A61K 47/28* (2013.01); *A61K 47/44* (2013.01); *A61P 17/10* (2018.01); *A61Q 19/02* (2013.01); *A61Q 19/08* (2013.01); *C11D 3/2079* (2013.01); *C11D 3/386* (2013.01); *A61K 2800/10* (2013.01); *A61K 2800/413* (2013.01); *A61K 2800/54* (2013.01)

(58) Field of Classification Search
None
See application file for complete search history.

(56) References Cited

U.S. PATENT DOCUMENTS

| | | | |
|---|---|---|---|
| 2008/0207560 | A1 | 8/2008 | Harada et al. |
| 2017/0072070 | A1 | 3/2017 | Sada et al. |
| 2020/0032293 | A1 | 1/2020 | Kanazawa et al. |

FOREIGN PATENT DOCUMENTS

| | | | | | |
|---|---|---|---|---|---|
| CN | 102008729 | A | | 4/2011 | |
| CN | 102170853 | B | * | 7/2016 | ............... A61K 8/14 |
| JP | 2011-522616 | A | | 8/2011 | |
| JP | 2012-504620 | A | | 2/2012 | |
| JP | 2015-107986 | A | | 6/2015 | |
| JP | 2017-502997 | A | | 1/2017 | |
| JP | 2017-506681 | A | | 3/2017 | |
| WO | WO 2006/073190 | A1 | | 7/2006 | |
| WO | WO 2015/170506 | A1 | | 11/2015 | |
| WO | WO 2016/199895 | A1 | | 12/2016 | |

OTHER PUBLICATIONS

Su Jeong Song; Enzyme-responsive destabilization of stabilized plasmid-lipid nanoparticles as an efficient gene delivery http://dx.doi.org/10.1016/j.ejps.2016.05.024 (Year: 2016).*
Y. Lee; Stimuli-Responsive Liposomes for Drug Delivery doi: 10.1002/wnan.1450 (Year: 2017).*
Peng Jun Ya; Atg5 regulates late endosome and lysosome biogenesis doi: 10.1007/s11427-013-4588-8 (Year: 2014).*
Su Jeong Song; Enzyme-responsive destabilization of stabilized plasmid-lipid nanoparticles as an efficient gene delivery http://dx.doi.org/10.1016/j.ejps.2016.05.024(Year:2016) (Year: 2016).*
Y.Lee; Stimuli-Responsive Liposomes for Drug Delivery doi: 10.1002/wnan.1450 (Year:2017) (Year: 2017).*
Hiroo Takayama et al. A Novel Antioxidant, EPC-K1, Stimulates Endothelial Nitric Oxide Production and Scavenges Hydroxyl Radicals (Year: 2003).*

(Continued)

*Primary Examiner* — Robert A Wax
*Assistant Examiner* — Andre Mach
(74) *Attorney, Agent, or Firm* — Lathrop GPM LLP; Brian C. Trinque; Lisbeth Robinson

(57) ABSTRACT

[Problem to be Solved]
Provided is a delivery carrier into the cell having high antioxidant activity, intracellular absorbability, intracellular disintegration property, stability and safety, which have high delivery property of the active ingredient to cell and living tissues.
[Solution]
The delivery carrier into cells includes a vitamin derivative with co-activation of both autophagy-related genes and protease synthesis genes, a polymer molecule containing stimulatory reactivity, an emulsion stabilizer, an active ingredient, and a lipid, thereby providing a delivery carrier into cells with high delivery properties of the active ingredient to cells and living tissues.

5 Claims, 1 Drawing Sheet

(56) References Cited

OTHER PUBLICATIONS

Chinese Office Action for Chinese Application No. 202080096688.1, mailed Mar. 28, 2023, 23 pages.

Feng et al., "Pharmaceutical Polymer Materials Science", 1st Edition, published by East China University of Science and Technology Press, pp. 144-146 (2014).

Chowdhury et al., Insights into autophagosome biogenesis from structural and biochemical analyses of the ATG2A-WIPI4 complex, *PNAS USA* 115(42):E9792-E9801, Oct. 2018.

Chung et al., "Reversibly thermo-responsive alkyl-terminated poly(N-isopropylacrylamide) core-shell micellar structures", *Colloids and Surfaces B: Biointerfaces* 9:37-48, 1997.

Diao et al., "ATG14 promotes membrane tethering and fusion of autophagosomes to endolysosomes", *Nature* 520(7548):563-566, May 2015.

Filipović-Grčić et al., "Mucoadhesive chitosan-coated liposomes: characteristics and stability", *Journal of Microencapsulation* 18(1):3-12, 2001.

Heublein et al., "Alpha tocopherol transfer protein (αTTP) is expressed in endometrial carcinoma and is correlated with FIGO stage and 5-year survival", *J Cancer Res Clin Oncol* 143:773-781, 2017.

International Search Report for International Application No. PCT/JP2020/027737, mailed Sep. 15, 2020, 6 pages.

Ishigami, "The present and future of vitamin C transporter research", *The Vitamin Society of Japan, Vitamins* 88(11):555-559, 2014.

Ito et al., "Antioxidants-Carcinogenic and Chemopreventive Properties" *Advances in Cancer Research* 53:247-302, 1989.

Peng et al., "Atg5 regulates late endosome and lysosome biogenesis", *Science China Life Sciences* 57(1):59-68, Jan. 2014.

Qu et al., "Screening of α-Tocopherol Transfer Protein Sensitive Genes in Human Hepatoma Cells (HepG2)", *International Journal of Molecular Sciences* 17, 2016.

Rengel et al., "High efficiency entrapment of superoxide dismutase into mucoadhesive chitosan-coated lipsomes", *European Journal of Pharmaceutical Sciences* 15:441-448, 2002.

Savini et al., "SVCT1 and SVCT2: key proteins for vitamin C uptake", *Amino Acids* 34:347-355, 2008.

Schwartz, "The Dual Roles of Nutrients as Antioxidants and Prooxidants: Their Effects on Tumor Cell Growth", J. Nutr. 126(4 Suppl.):1221S-1227S, 1996.

Shibuya et al., "Topical Application of Trisodium Ascorbyl 6-Palmitate 2-Phosphate Actively Supplies Ascorbate to Skin Cells in an Ascorbate Transporter-Independent Manner", *Nutrients* 9, 645, 2017.

Takeuchi et al., "Enteral Absorption of Insulin in Rats from Mucoadhesive Chitosan-Coated Liposomes", *Pharmaceutical Research* 13(6):896-901, 1996.

Velikkakath et al., "Mammalian Atg2 proteins are essential for autophagosome formation and important for regulation of size and distribution of lipid droplets", *Molecular Biology of the Cell* 23(5):896-909, Mar. 2012.

Yuba et al., "Design of DDS-Application-Oriented Stimulation-Responsive Ribosome", *Farumashia* 54(1):11-15, 2018.

* cited by examiner

Figure 1)
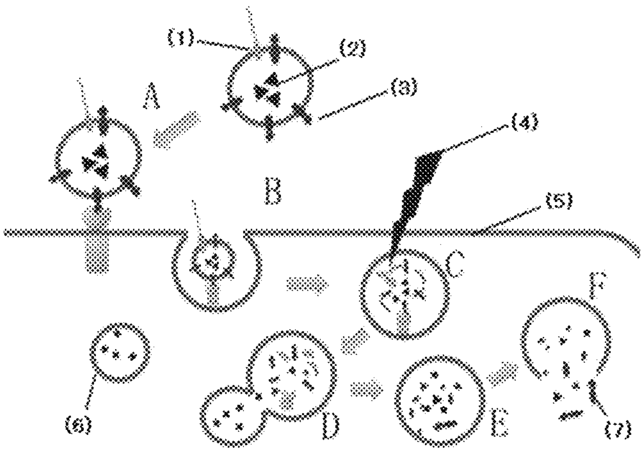
Figure 2)
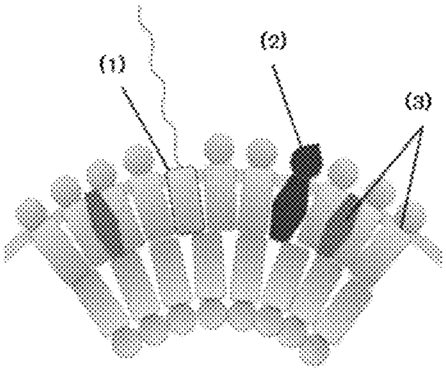
Figure 3)
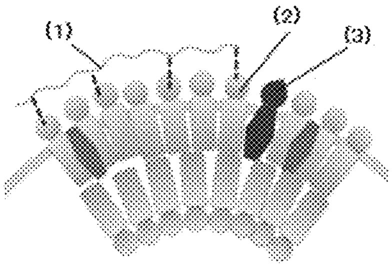

DELIVERY CARRIER INTO CELL

TECHNICAL FIELD OF THE INVENTION

The present invention relates to a Delivery carrier into cell for a stable and safe drug delivery system (DDS), comprising a stimulus-responsive polymer and a substance that promotes cell uptake and intracellular degradation mechanisms.

RELATED ART

Drug delivery systems (DDSs) are used to: 1) isolate drug action: to extract or suppress only a specific action; 2) enhance and manifest the effect: the effect is more precise and reproducible; and 3) enhance and manifest the effect. 3) Reduction of side effects: Improving quality of life and reducing the burden on patients by expanding the safety margin. In addition, it is possible to revive a compound that has been discontinued due to side effects as a drug; 4) Improved usability: this will reduce the burden on patients and healthcare professionals and solve the problem of non-compliance with medication instructions; 5) Economical: this will extend the life cycle of the product and allow for differentiation. It can also reduce medical and related costs. It is expected to improve the efficiency of research and development.

The compositions used for DDS are generally delivery carrier into the cell, and in the present invention, novel delivery carrier into the cell are disclosed. While the size of particles in delivery carrier into the cell used in conventional pharmaceuticals and cosmetics is in sub-micron to micron units, when used in delivery carrier into the cell, the particle size is much smaller. For example, when the diameter is less than 300 nm, the active ingredient can penetrate into the skin tissues through the hair follicle interstices, especially the hair follicles, which pass through the epidermis and dermis and reach the fatty layer, and the stratum corneum of the hair follicles is thin, and the fat-soluble ingredient can diffuse from the sebaceous glands to the dermis almost without passing through the skin barrier. When small particles of less than 150 nm are administered subcutaneously, the active ingredient can stay in the tissues, especially the skin tissues, because it cannot pass through the capillary wall but can enter the capillary lymphatics. In addition, particles with a diameter of less than 50 nm can pass through normal, healthy blood vessel walls and diffuse the drug into the body. Therefore, a particle size of 50 nm to 300 nm in diameter is suitable for drug retention in the target organ.

In the conventional delivery carrier into the cell, oxidative degradation is accelerated in the formulation and between the formulation and the target cell, and the active ingredient does not reach the target tissue sufficiently. In addition, the delivery carrier into the cell is not sufficiently absorbed by the cell in the target tissue due to its low cellular absorbency. In addition, there was a problem that the active ingredient was not sufficiently released because The delivery carrier into cell was not degraded within the cellular absorption even when it was absorbed. Thus, the problem to be solved by the present invention is to simultaneously solve three problems in the delivery carrier into the cell: 1) higher inhibition of oxidative degradation in and between the formulation and the target cell, and higher reach to the target tissue; 2) higher cellular absorption of the target tissue; and 3) more efficient degradation within cellular absorption. In other words, it is necessary to simultaneously enhance the three elements of 1) antioxidant activity, 2) intracellular absorption, and 3) intracellular disintegration in the Delivery carrier into cell. In addition, 4) Stability and safety are essential for the distribution of products. In the present invention, these are hereinafter referred to as the necessary elements of a delivery carrier into the cell.

Stimuli-responsive polymers are polymers that contain stimuli-responsive molecules whose microstructure changes reversibly or chemically depending on the surrounding external stimuli such as temperature, pH, ionic strength, magnetic field, electric field, light, sound waves, pressure, solvent, acceleration, and chemical species, and are used for efficient drug delivery.

Patent Documents 1 to 6 disclose systems of nanoparticles containing temperature-sensitive polymers, pH-responsive polymers, liquid crystalline polymers, and polymer gels. However, these stimuli-responsive polymers alone or in combination are effective in destroying liposomes in cells, but insufficient for the purpose of enhancing cellular absorption. In addition, when the stimuli-responsive polymers were destroyed by stimulation outside the cell, the inclusion material diffused outside the cell, making it difficult to transport the inclusion material efficiently into the target cell and reducing the significance of making liposome capsules. In other words, the use of these stimuli-responsive polymers can enhance the 3) intracellular disintegration of The delivery carrier into cell, but cannot enhance the 1) antioxidant property or 2) intracellular absorption. Therefore, there was a need for a delivery carrier into cell using a stimuli-responsive polymer with an additional system to improve the efficiency of other cell delivery applications.

The other hand, vitamins are essential nutrients in humans, and the cell of each organ and tissue have a system that catches vitamins in the blood and actively takes them into the cell according to their needs. There are known transport proteins in the blood and transport channels such as receptors and transporters on the cell membrane.

For example, the retention of ascorbic acid in skin cell is second only to that of the cerebrum, which has a high ascorbic acid concentration, and higher than that of the liver. In skin tissues, the concentration of SVCT 1 and 2 (sodium-dependent vitamin C transporter) has been confirmed in skin cell, suggesting the presence of ascorbate transporter (Non-Patent Document 1, Non-Patent Document 2). SVCT1 is predominantly found in keratinocytes, while SVCT2 is known to be found in keratinocytes, fibroblasts, and endothelial cell.

However, it has been reported that water-soluble derivatives without fat-soluble qualities, such as ascorbic acid glycerides and APPS (ascorbic acid-2-phosphate-6-palmitic acid), are absorbed by skin cells at higher concentrations than normal ascorbic acid. However, this theory cannot explain the high intracellular concentration of water-soluble ascorbic acid glycerides and ascorbic acid phosphate.

Alpha-tocopherol is present in high concentrations in the liver. Tocopherol-binding proteins are mainly known, such as its transport protein (Non-Patent Document 4), and the gene for α-tocopherol transfer protein has been screened and reported in detail (Non-Patent Document 5).

In the case of retinol, retinol-binding protein (transport protein) is a 21-kDa protein synthesized in the liver that binds and secretes vitamin A (Retinol) stored in the liver and transports it to target organs (cells).

Vitamin D-binding protein circulates in serum at high concentrations as a vitamin D transport protein, and is mainly produced by hepatocytes, which take vitamin D into cells by endocytosis mediated by megalin receptors.

Folic acid is present in high concentrations in the liver, where about half of the body's folic acid is stored. Two-thirds of folic acid in plasma is transported in protein-bound form.

Uptake of riboflavin into tissues such as the liver is mediated by special protein delivery carrier into cells at physiological concentrations, but is otherwise taken up by endocytosis.

Cobalamin (vitamin B12) is bound to transcobalamin and transported in the blood. Retinol-binding protein (RBP) is a 21-kDa protein synthesized in the liver, which binds and secretes vitamin A (Retinol) stored in the liver and transports it to target organs (cells).

Specific vitamins are known to bind to transport proteins and circulate in the blood and bind to specific receptors on the cell membranes of target tissues and are taken up in high concentrations into target cell by specific absorption channel proteins or endocytosis. Therefore, if the artificially synthesized derivatives of the specific vitamins indicated above can be maintained with sufficient blood stability, there is a very high probability of binding, in derivative form, to specific receptors on the cell membrane. However, the specific absorption channels cannot absorb these artificially synthesized vitamin derivatives because the molecular structure of each vitamin is characteristically distinguishable, but in endocytosis, we hypothesized that vitamin derivatives on the cell surface bound to these receptors may be taken up together to take up a large amount of ambient water.

The purpose of this invention is to find a special substance that enhances endocytosis activity and apply it to delivery carrier into cell s using stimuli-responsive polymers to increase the cellular uptake rate of delivery carrier into cells. Based on the above properties of vitamins, it was thought that by narrowing down the screening target to vitamin derivatives, it would be highly possible to realize a delivery carrier into cell with a high absorption rate in a shorter period of time. Vitamins themselves are extremely difficult to make present on the carrier surface due to their physical properties and stability. In addition, it was essential to screen for specific lipids and stabilizers to ensure the stable presence of stimuli-responsive polymers and special vitamin derivatives in the same delivery carrier into cell. In particular, it was thought that endocytosis activity would not increase unless the vitamin derivative was present on the carrier surface, so screening for specific lipids and stabilizers to achieve this was difficult.

Therefore, we thought that if we could somehow measure the endocytosis activity in the presence of each vitamin derivative, we would be able to determine which vitamin derivatives tend to enhance the endocytosis activity, and if we could modify the surface of the delivery carrier into the cell with vitamin derivatives that enhance the endocytosis activity, we would be able to activate the intracellular transport by endocytosis of the delivery carrier into the cell. That is, one of the purposes of this invention is to search for substances that can activate endocytosis the most among vitamin derivatives.

Recently, it was reported that glyceryl ascorbate derivatives were taken up into pigment cell at high concentrations and increased autophagy activity. In the study of the present inventors and others, the enhancement of orphagic activity with glyceryl ascorbate derivatives was observed not only in pigment cell but also in normal skin cell in general. Since autophagy is a system for the reuse of intracellularly incorporated substances, the enhancement of autophagy could explain the enhanced degradation of melanin pigment accumulated in transport alienation in pigment cell, but not the enhancement of autophagic activity in normal cell without melanin.

It was clear that the high intracellular concentrations of delivery carrier into the cell could not be explained by the fact that vitamins only improve the phospholipid permeability of cell. This is because the size of the delivery carrier into the cell is much larger than that of the modified ascorbate derivatives, and it is unlikely that large delivery carrier can be transported intracellularly unless some special system is in place.

The problem in 1) above was solved by incorporating an amphiphilic vitamin derivative with antioxidant properties into the membrane of the surface of The delivery carrier into cell. In a previous invention, the inventors succeeded in using an amphiphilic ascorbic acid derivative as a surfactant to make the membrane of The delivery carrier into cell partially or completely composed of the amphiphilic ascorbic acid derivative. However, this alone does not allow The delivery carrier into cell to be taken up into the cell at a high rate.

Furthermore, as a result of investigating the intracellular uptake mechanism of various substances in order to enhance the effect of DDS, the present inventors have come up with the idea of using endocytosis. Then, the present inventors considered that, on the contrary, modification of a substance that induces endocytosis may contribute to the uptake of carriers for cell delivery.

Furthermore, it was found that endocytosis solves the last problem, that of efficient degradation within cellular absorption. In other words, if endocytosis is used, it can take up the material around the cell membrane along with the extracellular fluid by its drinking action, which forms vesicles (endosomes) filled with the extracellular fluid. This is a general uptake mechanism that takes place in all cell, and the uptaken endosomes are subjected to degradation by lysosomes. In other words, they are efficiently degraded within cellular absorption.

The problem of efficient degradation of DD particles in cellular absorption can be solved simultaneously by screening the amphiphilic vitamin derivatives with endocytosis function and applying them to delivery carrier into the cell.

Even in fibroblasts, which have standard endocytotic activity, about 1% of the cell membrane is taken up into the cell by endocytosis per minute. In a standard mammalian cell, there are about 200 endosomes, and their total volume is about 1% of the total cell volume. The total volume of the endosomes is about 1% of the total cell volume. In terms of surface area, about 3% of the cell membrane surrounds the endosomes. In other words, in one hour, 60% of the cell membrane flows into the endosome, which has a surface area of only 3% of the cell membrane. The purpose of the present invention is to identify substances that enhance the absorption into cells by endosomes, and to modify the surface of delivery carrier into cell s using stimuli-responsive polymers to increase the rate of cellular uptake of The delivery carrier into cell s. In addition, the carrier had to be stable extracellularly and easily degraded intracellularly. High safety is another requirement. In the past, various substances were modified to stimulate the endosomal utilization of DDS, but the conventional techniques did not provide sufficient endosomal activity or stability outside the cell, and as a result, high intracellular uptake rates could not be achieved. In addition, those with high extracellular stability were not degraded intracellularly, resulting in the inability to sufficiently release the active ingredients.

In the cell, endosomes fuse with lysosomes. Lysosomes are eukaryotic biomembrane-enclosed structures with hydrolytic enzymes inside, and biomacromolecules taken into the membrane are hydrolyzed by these enzymes. After being fused to the endosome containing the object to be degraded, it is called a secondary lysosome or phagolysosome. One of the secondary lysosomes is derived from this endocytosis. The primary lysosome fuses with the phagosome and the pinosome, a structure comprising a single biological membrane containing more microscopic molecules near the cell membrane, to form the phagolysosome, which degrades the foreign substance. The hydrolytic enzymes contained in the lysosome work efficiently under acidic conditions, and the hydrogen ion index inside the lysosome is maintained at an acidic pH of about 5 by the action of the proton pump. In other words, the method of incorporating a Delivery carrier into cell that activates endocytosis can also promote the degradation of the carrier in the cell and enhance the activity of the active ingredient in the cell.

The endosomal carrier molecules are degraded by lysosomes and some of them accumulate in the cells. This is thought to activate autophagy. In other words, when endosomes are activated by endocytosis, not only the endosomal system but also autophagy is activated, and the biosynthesis of related proteins in the autophagosomal system is also activated. In other words, one of the purposes of this invention is to detect the markers responsible for the activity of endosomes and autophagosomes, to search for substances that activate endosomes and autophagosomes using these markers, and finally to modify the surface of the Delivery carrier into cell.

Among the four necessary elements of the Delivery carrier into cell, which are 1) antioxidant activity, 2) intracellular absorption, 3) intracellular disintegration, and 4) stability and safety, endocytosis, which is related to endosomes, is related to 2) intracellular absorption, and autophagy, which is mediated by autophagosomes, is related to 3) intracellular disintegration.

Lysosomes contain digestive enzymes and degrade proteins and other substances in cell. Autophagy is a mechanism of degradation of proteins in the cytoplasm, which is similar to endocytosis. The lipid membrane elongates and surrounds the part of the cytoplasm that contains the degrading substance. Next, the lipid membrane separates into the inner and outer membranes to form an autophagosome comprising a lipid bilayer. The lysosome containing digestive enzymes fuses with the outer membrane of the autophagosome, and the digestive enzymes of the lysosome flow between the outer membrane and the inner membrane, and then only the inner membrane is degraded, and the degraded substance and digestive enzymes are mixed and the degradation process begins.

Although many factors are required for autophagosome formation, they can be classified into the following five functional groups: 1) the binding and reaction system of the ubiquitin-like factor Atg8 (Atg8 system): Atg8, Atg4, Atg7, and Atg3; 2) the binding and reaction system of the ubiquitin-like factor Atg12 (Atg12 system): Atg12, Atg7, and Atg10, Atg5, Atg16; 3) Atg1 protein kinase complex: Atg1, Atg13, Atg17, Atg29; 4) Vps34 PI3 kinase complex: Vps34, Vps15, Atg14, Atg6; 5) Atg9 and Atg2-Atg18 complex: Atg2, Atg18, Atg9.

The present inventors focused on Atg5 as an activation marker for endosomes and autophagosomes. This is because Atg5 is required not only for autophagosome formation but also for endosome and lysosome biosynthesis (Non-Patent Document 6).

This invention involves the screening of vitamin derivatives for substances that have a stimulatory effect on the synthesis of one or more of the proteins necessary for the biosynthesis of autophagosomes, endosomes, and lysosomes. Vitamin derivatives were chosen for three reasons: 1) they are more stable than vitamins and can be made amphiphilic in their physical properties, 2) they are extremely safe, and 3) vitamin derivatives can be degraded in cells and transformed into vitamins to exert effective physiological effects in cells.

The present inventors examined the relationship between the type of vitamin derivatives modified in the emulsion composition and their uptake into the cell by detecting the m-RNAs responsible for the synthesis of Atg5 by microarrays and comparing them with the additive-free control.

The results showed that when certain vitamin derivatives were mixed with the emulsion composition, the cellular uptake of the carriers for cell delivery was increased, and at the same time, the ATG5 value was predominantly increased compared to the control. In addition to ATG5, the m-RNA levels of ATG2, 3, 4, 7, 10, 101, 12, 13, 14, and 15 were also increased simultaneously.

Therefore, the inventors set ATG2, 3, 4, 5, 7, 10, 101, 12, 13, 14, and 15 as markers of endocytosis and autophagy activity, which are also related to endosomes but are reported to be mainly related to autophagosome formation, and completed the delivery carrier into the cell of the invention by modifying various vitamin derivatives and quantifying the activation of the synthesis of this protein by m-RNA microarrays. Furthermore, we found that these substances can provide delivery carrier into the cell with good cell absorption by modifying them.

The high ATG activity of water-soluble derivatives such as glyceryl octyl ascorbate, which could not be explained only by the permeability of cellular phospholipid membranes, suggested that endocytosis was activated and consequently, it had a high intracellular transport capacity. Furthermore, endocytosed substances are known to potentiate autophagic activity, which may explain why glyceryl octyl ascorbate potentiates autophagic activity in non-melanin-producing cell.

For example, ATG2 is required for the expansion of the autophagosome precursor membrane phagophore (Non-Patent Document 7), and the Atg2 protein functions in the formation of autophagosomes and in the regulation of the morphology and dispersion of lipid droplets such as lysomes (Non-Patent Document 8).

Autophagy begins by forming a double membrane autophagosome and ends when the autophagosome fuses with the lysosome. The oligomer ATG14 on autophagosomes binds to a special complex and promotes autophagosomal and endolysosomal fusion (Non-Patent Document 9).

As a result, it was found that the following carriers for cell delivery of the present invention could solve all the problems of the four essential elements, and the present invention was completed.

When the endocytosis-promoting substance in the delivery carrier into the cell of the present invention is an amphiphilic antioxidant vitamin derivative, it stabilizes the substance in the delivery carrier into the cell that is unstable against oxidation and achieves high cellular absorbability. In addition, the affinity with the vitamin-binding protein of the cell is strengthened, and it is easier to be taken up by the cell and more preferable.

Furthermore, if the endocytosis-promoting substance is an amphiphilic antioxidant vitamin derivative, it is preferable because it is easily anchored to the surface of the emulsion film by its surfactant power.

The presence of this amphiphilic antioxidant vitamin induction can be attributed to the emulsion film itself, or it can exist between the emulsion films to form an antioxidant barrier, which effectively prevents the invasion of external reactive oxygen species from reaching the central core where the active ingredients are present. Thus, it is clearly different from the case where antioxidants are present in the central core where the active ingredient is present or in the solvent where the DDS particles are suspended, as in a normal DDS capsule.

It has already been discovered by the inventors and others in 2007 that by selecting specific amphiphilic antioxidant vitamin derivatives for the present invention, it is possible to form delivery carrier into cell s with useful lamellar structures by using them alone or in complex, and that substances conjugated with these antioxidant membranes are protected from reactive oxygen species and maintain their stability even when they are active ingredients that are easily oxidized. However, this is not enough. However, this alone was not enough to achieve a sufficient cell delivery rate.

Amphiphilic antioxidants are derivatives of antioxidants such as ascorbic acid and tocopherols, which are water-soluble and fat-soluble, respectively. Because the active center is modified, the antioxidant activity is also reduced. The reaction rate with active oxygen is intentionally reduced. It is known that the decrease in the reaction rate of amphiphilic antioxidant vitamin derivatives with ROS also decreases the generation of pro-oxidants.

The mere addition of amphiphilic antioxidant vitamins in the conventional way does not provide efficient protection against reactive oxygen species (ROS) in active ingredients that are easily oxidized. The effect of the invention can be efficiently demonstrated only by the presence of amphiphilic antioxidant vitamins locally in the emulsion membrane itself or between the emulsion membranes of The delivery carrier into cell s. This is because the presence of a barrier of antioxidant vitamin derivatives in the form of a membrane around the central core is more effective in scavenging active oxygen from the outside than the presence of antioxidant vitamin derivatives in the central core where the active ingredient is located. Furthermore, if the membrane is multilayered by adopting a lamellar structure, multiple layers of antioxidant barriers are formed, and the structure that protects the central core, where the active ingredients exist, is strengthened. Therefore, monolamellar lipid bilayers and more multilayered lamellar structures are more effective for emulsified films, and in the present invention, a lamellar structure with three or more layers is most suitable for demonstrating the effectiveness of the present invention.

Furthermore, the amphiphilic antioxidant vitamin derivative of the present invention is preferably present at least 10% between the emulsions of the multilayer (LAMELLAR) structure of the present invention and the emulsions. This method can easily determine the concentration of amphiphilic antioxidant vitamins in the liposomal and non-liposomal fractions at the time of gel filtration, in both water and non-water content, by HPLC.

In order to prevent oxidation of active ingredients conjugated to delivery carrier into cell s and protect them from reactive oxygen species, strong antioxidants such as conventional butylated hydroxyanisole (BHA) and antioxidant vitamins such as ascorbic acid and tocopherols have been added together with active ingredients and delivery carrier into cell s. However, the addition of these non-amphiphilic antioxidants alone does not exert sufficient antioxidant power, and it is extremely difficult to maintain the conjugated active ingredients for a long period of time without inactivation. This is because non-amphiphilic antioxidants such as ascorbic acid and tocopherol have high reactivity with active oxygen and are quickly oxidized to form pro-oxidants such as BHA radicals, tocopherol radicals, and ascorbic acid radicals, and the antioxidant power is not sustained for a long time. In addition, these active ingredients were made to stay in the central core of The delivery carrier into cell in order to coexist with the active ingredients in anticipation of their effects, so the conjugated membrane surrounding the central core itself could not be protected from reactive oxygen species by these antioxidants.

BHA, an artificially synthesized powerful antioxidant, has been confirmed to be carcinogenic, and in terms of safety, its product value decreases when it is added to foods and cosmetics. It has been reported in the literature that not only BHA but also many antioxidants cause carcinogenicity and toxicity by their pro-oxidant effect (Non-Patent Document 10).

In addition, carotenoids, tocopherols, or ascorbic acid also exhibit oxidation-promoting properties depending on the redox potential of individual molecules and the inorganic chemical properties of cell, and it has been pointed out that these antioxidant vitamins can become pro-oxidants and these reactive oxygen metabolites can damage DNA and cell membranes (Non-Patent Document 11).

In addition, although the size of the delivery carrier into the cell is reduced to increase cell permeability, the smaller the size of the delivery carrier into the cell, the higher the probability of pro-oxidant generation and the easier it is to be degraded because the establishment of association between the cell membrane of the delivery carrier into the cell and reactive oxygen per unit active ingredient increases in proportion to the size of the delivery carrier into the cell.

In addition, while the average diameter of The delivery carrier into cell is 30 μm or less, if the carrier is reduced to 300 nm or less, which is required in recent years to improve skin permeability, its surface area increases 30 times, making it 30 times more vulnerable to the attack of reactive oxygen species. In other words, the more small delivery carrier into the cell are made, the more likely the active ingredient is to degrade, the more likely it is to lose its effectiveness and the greater the problem of increased pro-oxidant toxicity of the antioxidant.

The purpose of our invention was to provide micro-nanocapsules with a stable and safe antioxidant like a coating and to improve the oxidation stability of the active ingredients of the emulsion film a delivery carrier and the central core at the same time. By using amphiphilic antioxidants, which have lower antioxidant activity than conventional antioxidants, it was found for the first time that both the emulsified film and the active ingredients of the central core could be stably protected from reactive oxygen species in micro-nanocapsules simultaneously. In addition, the ratio of amphiphilic antioxidants in the emulsion of a delivery carrier was increased by making the emulsion film into a lamellar structure, i.e., a multi-layered capsule, and it was possible to block the passage of reactive oxygen species more efficiently.

PRIOR ART DOCUMENT

[Patent Document]

[Patent Document 1] Published Japanese Translation No. 2011-522616 of the PCT International Publication

[Patent Document 2] Japanese Unexamined Patent Application, First Publication No. 2015-107986

[Patent Document 3] Republication of WO 2016/199895 A1

[Patent Document 4] Republication of WO 2015/170506 A1

[Patent Document 5] Published Japanese Translation No. 2017-506681 of the PCT International Publication

[Patent Document 6] Published Japanese Translation No. 2017-502997 of the PCT International Publication

[Patent Document 7] Republication of WO 2016/199895 A1

[Non-Patent Document]

[Non-Patent Document 1] Savinil, et al., Amino Acids 34, 347-355(2008)

[Non-Patent Document 2] Ishigami, et al., Vitamin (Japan) 88(11), 555-559(2014)

[Non-Patent Document 3] Shibuya, S., et al., Nutrients 2017, 9,645; doi:10.3390/nu9070645

[Non-Patent Document 4] Heublein S, et al., J Cancer Res Clin Oncol. 2017/5; 143(5):773-781.

[Non-Patent Document 5] Qu Y H, et al., Int J Mol Sci 2016 June 27; 17(7):1016.

[Non-Patent Document 6] Peng J, et al., Sci China Life Sci. 2014 January; 57(1):59-68.

[Non-Patent Document 7] Chowdhury S, et al., Proc Natl Acad Sci USA, 2018, 16; 115 (42): E9792-E9801.

[Non-Patent Document 8] Velikkakath A K, et al., Mol Biol Cell, 2012 March; 23 (5): 896-909.

[Non-Patent Document 9] Diao J, et al., Nature. 2015 April 23; 520 (7548):563-6.

[Non-Patent Document 10] Ito N, Hirose M. Adv Cancer Res. 1989; 53:247-302.

[Non-Patent Document 11] Schwartz J L. J Nutr. 1996 April; 126 (4 Suppl): 1221S-7S.

[Non-Patent Document 12]J. E. Chung M. et al., Volume 9, Issues 1-2, 1997, 37-48

[Non-Patent Document 13] Galovie Renge 1R, et al., Eur J Pharm Sci. 2002 June; 15(5):441-8.

[Non-Patent Document 14] Filipovie-Grcie J, et al., J Microencapsul. 2001 January-February; 18(1):3-12.

[Non-Patent Document 15] Takeuchi H, et al., Pharm Res. 1996 June; 13(6):896-901.

DISCLOSURE OF THE INVENTION

Problems to be Solved by the Invention

To summarize the problem to be solved by the invention, it is to provide a carrier particle for cell delivery that simultaneously enhances the four necessary elements of a delivery carrier into cell: 1) antioxidant activity, 2) intracellular absorption, 3) intracellular disintegration, and 4) enhanced stability and safety.

Means to Solving the Problem

To summarize the means to solve the above problems, 1) the antioxidant property required for The delivery carrier into cell can be solved by placing an excellent antioxidant vitamin derivative on the surface of The delivery carrier into cell, and 2) the intracellular absorption property can be enhanced by adding a vitamin derivative that induces endocytosis to the emulsion composition. 2) Intracellular absorption can be enhanced by blending a vitamin derivative that induces endocytosis into the emulsion composition, and by placing a stimuli-responsive polymer on the surface of The delivery carrier into cell, The delivery carrier into cell can be disintegrated in or near the target cells. In addition, by limiting the blended vitamin derivatives to those that enhance intracellular autophagy and lysosomal activity, 3) intracellular disintegration is induced, and the stable amphiphilic vitamin derivative components inside The delivery carrier into cell are decomposed and converted into vitamins that can be used by the cell.

The aspects of the present invention are as follows:

1. A Delivery carrier into cell comprising a mixture of one or more substances selected from each of the following three groups: substances that simultaneously activate autophagy-related genes and cathepsin synthesis genes, stimuli-responsive polymer-containing molecules, and lipids.
2. The delivery carrier into cell of aspect 1, comprising a mixture of one or more substances selected from each of the following four groups: simultaneous activators of autophagy-related genes and cathepsin synthesis genes, stimuli-responsive polymer-containing molecules, emulsification stabilizers, and lipids.
3. The delivery carrier into cell of aspect 1, comprising a mixture of one or more substances selected from each of the following five groups: a substance that simultaneously activates autophagy-related genes and cathepsin synthesis genes, a molecule containing a stimuli-responsive polymer, an emulsification stabilizer, an active ingredient, and a lipid, and in which the active ingredient is encapsulated in the Delivery carrier into cell. The delivery carrier into cell of claim 1.
4. The delivery carrier into cell of aspect 1, wherein some or all of the lipid is a lipid with 8 or more consecutive hydrocarbon chains.
5. The delivery carrier into cell of aspect 1, wherein some or all of the lipid is a surfactant.
6. The delivery carrier into cell of aspect 1, wherein some or all of the lipid is a surfactant that forms lamellae.
7. The delivery carrier into cell of aspect 1, wherein The delivery carrier into cell has either a monolamellar structure or a polylamellar structure.
8. The delivery carrier into cell of aspect 1, wherein some or all of the lipids are selected from either cationic lipids or anionic lipids or anionic lipids.
9. The delivery carrier into cell of aspect 1, wherein the carrier exists in the form of fine particles dispersed in an aqueous solvent.
10. delivery carrier into cell of aspect 1, wherein the particles dispersed in an aqueous solvent are nanoparticles with an average particle size in the range of 1 nm to 300 nm.
11. The delivery carrier into cell of aspect 1, wherein The delivery carrier into cell is a delivery carrier into cell for a drug delivery system.
12. The delivery carrier into cell of aspect 1, wherein the autophagy-related gene and the cathepsin synthesis gene are genes registered with the Human Genome Nomenclature Committee of the Organization for Human Genetic Analysis selected from Table 1 below.

TABLE 1

| Autophagy-related gene |
| --- |
| ULKI, ULK2, ATG2A, ATG2B, ATG3, ATG4A, ATG4B, ATG4C, ATG4D, ATG5, BECN1, ATG7, GABARAP, GABARAPL1, GABARAPL2, MAP1LC3A, MAP1LC3B, MAP1LC3B2, MAP1LC3C, ATG9A, ATG9B, ATG10, ATG12, ATG13, ATG14, ATG16L1, ATG16L2, RB1CC1, WIPI1, WIPE, SNX30, SNX4, ATG101,AMBRA1 |
| Cathepsin synthesis gene |
| CTSA, CTSB, CTSC, CTSD, CTSD, CTSE, CTSF, CTSG, CTSH, CTSK, CTSL, CTSLP6, CTSO, CTSS, CTSV, CTSW, CTSZ. |

13. The delivery carrier into cell of aspect 1, wherein one or more of the substance that simultaneously activates autophagy-related genes and cathepsin synthesis genes and the stimuli-responsive polymer-containing molecule form part of a membrane molecule composed predominantly of lipids.

14. The delivery carrier into cell of aspect 1, wherein the stimuli-responsive polymer-containing molecule is ionically bound to the lipid.

15. The delivery carrier into cell of aspect 1, wherein the stimuli-responsive polymer-containing molecule contains a stimuli-responsive molecule that is responsive to one or more of the following three conditions: temperature, pH, and light.

16. The delivery carrier into cell of aspect 1, wherein the simultaneous activator of the autophagy-related gene and the cathepsin synthesis gene is selected from vitamin derivatives.

17. The delivery carrier into cell of aspect 1, wherein the simultaneous activator of the autophagy-related gene and the cathepsin synthesis gene comprises one or more substances selected from the vitamin derivative groups in Table 2 below.

TABLE 2

| |
| --- |
| Na (ascorbyl/cholesteryl) phosphate, K (ascorbyl/tocopheryl) phosphate, (linoleic acid/oleic acid) tocopherol, ethyl 2,4-dicarboethoxypantothenate, 3-O-ethylascorbic acid, 3-O-Cetyl ascorbic acid, 3-ascorbyl carbonyl dipeptide-17, ascorbyl ethyl, ascorbyl methyl silanol pectin, ascorbyl glyceryl diester tocopherol, ascorbate glucoside, ascorbate diester tocopherol, ascorbate tetrahexyldecyl, ascorbate polypeptide, ascorbyl methyl ascorbate, Caprylyl 2-glyceryl ascorbic acid, caprylyl 3-glyceryl ascorbic acid, tocopherol succinate, diethyl ascorbic acid, dioleyl Tocopheryl methylsilanol, pyridoxine dicaprylate, ethyl dicarboethoxypantothenate, pyridoxine dipalmitate, ascorbyl stearate, thioctic acid stearate, thioctic acid palmitate, thioctic acid margallate, tetrahexyldecanoic acid ascorbyl, tetrabutyric acid riboflavin, tocopheryl Oxypropyltrisiloxane, tocopheryl glucoside, sodium tocopheryl phosphate, tocofersolane, pyridoxine trishexyldecanoate, tocopherol nicotinate, retinol palmitate, ascorbyl propyl hyaluronate, hydroxydecyl ubiquinone, retinol propionate, ascorbyl tocopheryl maleate, Laurimino dipropionate tocopheryl phosphate 2Na, linoleate tocopherol, linoleate Tinol, Tocopherol phosphate 2Na, Tocopheryl retinoate, Retinyl retinoate, Tocopherol acetate, Retinol acetate |

18. The delivery carrier into the cell of aspect 1, wherein a lipid is one or more substances selected from the group of substances in Table 3 below.

TABLE 3

| |
| --- |
| Alkane sulfonic acid, Triethanolamine alkyl (12-15) sulfate, Alkyl glucoside, Aluminum isostearate, Glyceryl isostearate, Sorbitan isostearate, Polyethylene glycol isostearate Sorbitan, Polyethylene glycol isostearate, Polyoxyethylene (20) sorbitan isostearate, Isostearoyl lactic acid, Diglyceryl isopalmitate, Undecyl-N-carboxymethyl imimidazole N-Carboxymethyl Imidazolium Betaine, Undecyl Hydroxyethyl Imidazolium Betaine, Zinc Undecylate, Ethylene Glycol Fatty Acid Esters, Glyceryl Erucate, Oleyl Dimethylamine Oxide, Oleyl Sulfate Glyceryl Erucate, Oleyl Dimethylamine Oxide, Oleyl Sulfate, Oleyl Sulfate Triethanolamine, Oleic Acid, Glyceryl Oleate, Oleoyl Sarcosine, Oleoyl Methyl Taurine, Ganglioside, Cholic Acid, Surfactin and its Salts, Glyceryl Safflower Oil Fatty Acid, Saponin, Glyceryl Diarachinate, Diisostearate Glyceryl diisostearate, Poly(2-10) glyceryl diisostearate, Ethylene polyoxypropylene decyl tetradecyl ether, Ethylene glycol dioctanoate, Dioctylamine, Dioleate Ethylene glycol dioleate, Polyethylene glycol dioleate, Ethylene glycol distearate, Glyceryl distearate, Diethylene glycol distearate, Sorbitan distearate, Poly(6-10) glyceryl distearate, Poly(6-10) glyceryl distearate Poly(6-1-0)glyceryl distearate, Polyethylene glycol) distearate, Polyethylene glycol) dipalmitate (150), Dihydroxyethyl lauryl dimethylamine oxide, Aluminum dimyristate Aluminum acid, Dimethylstearylamine, Sucrose fatty acid ester, Diethylene glycol dilaurate, Polyethylene glycol dilaurate, Polyethylene glycol dicinoleate, Stearyl dihydroxyethyl betaine, Betaine stearyldimethylaminoacetate, Stearyl dimethylamine oxide, Stearyl dimethyl betaine, Stearyl trimethyl ammonium saccharin, Stearyl sulfate, Stearic acid, Stearic acid diethylaminoethylamide, Diethylene glycol stearate, Triethanolamine stearate, Stearoyl Acylglutamic Acid, Stearoyl Methyl Taurine, Stearoyl Lactic Acid, Spicrisporic Acid, Sphingomyelin, Sphingophospholipids, Dioctyl Sulfosuccinate, Lauryl Sulfosuccinate, Sorbitan Sesquiisostearate, Glyceryl Sesquioleate, Glyceryl sesquioleate, Diglyceryl sesquioleate, Sorbitan sesquioleate, Sorbitan sesquistearate, Cetyl trimethyl ammonium saccharin, Cetyl phosphate, Diethanolamine cetyl phosphate, Cetyl sulfate, Sophorolipid, Deoxycholic acid, Poly(10) glyceryl decaeoleate Poly(10) glyceryl trioleate, Decaglyceryl decastaearate, Poly(2) glyceryl tetraisostearate, Tetradecasulfonic acid, Diglyceryl triisostearate, Sorbitan trioleate, Poly(10) glyceryl trioleate, Polyoxyethylene(20) sorbitan trioleate, Sorbitan tristearate, Poly(10) glyceryl tristearate Poly (10) glyceryl trioleate, Polyoxyethylene (150) sorbitan tristearate, Polyoxyethylene (2) sorbitan tristearate (0) sorbitan, polyoxyethylene tristearate sorbitan, trilaurylamine, trehalose lipid, palm oil fatty acid acyl-N-carboxyethyl-N-hydroxyethyl ethylenediamine, palm oil fatty acid amidopropyl betaine, palmitic acid, isopropanolamine palmitate, polyethylene glycol palmitate, Palmitoyl methyl taurine, Castor oil fatty acid, Poly(10) glyceryl heptastearate, Glyceryl behenate, Poly(6-10) glyceryl pentaoleate Glyceryl pentaoleate, Decaglyceryl pentastearate, Polyoxyethylene (1) alkyl (11,13,1) ether sulfate, Polyoxyethylene (1) alkyl (11,13,1) ether sulfate 5) ether sulfate, |

TABLE 3-continued

| |
|---|
| polyoxyethylene (1) alkyl (11,13,15) ether sulfate Polyoxyethylene (1) alkyl (11,13,15) ether sulfate, Polyoxyethylene (l) polyoxypropylene (1,2,4,8) cetyl ether (10) alkyl (12,13) ether, polyoxyethylene (10) alkyl (12,13) ether Polyoxyethylene (10) alkyl (12,13) ether phosphate, Polyoxyethylene (10) polyoxypropylene (1,2,4,8) cetyl ether Polyoxyethylene (10) alkyl (12,13) ether phosphoric acid, Polyoxyethylene (10) polyoxypropylene (1,2,4,8) cetyl ether, Polyoxyethylene (10) hardened castor oil, Polyoxyethylene (2) Polyoxyethylene (2) alkyl (12,13) ether sulfate, Polyoxyethylene (2) lauryl ether sulfate, Polyoxyethylene (2,10, 20) isostearyl ether sulfate Polyoxyethylene (20) polyoxypropylene (1,2,4,8) cetyl ether, Polyoxyethylene (2,0) coconut oil fatty acid sorbitan Polyoxyethylene (20) polyoxypropylene (1,2,4,8) cetyl ether, polyoxyethylene (2) coconut oil fatty acid sorbitan, polyoxyethylene (20) hardened castor oil, polyoxyethylene (3) Polyoxyethylene (3) alkyl (11-15) ether sulfate, Polyoxyethylene (3) polyoxypropylene (34) stearyl ether, Polyoxyethylene (3) myristyl ether sulfate Polyoxyethylene (3) alkyl (11-15) ether sulfate, Polyoxyethylene (3) polyoxypropylene (34) stearyl ether, Polyoxyethylene (3) myristyl ether sulfate 4) ether, Polyoxyethylene (34) Polyoxypropylene (23) Stearyl Ether, Polyoxyethylene (4) Polyoxypropylene (30) stearyl ether, Polyoxyethylene (40) hardened castor oil, Polyoxyethylene (5) polyoxypropylene (Polyoxyethylene (5) Polyoxypropylene (1,2,4,8) Cetyl Ether, Polyoxyethylene (50) Castor Oil, Polyoxyethylene (60) Castor Oil Polyoxyethylene (5) polyoxypropylene (1,2,4,8) cetyl ether, polyoxyethylene (50) hardened castor oil, polyoxyethylene (60) hardened castor oil Polyoxyethylene alkyl ether phosphate, Polyoxyethylene alkyl phenyl ether phosphate, Polyoxyethylene alkyl phenyl ether phosphate triethanolamine, Polyoxyethylene isocetyl ether, Polyoxyethylene octyl ether phosphate, Polyoxyethylene octyldodecyl ether, Polyoxyethylene octyl phenyl ether, Polyoxyethylene oleyl ether, Polyoxyethylene oleyl ether phosphoric acid, Polyoxyethylene oleyl ether phosphoric acid diethanolamine, etc. Polyoxyethylene oleyl cetyl ether, Polyoxyethylene denonylphenyl ether, Polyoxyethylene stearyl ether, Polyoxyethylene stearyl ether phosphoric acid, Polyoxyethylene cetyl ether, Polyoxyethylene cetyl ether phosphoric acid, Polyoxyethylene cetostearyl ether, Polyoxyethylene tridecyl ether, Polyoxyethylene tridecyl ether acetate, Polyoxyethylene nonylphenyl ether, Polyoxyethylene castor oil, Polyoxyethylene behenyl ether, Polyoxyethylene Polyoxyethylene polyoxypropylene cetyl ether, polyoxyethylene polyoxypropylene lauryl ether, polyoxyethylene myristyl ether, polyoxyethylene coconut oil alkyl dimethylamine oxide, etc. Polyoxyethylene lauryl ether phosphate, Polyoxyethylene lauryl ether phosphate triethanolamine, Polyoxyethylene lauryl ether acetate, Polyoxyethylene lauryl ether sulfate, Polyoxyethylene lauryl ether sulfate triethanolamine, Mannosylerythritol Lipid, Myristyl Sulfate, Myristic Acid, Isopropanolamine Myristate, Glyceryl Myristate, Polyethylene Glycol Myristate, Myristoyl Acylglutamic Acid, Myristoyl Sarcosine, Myristoyl Methylalanine, Sorbitan monoisostearate, polyglyceryl monoisostearate, glyceryl monomyristate, sorbitan monooleate, polyglyceryl monooleate, polyethylene glycol monooleate, ethylene glycol monostearate, sorbitan monostearate Sorbitan monostearate, Polyglyceryl monostearate, Polyethylene glycol monostearate, Polyoxyethylene sorbitan monostearate, Sorbitan monopalmitate, Polyoxyethylene sorbitan monopalmitate, Glyceryl monohidroxystearate, Polyglyceryl monomyristate Polyglyceryl monomyristate, Sorbitan monolaurate, Polyethylene glycol monolaurate, Polyoxyethylene sorbitan monolaurate, Glyceryl monolanoline fatty acid, Glyceride monofatty acid, Betaine coconut oil alkyl dimethylaminoacetate, Coconut oil alkyl dimethylamine oxide, Coconut oil alkyl magnesium sulfate triethanolamine, Coconut oil fatty acid, Coconut oil fatty acid and cured beef fatty acid acylglutamic acid, Coconut oil fatty acid acyl-N-carboxyethyl-N-hydroxyethyl ethylenediamine N-Hydroxyethylenediamine II, Coconut oil fatty acid acyl-N-carboxyethoxyethyl-N Coconut oil fatty acid acyl-N-carboxyethyl ethylenediamine 2, Coconut oil fatty acid ethylester sulfonic acid, Coconut oil fatty acid sucrose ester, Coconut oil fatty acid sorbitan, Coconut oil fatty acid triethanolamine, Lauryl aminodipropionate, Laurylaminopropionate, Laurylaminopropionate Triethanolamine, Lauryl Dimethylamine Oxide, Lauryl Hydroxysulfobetaine, Lauryl Phosphate, Lauryl Sulfate, Ammonium Lauryl Sulfate, Diethanolamine Lauryl Sulfate, Triethanolamine Lauryl Sulfate Diethanolamine Lauryl Sulfate, Diethanolamine Lauryl Sulfate, Triethanolamine Lauryl Sulfate, Magnesium Lauryl Sulfate, Monoethanolamine Lauryl Sulfate, Lauric Acid, Betaine Acetate Amidopropyl Laurate, Glycerin Laurate, Diethylene Glycol Laurate, Triethanolamine Laurate, Lauroyl Acylglutamic Acid, Triethanol lauroyl acylglutamic acid, Triethanolamine lauroyl methylalanine, Rhamnolipid, Amidopropyl betaine ricinoleate, Glyceryl ricinoleate, Glyceryl linoleate, Alkyl(16,18)trimethylammonium chloride Alkyl (16,18) trimethylammonium chloride, Alkyl (20-22) trimethylammonium chloride, Alkyl (28) trimethylammonium chloride Alkyl (16,18) trimethylammonium chloride, Alkyl (20-22) trimethylammonium chloride, Alkyl (28) trimethylammonium chloride, Isostearyl lauryl dimethylammonium chloride, Di (polyoxyethylene) oleyl methylammonium chloride (2EO) (2EO), Dialkyl (12-15) dimethylammonium chloride, Dialkyl (12-1-8) dimethylammonium chloride, Alkyl (28) trimethylammonium chloride, Isostearyl lauryl dimethylammonium chloride (12-15) dimethylammonium chloride, dialkyl (12-1-8) dimethylammonium chloride, dialkyl (14-18) dimethylammonium chloride, dicocoyl dimethylammonium chloride, diallyl dimethylammonium chloride Distearyldimethylammonium Chloride, Dicetyldimethylammonium Chloride, Dipolyoxyethylene Stearylmethylammonium Chloride, Stearyldimethylbenzylammonium Chloride, Stearyltrimethylammonium Chloride, Stearoylcholaminoformylmethylpyridinium Chloride, Cetyltrimethylammonium Chloride Cetyl trimethyl ammonium chloride, cetyl pyridinium chloride, tri(polyoxyethylene) stearyl ammonium chloride (5EO), Benzalkonium chloride, benzethonium chloride, etc. Polyoxyethylene(1) diethylmethylammonium chloride, myristyldimethylbenzylammonium chloride, methylbenzethonium chloride, lauryl dimethyl (ethylbenzyl) ammonium chloride, lauryl trimethylammonium chloride, lauryl pyridinium chloride Lauryl Dimethyl (Ethyl Benzyl) Ammonium Chloride, Lauryl Trimethyl Ammonium Chloride, Lauryl Pyridinium Chloride, Lauroyl Cholaminoformylmethylpyridinium Chloride, Alkyl Diaminoethyl Glycine Hydrochloride, Acylglutamic Acid of Hardened Tallow Fatty Acids, Self-Emulsifying Ethylene Glycol Monostearate, Glyceryl Monostearate Self-Emulsifying, Polyethylene Glycol (2) Monostearate Self-Emulsifying, Alkyl Isoquinolium Bromide, Trimethyl Stearyl Bromide, Cetyl Trimethyl Ammonium Bromide, Lauryl Trimethyl Ammonium Bromide, Condensed Ricinoleic Acid Poly (6) glyceryl, Wheat germ oil fatty acid glycerides, Lipophilic glyceryl monooleate, Lipophilic glyceryl monostearate, Hydrogenated soybean lysophospholipids, Hydrogenated soybean phospholipids, Hydrogenated soybean fatty acid glyceryl, Hydrogenated egg yolk lysophosphatidylcholine, Soybean lysophospholipids, soybean phospholipids, saturated fatty acid glycerides, cottonseed oil fatty acid glyceryl, egg yolk lecithin, and their salts of NaMg, K, Al, Zn, Ca, and triethanolamine. |

19. The delivery carrier into the cell of aspect 1, wherein a lipid is a amphiphile.
20. The delivery carrier into the cell of aspect 1, wherein a lipid being a surfactant is one or more substances selected from Table 4 and these surfactant forms a lamellar structure in an aqueous solution.

TABLE 4

| |
|---|
| 2-Alkyl-N-carboxymethyl-N-hydroxyethylimidazolinium betaine 2-Alkyl-N-carboxymethyl-N-hydroxyethylimidazolinium betaine,1,2-dioleoyl-sn-glycero-3-phosphoethanolamine, 14) triethanolamine aspartate, 2-alkyl-N-carboxymethyl-N-hydroxyethylimidazolinium betaine, N-acyl aspartate, N-Acylglutamic Acid, N-Acylsarcosine, N-Acylmethylalanine, N-Acylmethyltaurine N-Acylmethyltaurine, N-Stearoyl Dihydrosphingosine, N-Stearoyl Phytosphingosine, PEG-2 0 phytosterol, PEG-phytosterol, acyl(C12, acyl-N-methylamino acid, Acylamino Acid, Acyl Lactic Acid, Acetylethyl Carboxyl Methyl Thiazolidin Carboxylic Acid, Betaine Amino Acetate Amphoteric Surfactant, Alkyl (Alkenyl) Oligoglycosides, Alkyl Phenol Polyglycol Ethers, Alkoxylated Triglycerides, Phytosteryl Isothearate Emulgade NLB, Emulgade PL68/50, Emulgade SEPF, Emulgade Sucro, Emulgin B1, Emulgin B2, Emulgin B3, Emulgin S21, Caproyl Proline, Glycerophosphoric Acid, Glycerophospholipid, Glucuronic Acid, Cremophor A25, Cremophor GS 32, Cocamide MEA cocoylalanine triethanolamine, cocoyl glutamic acid, cocoyl glutamate triethanolamine, cocoyl methyl taurine, succinate, surfactin, lysine distearoyl glutamate, diphosphatidylglycerol (cardiolipin) Lysine Dystearoyl Glutamate (Cardiolipin), Lysine Dimyristoyl Glutamate, Lysine Dilauroyl Glutamate, Lysine Dirinoleoyl Glutamate, Stearoyl Glutamate, Dioctyldodecyl Stearoyl Glutamate, Sphingosine, Ceramide, Ceramide 1-Phosphonic Acid phosphonic acid, ceramide 1-phosphonic acid, ceramide aminoethyl phosphonic acid, cerebroside, sorbitan ester, soybean sterol, triethanolamine salts., palm kernel oil fatty acid amidopropyl betaine solution, palm fatty acid glutamic acid, palmitoyl aspartate ditriethanolamine, bis(Ns-lauroyl-L-lysine)sebacoylamide, Hydroxystearyl phytosphingosine, Polyoxyethylene glyceryl pyroglutamate isostearate, Polyoxyethylene hardened castor oil pyroglutamate isostearate, Glyceryl pyroglutamate oleate, Phytosterol, Phytosphingosine, Hexaglyceryl Monostearate, Phosphatidylinositol, Phosphatidylinositol Polyphosphate, Phosphatidylethanolamine, Phosphatidylglycerol, Phosphatidylcholine, Phosphatidylcholine (Lecithin), Phosphatidylserine, Phosphatidic Acid, Poly Polyol fatty acid esters, Polyoxyethylene alkyl ether acetate, Polyoxyethylene di-stearate, Polyoxyethylene sorbitan tristearate, Polyoxyethylene sorbitan fatty acid esters, Polyoxyethylene methyl glucose distearate, Polyoxyethylene monostearate, Polyoxyethylene lauryl ether, Polyoxyethylene hardened castor oil, Polyoxyethylene fatty acid amine sulfate, Polyquaternium-10, Polyquaternium-51, Polyquaternium-64 61, Polyquaternium-64, Polyquaternium-65, Polyquaternium-7, Myristoyl Glutamic Acid, Sodium myristoyl glutamate, Hexyldecyl myristoyl methylaminopropionate, Myristoyl methyl taurine, Polyoxyethylene sorbitan monooleate, Coconut oil alkylbetaine solution, Coconut oil fatty acid N-methyl ethanolamide Methyl Ethanolamide, Acylglycine Coconut Oil Fatty Acid, Acylglutamic Acid Coconut Oil Fatty Acid, Triethanolamine Coconut Oil Fatty Acid Acylglutamate, Amidopropyl Betaine Coconut Oil Fatty Acid, Glyceryl Coconut Oil Fatty Acid, Glutamic Acid Coconut Oil Fatty Acid, Sarcosine Coconut Oil Fatty Acid diethanolamide (cocamide DEA), coconut oil fatty acid methylalanine, coconut oil fatty acid methyl ethanolamide (cocamidomethyl ME A), coconut oil fatty acid methyl taurine, coconut oil fatty acid monoethanolamide (cocamide MEA), lauramidopropyl betaine lauryl aminodiacetic acid solution, Lauryl Diaminoethyl Glycine, Lauryl Dimethylamino Acetate Betaine, Lauric Acid Amidopropyl Betaine, Laureth Acetic Acid, Laureth Sulfate, Lauroyl Aspartate, Lauroyl Glutamic Acid, Lauroyl Glutamic Acid POE(2) octyldodecyl ether diester, POE(2) stearyl ether diester, POE(2) lauroyl glutamate diester (2) Stearyl Ether Diester, Di(octyldodecyl/phytosteryl/behenyl) Lauroyl Glutamate, Di(phytosteryl/octyldodecyl) Lauroyl Glutamate, Dihexyldecyl Lauroyl Glutamate, Triethanolamine Lauroyl Glutamate Triethanolamine, Lauroyl Glutamate Polyoxyethylene Octyldodecyl Ether Diester, Lauroyl Glutamate Polyoxyethylene Stearyl Ether Diester, Methylalanine Lauroyl Glutamate, Lauroyl Sarcosine, Lauroyl Sarcosine Triethanolamine, Lauroyl Methylalanine, Lauroyl Methylglycine, Lauroyl Methyl Taurine, Lauroyl Monoethanolamidosuccinate, Lanette WAXAO, Lysophosphatidyl Inositol, Lysophosphatidylethanolamine, lysophosphatidylglycerol, lysophosphatidylcholine, lysophosphatidylserine, lysophosphatidic acid, phospholipid phosphatidylglycerol, lecithin, ring-opening spiculesporic acid, cured coconut oil fatty acid glycerol sulfate, fatty amine polyglycol ether, fatty Alcohol polyglycol ethers, Fatty acid N-alkylglucamides, Fatty acid amide polyglycol ethers, Fatty acid alkanolamides, Fatty acid alkanolamide ether carboxylic acids, Fatty acid alkanolamide sulfate, Fatty acid glyceride sulfate, Fatty acid polyglycol esters, Hydrogenated cyclic Lysophosphatidic acid, Hydrogenated soybean phospholipid, Hydrogenated egg yolk phospholipid, Branched fatty acid (C12-31) cholesteryl, and their salts of Na, Mg, K, Al, Zn, Ca, triethanolamine. |

21. The delivery carrier into cell according to aspect 1, wherein the molecule containing the stimulatory-responsive polymer has a linear or branched polymer structure comprising one or more temperature, pH, and light-stimulating substances selected from Table 5.

TABLE 5

| (temperature-stimulus-responsive substance) |
|---|
| (Polyoxyethylene octylphenyl ether) acrylate, (Polyoxyethylene octylphenyl ether) methacrylate, (Polyoxyethylene nonylphenyl ether) acrylate, (Polyoxyethylene nonylphenyl ether) methacrylate (Polyoxyethylene lauryl ether) acrylate, (Polyoxyethylene lauryl ether) methacrylate, 1,2,4,5-tetrakis(1,2,4,5-tetrakis(N,N-dithiocarbamylmethyl)benzene, 1,3,5-tri(bromomethyl)benzene, 2-n-propyl-2-oxazoline, 2 N,N-dimethylaminoethyl acrylate, 2-N,N-dimethylaminoethyl methacrylate DMAEMA, 2-Amino-2-hydroxymethyl-l-hydroxymethyl-l-acrylate-2-hydroxymethyl-1,3-propanediol, 2 2-Amino-2-hydroxymethyl-1,3-propanediol (Tris), 2-Amino-2-hydroxymethyl-1,3-propanediol 2-Amino-2-hydroxymethyl-1,3-propanediol hydrochloride, 2-hydroxy-3-phenoxypropyl acrylate hydroxybutyl acrylate, 2-hydroxybutyl methacrylate, 2-hydroxypropyl acrylate, 2-hydroxypropyl methacrylate hydroxypropyl methacrylate, 3,5-tri(N,N-dithiocarbamylmethyl)benzene, 3-N,N-dimethylaminopropyl acrylamide, N-acryloyl aspartamide, N-acryloyl glycinamide, N-acryloyl glutamamide, N-acryloyl asparagamide N-methylacryloylaspartamide, N,N-dimethylmethacrylamide, N,N-dimethylacrylamide, N,N-methylenebisacrylamide N-methylenebisacrylamide, N,N-ethylmethylacrylamide, N,N-ethyl methylamide, N,N-ethyl methyl methacrylamide, N,N-dialkyl Dithiocarbamylmethyl, N,N-Dialkyl-Substituted Acrylamide Derivatives, N,N-Dialkyl-Substituted Methacrylamide Derivatives, N,N-Diethylacrylamide, N,N-Diethylamide, N,N-Diethylmethacrylamide N,N-Diethylmethacrylamide, N,N-Diethylamide, N,N-Diethylmethacrylamide, N,N-Diethylmethacrylamide, Sodium N,N-Dithiocarbamate-dithiocarbamate), N,N-dimethylacrylamide, N,N-dimethylmethacrylamide, N,N-propylacrylamide, N,N-propylmethacrylamide, N N-acryloyl piperidine, N-acryloyl morpholine, N-alkyl acrylamide, N-alkyl methacrylamide, N-acryloyl piperidine, N-acryloyl morpholine N-alkyl |

TABLE 5-continued

| |
|---|
| methacrylamide, N-alkyl substituted acrylamide, N-alkyl substituted methacrylamide N-alkyl methacrylamide, N-alkyl substituted acrylamide, N-alkyl substituted methacrylamide N-alkyl-substituted methacrylamide, N-allenylphthalimide, N-isopropylacrylamide, N-isopropylamide N-ethylethyl acrylamide, N-ethyl methacrylamide, N-ethoxyethyl acrylamide, N-ethoxyethyl amide, N-ethoxyethyl methacrylamide, N-cyclopropylacrylamide, N-cyclopropylamide, N-cyclopropylmethacrylamide, N-tetrahydrofurfurylacrylamide, N-cyclopropylamide, N-cyclopropylmethacrylamide tetrahydrofurfurylmethacrylamide, N-biotinyl-N'-methacloyltrimethylenamide, N-vinylacrylamide, N-vinylalkylacrylamide, N-vinylmethacrylamide, N-propylacrylamide, N-methacryloyl piperidine, N- or N,N-dialkyl-substituted methacrylamide derivatives, s-butylacrylamide, t-butylacrylamide, acroylglycinamide, acroylzarkosinamide, acroylnipecotamide, acroylmethyluracil, Acetyl Acrylamide, Ethyl Isopropyl Acrylamide, Ethylene Glycol/Propylene Glycol Copolymer, Ethylene Glycol Arenyl Methyl Ether, Oxyethylene Acrylate Derivatives, Oxyethylene Sorbitan Laureate, Oxyethylene Methacrylate Ester Derivatives, Oxyethylene Laurylamine, Acrylates with Oligoethylene Glycol Side Chains, Diisopropylacrylamide, Diethylacrylamide, Diethylaminoacrylate, Diethylamino-metaacrylate, Diethylene Glycol Alenyl Methyl Ether, Dibutylacrylamide, Dipropylacrylamide, Dimethylacrylamide, Dimethylaminoacrylamide, Dimethylaminoacrylate, Dimethylaminopropylacrylamide, Dimethylaminopropylmethacrylamide, Dimethylaminomethacrylamide, Dimethylaminomethacrylate, Sodium N,N-dithiocarbamate, Hexakis(N,N-dithiocarbamylmethyl) Benzene, Hexakis(bromomethyl)benzene, Methylacrylamide/N-acetylacrylamide copolymers, and their salts of Na, Mg, K, Al, Zn, Ca, triethanolamine and their derivatives. |
| (pH stimulus-responsive substance) |
| Glucosamine, chitosan, 2-ethoxyethyl vinyl ether, N-alkylacrylamide/polyacrylic acid, N-vinylalkylacrylamide, 4-(2-vinyloxyethoxy) benzoic acid, 6-(2-vinyloxyethoxy) hexanoic acid, 6-(Vinyloxy) hexanoic acid, isobutyl vinyl ether, their alkali metal salts and their derivatives, their Na, Mg, K, Al, Zn, Ca, triethanolamine salts and their derivatives |
| (Light stimuli-responsive substance) |
| N-alkylacrylamide, n-(4-phenylazophenyl) acrylamide, 6-[4-(4-pyridylazo) phenoxy] hexamethacrylate, N-vinylalkylacrylamide, 4-[2-(vinyloxy) ethoxy] azobenzene, 2-(2-Ethoxy) ethoxyethyl vinyl ether, salts of these Na, Mg, K, Al, Zn, Ca, triethanolamine and their derivatives |

22. The delivery carrier into the cell of aspect 1, wherein the emulsion stabilizer is one or more components selected from the polyvalent alcohol, the synthetic antioxidant, the ultraviolet absorber and the preservative listed in Table 6.

TABLE 6

| (Polyvalent alcohol) |
|---|
| Ethylene glycol, diethylene glycol, polyethylene glycol, propylene glycol, polypropylene glycol, glycerin, diglycerin, polyglycerin, 1,3-butanediol, 1,3-butanediol, triethylene glycol, dipropylene glycol, 3-methyl-1,3-butanediol, 1,2-pentanediol 2-pentanediol, 1,4-pentanediol, 1,5-pentanediol 1,5-pentanediol, 2,4-pentanediol, 2-methyl-2,4-pentanediol, 3-methyl-1,5-pentanediol,1,2-Hexanediol, 1,6-hexanediol, glycerin, diglycerin, triglycerin, polyglycerin, methyl butanediol, butylene glycol, Isoprene glycol, polyethylene glycol, pentanediol, hexanediol, propylene glycol, dipropylene glycol, polypropylene glycol, ethylene glycol, diethylene glycol, neopentyl glycol, polyethylene glycol, sorbitol, Xylitol, sodium pyrrolidonecarboxylate, hyaluronic acid, carrageenan, alginic acid, agar, fucoidan, pectin, locust bean gum, xanthan gum, tragacanth gum, guar gum, carboxymethyl cellulose, hydroxyethyl cellulose, polyvinyl alcohol, Polyvinyl alcohol, Polyvinylpyrrolidone, Carboxyvinyl polymer, Acrylic acid/methacrylic acid copolymer, Polyglutamic acid, Sodium alginate, Carrageenan, Agar, Furcellulan, Guar gum, Quince seed, Konjac mannan, Tamarind gum, Tara gum, Dextrin, Starch, Locust bean gum, gum arabic, gutti gum, karaya gum, tragacanth gum, arabinogalactan, pectin, marmello, chitosan, starch, cardran, xanthan gum, gellan gum, cyclodextrin, dextran, pullulan, microcrystalline cellulose, methyl cellulose Ethyl cellulose, hydroxyethyl cellulose, hydroxypropyl cellulose, hydroxypropyl methyl cellulose, carboxymethyl cellulose, carboxy starch, cationized cellulose, starch phosphate, cationized guar gum, Carboxymethyl and hydroxypropylated guar gum, hydroxypropylated guar gum, albumin, casein, gelatin, sodium polyacrylate, polyacrylamide, carboxyvinyl polymer, polyethyleneimine, highly polymerized polyethylene glycol, polyvinyl alcohol, polyvinyl alcohol, polyvinylpyrrolidone, polyvinyl ether, polyacrylamide, acrylic acid copolymer, methacrylic acid copolymer, maleic acid copolymer, vinylpyridine copolymer, ethylene/acrylic acid copolymer, vinylpyrrolidone polymer, vinyl alcohol/vinylpyrrolidone copolymer, nitrogen-substituted Nitrogen-substituted acrylamide polymers, amino-modified silicones, cationic polymers, dimethylammonium acrylate polymers, anionic polymers of acrylic acid, anionic polymers of methacrylic acid, modified silicones, alkyl methacrylate (C10-30) Copolymers, Polyoxyethylene/Polyoxypropylene copolymers. |
| (Synthetic antioxidant) |
| Butylhydroxyanisole, Butylhydroxytoluene, Propyl gallate, Erythorbic acid, Sodium erythorbate, Parahydroxyanisole, Octyl gallate |
| (Ultraviolet absorber) |
| Para-aminobenzoic acid derivatives such as para-aminobenzoic acid, ethyl para-aminobenzoate, glyceryl para-aminobenzoate, amyl para-dimethylaminobenzoate, 2-ethylhexyl para-dimethylaminobenzoate, benzyl cinnamate, Benzyl cinnamate, glyceryl mono-2-ethylhexanoate, methyl 2,4-diisopropyl cinnamate, 2,4-diisopropyl cinnamate, ethyl 2,4-diisopropyl cinnamate, potassium para-methoxycinnamate, sodium para-methoxycinnamate, isopropyl para-methoxycinnamate, 2,4-diisopropyl cinnamate Isopropyl para-methoxycinnamate, Isopropyl para-methoxycinnamate, 2-Ethylhexyl para-methoxycinnamate, Ethyl para-methoxycinnamate, etc., Urocanic acid derivatives, Ethyl para-methoxycinnamate, etc., Urocanic acid derivatives, 2,4-Dihydroxybenzophenyl 2,4-dihydroxybenzophenone, 2,2',4,4 2,4-dihydroxybenzophenone, 2,2',4,4'-tetrahydroxybenzophenone, 2-hydroxy-4-methoxy-5-sulfobenzophenone 5-sulfobenzophenone sodium, 2-hydroxy-4-methoxybenzophenone-5-sulfonic acid, 2-hydroxy-4-methoxybenzophenone, 2,2'-Dihydroxy-4,4'-dimethoxybenzophenone 2,2'-dimethoxybenzophenone, 2,2'- |

TABLE 6-continued

| |
|---|
| dihydroxy-4,4'-dimethoxybenzophenone 2,2'-dimethoxy-4,4'-dimethoxybenzophenone, 2,2'-dihydroxy-4,4'-dimethoxybenzophenone, 2,2'-dimethoxy-5-sulfobenzophenone sodium, etc. 2-Ethylhexyl salicylate, phenyl salicylate, benzyl salicylate, p-tert-butylphenyl salicylate phenyl salicylate, benzyl salicylate, p-tert-butylphenyl salicylate, homomenthyl salicylate,-3,3,5-trimethylcyclohexyl salicylate Salicylic acid derivatives such as benzyl salicylate, p-tert-butylphenyl salicylate, homomenthyl salicylate, salicylic acid-3,3,5-trimethylcyclohexyl salicylate Salicylic acid derivatives such as salicylic acid-3,3,5-trimethylcyclohexyl,2-(2'-hydroxy-5'-methoxyphenyl)benzotriazole,4-(tert-butyl-4'-methyl)benzotriazole tert-butyl-4'-methoxybenzoylmethane. Methoxybenzoylmethane. |
| (Preservative) |
| preservative:For example, benzoic acid, sodium benzoate, undecylenic acid, salicylic acid, sorbic acid, potassium sorbate, dehydroacetic acid, sodium dehydroacetate, isobutyl paraoxybenzoate, isopropyl paraoxybenzoate, isopropyl paraoxybenzoate, butyl paraoxybenzoate, paraoxybenzoic acid. Propyl acid, Benzyl paraoxybenzoate, Methyl paraoxybenzoate, Sodium methyl paraoxybenzoate, Phenoxyethanol, Photosensitizer 101, Photosensitizer 201, Photosensitizer 401, Radish extract, Grape seed extract |

23. The delivery carrier into the cell of aspect 1, wherein a stimulus-responsive-polymer containing molecule is covalently modified with one or more chemicals selected from the substance group in Table 7.

TABLE 7

| |
|---|
| Acrylamide, Acrylic Resins, Acrylic Acid, Metal Salts of Acrylic Acid, Amino Groups, Arginine, Alkyl Acrylate, Uracil Acrylate, Ethanediol, Ethyl Acrylamide, Ethyl Alcohol, Ethyl Butyl Acrylamide, Ethylene Oxide, Ethylene Glycol, Ethylene glycol derivatives, oxyalkylene, oxyethylene, oxytetramethylene, oxybutylene, oxypropylene, oxyhexylene, ornithine, cardran, polyamino acids with cationic groups in side chains, glycerin, styrene, cellulose, dextran sulfate, Tetramethylene glycol, Tryptophan, Hyaluronic acid, Biotinol acrylate, Histidine, Hydroxyethyl acrylate, Hydroxyethyl methacrylate, Hydroxypropyl cellulose, Hydroxyl group, Vinyl alkyl ether, Vinyl alcohol, Vinyl alcohol Partial Vinegarides, Vinyl Ether Derivatives, Vinyl Pyrrolidone, Vinyl Methyl Ether, Butyl Acrylamide, Butylene Glycol, Propyl Alcohol, Propyl Butyl Acrylamide, Propylene Glycol, Hexyl Acrylamide, Hexylene Glycol, Heparin, Pentylacrylamide, Polyacrylic acid, Polyarginine, Polyalginic acid, Polyethyleneimine, Polyoxyethylene, Polyoxypropylene, Polyrnithine, Polystyrene sulfonic acid, Polytryptophan, Polyhistidine, Polymethacrylic acid, Polylysine, Polyphosphoric acid, Methacrylamide, Methacrylamide Compounds, Methacrylsalcocinamide, Methacrylic Acid, Methacrylic Acid Esters, Metal Salts of Methacrylic Acid, Methanediol Group, Methyl, Methylacrylamide, Methyl Alcohol Group, Methyl Isopropyl Acrylamide, Methyl Ethyl Acrylamide, Methyl propyl acrylamide, methoxyethyl acrylate, methoxyethyl methacrylate, lysine, riboadenylic acid, nucleic acid, sulfated polysaccharides. |

24. The delivery carrier into the cell of aspect 1, wherein an active ingredient contains one or more substances selected from Table 8.

TABLE 8

| |
|---|
| Acridine, Ascorbic Acid, Ascorbic Acid Ca, Ascorbic Acid Na, Ascorbic Acid Glucoside, Ascorbic Acid Distearate, Ascorbic Acid Dipalmitate, Ascorbic Acid Stearate, Ascorbic Acid Palmitate, Ascorbic Acid Phosphate Mg, Ascorbic Acid Phosphate MgZn, Sodium Ascorbate Phosphate, Sodium Ascorbate Phosphate Palmitate, Astaxanthin, Acetyl Cysteine, Aminoalkylphenone, Aminolevulinic Acid, Antelaxanthin, Anthocyanin, Isoflavone, Iridium, Intein, Uroporphyrinogen, Uroporphyrin, Eosin Y, Ellagic acid, Erythorbic acid, Erythorbic acid, Catechin, Carotenoids, Carotene, Canthaxanthin, Xanthophyll, Coumarin, Curcumin, Glutathione, Glutamylcysteine, Chlorogenie acid, Chlorophyll, Coproporphyrin, Coproporphyrinogen, cyanidin, cyanocobalamin, cysteine, cytochrome c, dihydrolipoic acid, stilbene, zeaxanthin, semiquinone, thiol protein, thiochitosan, tetracycline, tetraphenylporphyrin, dehydrodascorbic acid, delphinidin, Tocotrienols, Tocopherols, Purpurins, Hydroquinone, Violaxanthin, Vitamin A, Hydroxymethyl Biran, Feriheme, Fucoxanthin, Phthalocyanine, Fullerene, Proanthocyanidins, Procyanidins, Protoporphyrinogen, Protoporphyrin, Pro vitamin A, paeonidine, petunidine, hematin, hemin, heme, hemoglobin, hemochromium, pelargodinin, verteporfin, benzoquinone, benzophenone, polyphilin, porphobilinogen, porphobilinogen, porotoporphyrin, magnesium, malvidin, metallothionein, metalloproteinase, methylene blue, ubiquitin, ubiquinol, ubiquinone, ubisemiquinone, lignan, lycopene, riboflavin, rutin, lutein, rubulene, retinal, retinoic acid, retinol, rose bengal, zinc, iron, copper, alpha-hydroxyacetophenone hydroxyacetophenone, α-lipoic acid. α-carotene, α-tocotrienol, α-tocopherol, β-lipoic acid, β-carotene, β-tocotrienol, β-tocopherol, γ-carotene, γ-tocotrienol, γ-tocopherol, δ-tocotrienol, δ-tocopherol, δ-carotene, and Their salts of Na, Mg, K, Al, Zn, Ca, triethanolamine and their derivatives. |

25. The delivery carrier into the cell of aspect 1, wherein the application of the delivery carrier is one type selected from pharmaceuticals, quasi-drugs, cosmetics, supplements, veterinary drugs, and miscellaneous goods.

26. The delivery carrier into the cell of aspect 1, wherein the formulation of the delivery carrier formulation is one or more of agents of topical, oral, suppository, drink, poultice, pack, spray, injection, dressing, liquid, ointment. The delivery carrier into cell of aspect 1, wherein the dosage form of the delivery carrier into cell is one or more of the following: topical, oral, suppository, oral, drink, pap, pack, spray, injection, dressing, liquid, ointment, aerosol, powdered, patterning, cream, topical spray, spray, granule, tablet, soft capsule, round, platelet dosage form, trochee, paste, solid dosage form, moist formulation, and stick-like formulation., powder, mould, cream, topical sprayer, dispersant, dispersant, granule, tablet, soft capsule, round, plate, troche, paste, solid, moisturizer, tic-like formulation. 27. The delivery carrier into cell of aspect 1, wherein the indication or effect of The delivery carrier into cell is one or more selected from Table 9.

TABLE 9

| |
|---|
| Skin cleansing effect, Suppression of rash, Suppression of swelling, Suppression of skin cracking, Suppression of acne, Suppression of rash, Prevention of skin roughness, Suppression of skin roughness, Suppression of pain, Suppression of groin sore, Suppression of skin roughness, Suppression of blotch, Suppression of stiff shoulders, Suppression of squeezing, Suppression of neuralgia, Suppression of eczema, Suppression of frostbite, Suppression of hemorrhoids, Suppression of periodontal disease, Suppression of back pain, Suppression of rheumatism, Relieving fatigue, Suppression of cold, Acne Treatment of acne, suppression of itching, suppression of armpits, suppression of sweat odor, antiperspirant effect, hair growth effect, prevention of thinning hair, prevention of hair loss, promotion of hair growth, suppression of hair loss after illness or childbirth, hair care, suppression of bad breath, improvement of emotional anxiety, whitening of teeth, oral cavity, prevention of periodontitis, treatment of alveolar pyorrhea, prevention of gingivitis, prevention of dentin deposition, prevention of halitosis, removal of tobacco mites, hair loss effect Prevention of sunburn, prevention of spots and freckles, prevention of snow burn, blemish treatment, suppression of vitiligo, senile pigmentation, treatment of melasma, skin glow, skin smoothness, skin elasticity, prevention of sagging, suppression of wrinkles, suppression of fine lines and wrinkles, prevention of periodontal disease, suppression of skin roughness, skin tightening, cleaning, sterilization, disinfection, virus killing, parasiticide, fungicide, antibody enhancement, disinfection, stain odor prevention Antibody enhancement, disinfection, stain odor control, moisturizing, oily odor control, moisturizing, oily skin improvement, skin protection, dryness prevention, hair and scalp sweat odor prevention, skin softening, skin elasticity maintenance, hair moisture and oil supply and maintenance, hair split prevention. |

28. The delivery carrier into cell of aspect 15, which is a temperature stimuli responsive polymer with an effective temperature of 45° C. to 70° C.

The present invention is a delivery carrier into the cell comprising a mixture of a molecule containing a stimulus-responsive polymer, a substance that simultaneously activates an autophagy-related gene and a cathepsin synthesis gene, and a lipid containing a hydrocarbon chain having eight or more continuously bound carbons, excluding the aforementioned two substances, each of which consists of one or more substances selected from three groups.

The reasons why the delivery carrier into the cell of the present invention have the above mentioned performance are as follows. In other words, it was found that the stability and surfactant power of substances having ATG and CTS activity, especially vitamin derivatives, do not necessarily correlate with the cell delivery rate, and that the cell absorption rate correlates nicely with ATG and CTS activity, as was evident in the embodiments of the present invention.

Because vitamins are important nutrients for human cell and their intracellular concentrations are higher than blood concentrations, they attach to vitamin-specific receptors on the cell surface in the first step, which are then actively transported by specific channel proteins in the second step. Stable vitamin derivatives adhere to vitamin receptors, but are not capable of active transport by specific channel proteins, etc., in the second step. In other words, vitamin receptors on the cell surface recognize a part of the vitamin molecule and attach only that part of the vitamin molecule, but in the second step, specific channel proteins recognize the entire vitamin molecule and take it up into the protein and pass it through the gate for active transport. When this state is maintained for a while, it is taken up into the cell by pinocytosis, an endocytosis that frequently takes up the extracellular fluid, and forms vesicles (endosomes) filled with the extracellular fluid. Vitamin receptors that bind to vitamin derivatives in the cell recover, degrade, and try to regenerate new vitamin receptors. Thus, the endosome activates CTS to form lysosomes, which fuse with the lysosomes to digest the vitamin derivatives in the vesicles, but some of the derivatives are degraded and released into the cell. This foreign substance is recognized by the autophagy system, which activates the ATG gene to form autophagosomes, activates the CTS to form lysosomes, and then fuses with it to degrade the vitamin derivatives in the vesicles. Thus, the vitamin derivatives taken up into the cell will eventually become vitamins available to the cell. Therefore, the delivery carrier into the cell of the present invention can be supplemented with a vitamin derivative with ATG and CTS activity to increase the adhesion of the delivery carrier into the cell to the cell and promote intracellular uptake.

Effects of the Invention

In other words, the delivery carrier into the cell of the present invention can deliver inclusions to the target tissue with high efficiency by enhancing the adhesion of the delivery carrier into the cell to the cell and promoting the intracellular uptake of useful ingredients. Furthermore, by modifying the surface with a stimulus-responsive-polymer containing molecule, specifically in the case of temperature-stimulus-responsive polymers or photo-stimulus-responsive polymers, the polymer becomes hydrophobic due to temperature rise or light irradiation, which reduces the hydration layer formed, thereby destroying the delivery carrier into the cell membrane and releasing the delivery carrier into the cell conjugate into the cell, thereby achieving a higher delivery rate. As a result, it is possible to achieve extremely high delivery efficiency to biological tissues, and to increase the delivery efficiency of pharmaceuticals, cosmetics, and nutritional supplements, and to achieve significant cost reductions, making this technology extremely useful in industry.

EMBODIMENTS OF THE INVENTION

The mechanism of the effect of The delivery carrier into cell of the present invention is shown in FIG. 1.

FIG. 1) This figure shows the effect of the Delivery carrier into cell. In FIG. 1, (5) represents the cell membrane, the upper side of (5) is extracellular, and the lower side of (5) is intracellular. (1) is a stimuli-responsive polymer-containing molecule bound to The delivery carrier into cell of the present invention. The active ingredient is shown in (2) and is conjugated in the Delivery carrier into cell. (1) contains a long tail-like structure, which represents the stimuli-responsive polymer, bound to the membrane of The delivery carrier into cell by a surfactant lipid (ellipse). (3) is a simultaneous activator of autophagy-related genes and cathepsin synthesis genes, such as a vitamin derivative, which is also connected to the membrane of The delivery carrier into cell due to its amphiphilic nature. In A, it is a delivery carrier into cell bound to a vitamin receptor (indicated by a square and a circle with the top missing) that penetrates the cell membrane (5). It is a Delivery carrier into cell. In this way, the vitamin derivative (3) binds to the vitamin receptor on the surface of the cell membrane. However, because the molecular shape is different from that of the original vitamin, the vitamin is not transported through the vitamin transport channel, and a part of the cell membrane is depressed to form a pouch B). C) The endosomal carrier becomes hydrophobic due to the contraction of the stimuli-responsive polymer on the cell surface by external stimuli such as temperature and light. The parallelism of the membranes collapses and the membrane of The delivery carrier into cell is easily destroyed, releasing the active ingredient into the endosome. On the other hand, (6) is a lysosome with digestive enzymes (small squares). D) The lysosome fuses with the endosome and transfers the digestive enzymes to the endosome. D) The lysosome fuses with the endosome and transfers digestive enzymes to the endosome, where they degrade (digest) the molecules in the endosome E). F) Finally, the endosome is destroyed and the vitamin derivative is converted into a vitamin that can be used by the cell. F) Eventually, the endosome is destroyed and the active ingredient (black ▲), vitamin (oval), and undigested vitamin derivative (7) are released into the cell. The undigested vitamin derivatives further activate the autophagy system and are digested by autophagosomes and finally converted into vitamins for use by the cells. In this way, they can be used by cells.

In pH-stimulated responsive polymers, the effect is thought to be exerted by the involvement of proton sponge effect in vesicles such as endosomes and lysosomes after uptake into the cell. The proton sponge effect is a phenomenon in which a compound that protonates in a weakly acidic environment is taken up into the vesicles, and the protonation inhibits the decrease of pH in the vesicles, and the influx of large amounts of proton and chloride ions into the vesicles increases the osmotic pressure in the vesicles, causing the swelling and rupture of the vesicles. For example, cationic polymers with large amounts of amino groups, such as chitosan with a polyglucosamine structure, exhibit this effect. In particular, this hypothesis was proposed by Behr et al. as a method to assist endosome escape in nucleic acid delivery systems. The endosomal membrane produced by endocytosis contains a proton pump called V-ATPase that transports protons into the endosome until the pH in the endosome reaches about 5-6. Cationic polymers with a proton sponge effect have a buffer zone at pH 5-7 and absorb large amounts of protons as the pH in the endosome decreases. This inhibits the decrease in pH in the endosome and requires the influx of more protons to decrease the pH. Anions also flow in to maintain electrical equilibrium inside and outside the endosome, leading to an increase in salinity and osmotic pressure. This high osmotic pressure is relieved by the influx of an even larger amount of water into the endosome, which can no longer withstand its capacity and disintegrates the membrane, thereby promoting the endosomal escape of the delivery carrier into the cell inclusion. The vitamin derivatives that can be used in the present invention that are recognized and bound to vitamin receptors at the cell surface may be selected from one or more substances selected from the group of vitamin derivatives shown in Table 2, and our screening has confirmed that these derivatives, unlike conventional vitamins and their derivatives, are not transported by vitamin transport channels and are bound to vitamin transport channels and remain endocytosed on the surface of detailed membranes. Finally, it was confirmed that these vitamin derivatives were transported into the cells by endocytosis.

The inventors of the present invention performed an exhaustive analysis using DNA chips after culturing human epidermal fibroblasts using a mixture of three different vitamin derivatives, namely, ascorbyl-3Na phosphate (APS), ascorbyl-3Na palmitate (APPS) and k (ascorbyl/tocopheryl)phosphate (EPC). And we found that the mixture activated many autophagy-related genes (ATG) and cathepsin (CTS), a lysosome-localized protease, compared to the RNA levels of the additive-free control. Therefore, the same evaluation as above was carried out on 84 vitamin derivatives, and it was found that some of the derivatives were highly active and others were low active, and the present inventors thought of applying the highly active ones to the delivery carrier into the cell of the present invention. The present inventors conducted clinical trials on the effects of vitamin derivatives with different ATG and CTS activities on the cellular uptake of carriers for cell delivery, and found that ATG and CTS activities were correlated with the cell delivery rate. Furthermore, the combination of stimulus-responsive substances, lipids, surfactants and stabilizers, which are components of the carrier, were investigated, and the stability test and surfactant force test, which are indispensable for stabilizing the carrier, were carried out to narrow down the substances that can be applied to the delivery carrier into the cell that achieves the high cell transport efficiency of the present invention.

Polyethylene imine (PEI) and polyamide amine dendrimers are known to have a proton sponge effect and have been widely used for efficient gene transfer. Recently, it has been reported that the buffering capacity of chitosan is superior to that of PEI in the pH range (4.5-7) in endosomes. The delivery carrier into the cell of the present invention shall comprise at least a mixture in which one or more substances are selected from at least three groups of simultaneous activators of autophagy-related genes and cathepsin synthesis genes, a stimulus-responsive-polymer containing molecule, and a lipid containing a hydrocarbon chain having eight or more continuously bound carbons. In addition to the above, an existing emulsion stabilizer is preferably selected to improve the stability of the Delivery carrier into cell.

As an emulsion stabilizer that can be used in the present invention, it is preferable if one or more components selected from the polyvalent alcohol, synthetic antioxidant, ultraviolet absorber, and preservative listed in Table 6 above are selected, and preferably one or more substances selected from the polyvalent alcohol, synthetic antioxidant, ultraviolet absorber, and preservative respectively. These stabilizers can be added to the entire delivery carrier into the cell of the present invention in the range of 0.01 to 10% by weight. If the ratio is higher than this, the toxicity will increase, and if it is lower than this, it will be difficult to achieve the stability effect.

The autophagy-related genes and cathepsin synthesis genes of the simultaneous activators of the autophagy-related genes and cathepsin synthesis genes of the invention are the genes registered in the Human Genome Nomenclature Committee (HGNC) of the International Organization for Human Genome Research (IGR), and their details are shown in Tables 10 and 11. In this invention, only the approved symbols of HGNC are used, but since there are several previous symbols and synonyms, they are arranged in the following table. Genes with different names and symbols in previous symbols and synonyms have also been confirmed to be identical to the genes in the HGNC approved symbols.

For the delivery carrier into the cell of the present invention, a substance that simultaneously activates the autophagy-related gene in Table 10 below and the cathepsin synthesis gene in Table 11 below must be used, the most preferred example of which is a limited vitamin derivative.

Autophagy-Related Gene (ATG)

TABLE 10

| Gene ID of HUGO Genc Nomenclature Committee (HGNC) | HGNC approval code | HGNC approval name | Conventional symbol | Synonym |
|---|---|---|---|---|
| HGNC:12558 | ULK1 | unc-51 like autophagy activating kinase 1 | | ATG1, ATG1A |
| HGNC:13480 | ULK2 | unc-51 like autophagy activating kinase 2 | | KIAA0623, Unc51.2, ATG1B |
| HGNC:29028 | ATG2A | autophagy related 2A | | KIAA0404 |
| HGNC:20187 | ATG2B | autophagy related 2B | C14orf103 | FLJ10242 |
| HGNC:20962 | ATG3 | autophagy related 3 | APG3L | PC3-96, FLJ22125, MGC15201, DKFZp564M1178 |
| HGNC:16489 | ATG4A | autophagy related 4A cysteine peptidase | AUTL2, APG4A | |
| HGNC:20790 | ATG4B | autophagy related 4B cysteine peptidase | APG4B | Apg48, KIAA0943, DKFp586D1822, AUTL1 |
| HGNC:16040 | ATG4C | autophagy related 4C cysteine peptidase | AUTL1, APG4C | FLJ14867, AUTL3 |
| HGNC:20789 | ATG4D | autophagy related 4D cysteine peptidase | AUTL4, APG4D | APG4-D |
| HGNC:589 | ATG5 | autophagy related 5 | APG5L | ASP, APG5, hAPG5 |
| HGNC:1034 | BECN1 | beclin 1 | | ATG6, VPS30 |
| HGNC:16935 | ATG7 | autophagy related 7 | APG7L | GSA7, DKFZp434N0735 |
| HGNC:4067 | GABARAP | GABA type A receptor-associated protein | | MM46, ATG8A |
| HGNC:4068 | GABARAP L1 | GABA type A receptor associated protein like 1 | | gec1, APG8L, ATG8L, ATG8B |
| HGNC:13291 | GABARAP L2 | GABA type A receptor associated protein like 2 | | GEF2, ATG8, GATE16, GATE-16, ATG8C |
| HGNC:6838 | MAPILC3A | microtubule associated protein 1 light chain 3 alpha | | MAP1BLC3, MAP1ALC3, LC3, LC3A, ATG8E |
| HGNC:13352 | MAPILC3B | microtubule associated protein 1 light chain 3 beta | | ATG8F |
| HGNC:34390 | MAPILC3B2 | microtubule associated protein 1 light chain 3 beta 2 | | ATG8G |
| HGNC:13353 | MAP1LC3C | microtubule associated protein 1 light chain 3 gamma | | ATG8J |
| HGNC:22408 | ATG9A | autophagy related 9A | APG9L1 | FLJ22169 |
| HGNC:21899 | ATG9B | autophagy related 9B | NOS3AS | FLJ14885, APG9L2, SONE |
| HGNC:20315 | ATG10 | autophagy related 10 | APG10L | DKFZP58610418, FLJ13954 |
| HGNC:588 | ATG12 | autophagy related 12 | APG12L | APG12 |
| HGNC:29091 | ATG13 | autophagy related 13 | KIAA0652 | |
| HGNC:19962 | ATG14 | autophagy related 14 | KIAA0831 | ATG14L |
| HGNC:21498 | ATG16L1 | autophagy related 16 like 1 | APG16L, ATG16L | WDR30, FLJ10035, ATG16A |
| HGNC:25464 | ATG16L2 | autophagy related 16 like 2 | | FLJ00012, WDR80, ATG16B |
| HGNC:15574 | RB1CC1 | RB1 inducible coiled-coil 1 | | KIAA0203, Cc1, |

TABLE 10-continued

| Gene ID of HUGO Genc Nomenclature Committee (HGNC) | HGNC approval code | HGNC approval name | Conventional symbol | Synonym |
|---|---|---|---|---|
| | | | | DRAGOU14, FIP200, ATG17, PPP1R131 |
| HGNC:25471 | WIPI1 | WD repeat domain, phosphoinositide interacting 1 | | FLJ10055, WIP149, ATG18, ATG18A |
| HGNC:32225 | WIPI2 | WD repeat domain, phosphoinositide interacting 2 | | ATG21, CGI-50, FLJ12979, FLJ14217, FLJ42984, DKFZP434J154, DKFZp686P02188, ATG18B |
| HGNC:23685 | SNX30 | sorting nexin family member 30 | | ATG24A |
| HGNC: 11175 | SNX4 | sorting nexin 4 | | ATG24B |
| HGNC:25679 | ATG101 | autophagy related 101 | C12orf44 | FLJ11773 |

Cathepsin Synthesis Gene (Cathepsin)

TABLE 11

| Gene ID of the Human Genome Organization's HGNC | HGNC appoval code | HGNC approved name | Conventional symbol | Synonym |
|---|---|---|---|---|
| HGNC: Human Genome Nomenclature Committee | | | | |
| HGNC:9251 | CTSA | cathepsin A | GSL, PPGB | |
| HGNC:2527 | CTSB | cathepsin B | | |
| HGNC:2528 | CTSC | cathepsin C | PLS, PALS | DPP1 |
| HGNC:2529 | CTSD | cathepsin D | CPSD | CLN10 |
| HGNC:2530 | CTSE | cathepsin E | | |
| HGNC:2531 | CTSF | cathepsin F | | CATSF, CLN13 |
| HGNC:2532 | CTSG | cathepsin G | | CG |
| HGNC:2535 | CTSH | cathepsin H | CPSB | ACC-4, ACC-5, ACC4, ACC5 |
| HGNC:2536 | CTSK | cathepsin K | CTSO2, CTSO, PYCD | PKND |
| HGNC:2537 | CTSL | cathepsin L | CTSL1 | FU31037 |
| HGNC:2542 | CTSO | cathepsin O | CTSO1 | |
| HGNC:2545 | CTSS | cathepsin S | | |
| HGNC:2538 | CTSV | cathepsin V | CTSL2 | CTU |
| HGNC:2546 | CTSW | cathepsin W | | |
| HGNC:2547 | CTSZ | cathepsin Z | | CTSX |

In the simultaneous activator of the present invention, only substances that can simultaneously activate one or more of the autophagy-related genes and cathepsin synthesis genes listed in Tables 10 and 11 above can be used, but substances that simultaneously activate one or more of the autophagy-related genes and cathepsin synthesis genes listed in Table 1 are particularly suitable. For the evaluation method of gene activation of the invention, all of the normally used DNA and corresponding RNA gene expression analysis methods can be used, including, but not limited to, real-time PCR, digital PCR, next-generation sequencing, microarray analysis, Sanger sequencing, quantigen RNA assay, and laser capture microdissection. Table 1 describes only the approved symbols of HGNCs for autophagy-related genes listed in Tables 10 and 11 above, but the ID of the Human Genome Nomenclature Committee (HGNC), the approved name of the HGNC, the previous symbols, and synonyms of the Human Genome Nomenclature Committee (HGNC) of the Organization for Human Genome Research may be used.

As a lipid containing a hydrocarbon chain with eight or more continuously bonded carbons that can be used in the present invention, the lipid is the most desirable, and either a surfactant having a surfactant action or a surfactant can be used. Lipids containing more than eight continuously bonded hydrocarbon chains of carbons enhance the stability of the delivery carrier into the cell; carbons below 7 decrease the stability of the delivery carrier into the cell and similarly decrease the stability of the delivery carrier into the cell at carbons above 30. Furthermore, preferably, the simultaneous presence of both lipids and surfactant substances is suitable for further enhancing the stability of the delivery carrier into the cell. In other words, the main part of the delivery carrier into the cell of the present invention comprises a lipid and a substance having a surfactant action, and furthermore, it is most preferably arranged in this emulsion membrane as a substance having a lipid and a surfactant action and a stimulus-responsive-polymer containing molecule ion-bonded to the constituent unit or surface of the membrane as shown in FIG. 2 or FIG. 3. The cell transport carrier of the present invention as shown in aspect 13, wherein one or more of the substances of either the autophagy-related gene and cathepsin synthesis gene simultaneous activators and the stimulus-responsive-polymer containing molecule [A] form part of a membrane molecule predominantly composed of lipids, is the cell transport carrier of aspect 1, wherein the representative structure may be, but is not limited to, the structure shown in FIG. 2.

FIG. 2 shows an example 1 of a typical structure of a lipid bilayer membrane used as a Delivery carrier into cell.

FIG. 3 shows an example 2 of a typical structure of a lipid bilayer of a cell delivery carrier. The cell delivery carrier may also be a lipid monolayer, in which case the membrane structure shown in the uppermost (outermost) layer of the figure may be used. The lipids of the membrane molecules in the outermost layer can contact the lipids of the inner membrane molecules to form a bilayer structure.

The lipid constituting the delivery carrier into the cell of the present invention may be a lipid containing a hydrocarbon chain having eight or more continuously bonded carbons, but preferably it should be a lipid or a lipid having surface activity. Furthermore, they are preferable if they have membrane fusion performance and have ionic lipids such as cationic, anionic or amphoteric lipids as membrane constituents.

The lipids that can be used in the carriers of the present invention can be used as long as they are liquid at 35° C. and, when used together with the vitamin derivatives in Table 2 above, suppress the decay rate of the vitamin derivatives to 20% or less and keep the vitamin derivatives stable in an accelerated test at 40° C. and 80% humidity for 6 months. Among the lipids that meet these conditions, those that can specifically suppress the decay rate of the vitamin derivatives to 10% or less are shown in Table 3. Among the lipids which can be used in the carrier of the present invention, those having surface activity can be used as long as they are liquid at 35° C. and, when used together with the vitamin derivative of the above-mentioned table 2, suppress the decay rate of the vitamin derivative to 20% or less and keep it stable in an accelerated test at 40° C., 80% humidity for 6 months. Among the lipids which satisfy these conditions, those having surface activity which are particularly suitable for the present invention are those which contain inclusions under an optical microscope and are able to confirm the existence of a lamellar structure and further suppress the decay rate of the vitamin derivative to 10% or less and keep the vitamin derivative stable, and the existence of the lamellar structure can be confirmed by direct observation of multilayers by the dyeing electron microscope method, which is a well-known method, or by observation of maltase cross polarization under a polarized light microscope. Among them, the lipid having a surfactant action shown in Table 4 is very suitable for the present invention because the lipid having a high stability and a good lamella formation action in which a plurality of layer structures can be confirmed was admitted by the present inventors.

For example, the lipid that can be used in the present invention may be a lipid formed from a lipid or a polymer, etc. having a delivery carrier into the cell membrane fusion performance, or the cationic lipid or the anionic lipid itself may be a lipid having a membrane fusion performance. In the delivery carrier into the cell of the present invention, the lipid included as a membrane component or the lipid having surface activity may be one type or a combination of two or more types. Alternatively, phospholipids, etc., may be mentioned. They may be used alone, or two or more of them may be used together. The term membrane fusion performance in the present invention refers to the fusion performance to endosomes, autophagosomes, lysosomal membranes, or cell membranes.

Examples of cationic lipids include, for example, 1,2-dioleoyl-3-Trimethylammonium propane (DOTAP), N-[1-(2,3-dioleoyl propyl])]-N,N-dimethylamine (DODAP), N,N-dioleyl-N,N Dimethylammonium chloride (DODAC), N,N-distearyl-N,N Dimethylammonium bromide (DDAB), N-(1-(2,3-dioleoyloxy) pro (pyr)-N,N,N-trimethylammonium chloride (DOTMA), N,N-dimethyl-2,3-Dioleoyloxy-propylamine (DODMA), 2,3-dioleoyloxy-N-[2-(spermine carboxyamide)ethyl]-N,N-dimethyl-1-Propanaminium trifluoroacetic acid (DOSPA), N-[1-(2,3-)(Ditetradecyloxypropyl)]-N,N-dimethyl-N-hydroxyethyl bromide Ammonium (DMRIE), N-[1-(2,3-dioleoyl oxypropyl)-N,N— Lipids that are not phospholipids, such as dimethyl-N-hydroxyethyl ammonium bromide (DORIE) The following are listed. Alternatively, phospholipids and the like can be listed. These may be used alone or in combination with two or more of them.

Phospholipids and others that can be used in the present invention include, for example, phosphatidylethanolamine, phosphatidyl ethanolamine Phosphatidylcholine, lysophosphatidylcholine, phosphatidylglycerol, and Phosphatidic acid, phosphatidylserine, phosphatidylinositol, cardiolipin, and Phosphorus such as natural phospholipids such as sphingomyelin, soy lecithin, egg yolk lecithin, and lysolecithin Polymeric succinylated polyglycidol (SucPG), with lipid and membrane fusion capabilities. The phosphatidylethanolamine is 1,2-dioleoyl-sn-glycero-3-Phosphoethanolamine (DOPE), 1,2-dilinoleoyl-sn-glycero-3-Phosphoethanolamine (DLoPE), 1,2-dielcole-sn-glycero-3-Phosphoethanolamine (DEPE), 1,2-dimyristoyl-sn-glycero-3-Phosphoethanolamine (DMPE), 1,2-dipalmitoyl-sn-glycero-3-Phosphoethanolamine (DPPE), 1,2-distearoyl-sn-glycero-3-Phosphoethanolamine (DSPE), for example. In addition, it is preferable that the lipid in the present invention includes phospholipids as a membrane constituent, since it can further reduce cell death.

Examples of anionic lipids that can be used in the present invention include phosphatidylserine, phosphatidylglycerol, phosphatidic acid, phosphatidylinositol or phosphatidylinositol, or their lysophospholipids, lipid peroxides, oxides, plasmalogens or diether lipids.

When molecules containing ionic stimulus-responsive polymers are ionically bonded, the lipids of the present invention are preferably lipids having an ionic nature opposite to that of the stimulus-responsive polymer, for example, cationic lipids such as polyglucosamine, chitosan, etc. In the case of ionic bonding of the polymers of the present invention having a large number of amines to the surface of the cell delivery carrier of the present invention, it is suitable to use anionic, non-cationic or amphoteric lipids in various proportions or all of them. Among these, the use of anionic lipids is more preferred.

The delivery carrier into cell of the present invention is more excellent in the effect of suppressing cell death after cell delivery, and is also excellent in the efficiency of intracellular delivery. The compounding ratio of the non-phospholipid lipid and the membrane fusion lipid preferably has a molar ratio of 3:0.5 to 20, which is excellent in intracellular delivery efficiency, and is contained as a membrane component. When scaling down for a better molar ratio, the molar ratio is 3:5 to 10. Further, in the present invention, it is preferable to contain 1,2-dioleoyl-3-trimethylammonium propane (DOTAP) as a membrane fusion lipid as a lipid. Further, in the present invention, 1,2-dioleoyl-sn-glycero-3-phosphoethanolamine (DOPE) is contained in the above molar ratio. A membrane composition comprising a cell delivery agent carrier.

The stimulus-responsive polymer-containing molecule in the present invention may be a stimulus-responsive polymer or a derivative of the stimulus-responsive polymer. The derivative of this stimulus-responsive polymer is preferably a substance in which the stimulus-responsive polymer is chemically bonded to a lipid or a molecule having a structure similar to this. In the examples, this is referred to as a stimulus-responsive polymer-bound lipid, which is a suitable example of a stimulus-responsive polymer-containing molecule.

More preferably, The delivery carrier into cell membrane is composed mainly of surfactant lipids and the stimuli-responsive polymer is a substance chemically bonded to a surfactant lipid or a molecule with a similar structure that is a major component of The delivery carrier into cell membrane. The stimuli-responsive polymer should be chemically bonded to a surfactant lipid or a molecule with a similar structure, which is a major component of the membrane of The delivery carrier into cell. The stimuli-responsive substances that can be used in the carriers are one or more of the following: temperature-responsive, pH-responsive, and light-responsive substances. This substance can be a linear or branched monomer or polymer structure. In addition, the properties of stimuli-responsive substances that are more effective in the present invention are those that, when used in combination with the vitamin derivatives listed in Table 2 above, suppress the decay rate of the vitamin derivatives to less than 20% and maintain stability in an accelerated test at 40° C., 80% humidity, for 6 months. The inventors found that if one or more stimuli-responsive substances selected from the substance groups in Table 5 are used, it is possible to make a Delivery carrier into cell that can have the more better stability of these conditions. In addition, we found that these stimuli-responsive polymers can be used to make delivery carrier into cell s that have these conditions of more better stability. Furthermore, it was found that The delivery carrier into cell s of the invention containing these stimuli-responsive polymers did not more break down when the carriers were observed under a normal optical microscope and a polarized light microscope after a storage test in which the carriers were stored at 40° C. and 80% humidity for 6 months. After 6 months of storage test at 40° C. and 80% humidity, the carriers were observed under normal light and polarized light microscopes. When the carrier is not destroyed, the fluorescent dye is encapsulated under the microscope in the carrier as it was at the start of the test, and the existence of maltase cross polarization was confirmed under a polarization microscope. In addition, the attenuation rate of the vitamin derivative should be measured, after the above storage test, the decay rate of the vitamin derivative was suppressed to less than 10%, and the vitamin derivative can be more kept stable, it is particularly useful for this invention. As an example of these stimuli-responsive substances, it is desirable to use stimuli-responsive polymers chemically modified by covalent bonding with one or more chemical substances selected from the substance groups in Table 7 above, in terms of effectiveness.

In one example of the main present invention, the lipid to which the stimulus-responsive polymer is bound is in contact with the hydrocarbon portion of the lipid exhibiting the surface activity of the membrane component of the carrier or the hydrocarbon portion of the lipid, and the stimulus-responsive polymer is dispersed in the aqueous solvent portion outside the carrier. Therefore, the structure is as if the stimulus-responsive polymer protruded from The delivery carrier into cell membrane to the outer solvent side. This state is allow the carrier membrane for cell delivery to be modified with stimuli-responsive polymers. In this case, the stimulus-responsive-polymer containing molecule modified with the lipid of vitamin derivative will be more likely to be used as a vitamin after disintegration in the cell. In view of its superiority in inhibiting cell death and efficiency of intracellular delivery, we have decided to use the following as membrane components The stimulus-responsive-polymer containing molecules are preferably 0.05 to 40 mole % of the total lipids of It is more preferable to be 1.0 to 20 mole %, and 2.0 to 8.0 mole % best. Temperature, pH, and light stimuli-responsive polymer-containing molecules in the present invention can be used in conjunction with membrane-fusing lipids, and It can also bind with 1,2-dioreoil-sn-glycero-3-phosphoethanolamine (DOPE).

The temperature-responsive polymer forms a hydration layer on the surface of The delivery carrier into cell at temperatures below the Lower Critical Solution Temperature (LCST) and reduces the affinity between The delivery carrier into cell and the cell membrane. Above the lower critical solubility temperature, it aggregates and becomes hydrophobic, improving the affinity between The delivery carrier into cell and the cell membrane. Furthermore, as hydrophobization progresses, the membrane equilibrium is disrupted and the membrane is destroyed. Thus, the temperature-responsive polymer in the present invention can move freely in the tissues by reducing the affinity between The delivery carrier into cell and the cell membrane when the lower critical dissolution temperature in water is low. By raising the temperature in anticipation of the time required to reach the target cells, the cell membrane adhesion is enhanced and the endocytosed delivery carrier into cell is disintegrated, helping the substances in The delivery carrier into cell to diffuse into the cells. A similar phenomenon can occur with pH- and light-stimuli-responsive polymers, not by temperature elevation stimulation but by pH changes inside and outside the membrane or light stimulation by devices.

The lower critical dissolution temperature of the temperature-stimuli-responsive polymer-containing molecules in the present invention in water should be between a temperature close to body temperature and 70° C., which is the maximum temperature for carrier transportation in summer during product distribution (e.g., 35.0 to 70.0° C.). On the other hand, for the temperature-responsive polymer of the present invention, even if the lower critical dissolution temperature is near body temperature, it is easier to suppress cell death after delivery into cells if the temperature is as high as possible. Thus, the lower critical dissolution temperature of the temperature-responsive polymer in water is preferably from 37.0 to 42.0° C., more preferably from 37.5 to 41.0° C., and even more preferably from 38.0 to 40.5° C., since the polymer is excellent in intracellular delivery and easily suppresses cell death after delivery of nucleic acid into cells. The temperature range of 38.0 to 40.5° C. is even more preferable. In the present invention, the lower critical dissolution temperature of the temperature-responsive polymer in water is measured by differential scanning calorimetry (DSC).

Specific examples of monomers that are constituent units of temperature, pH, and light stimulus-responsive-polymer containing molecules contained in delivery carrier into the cell in the present invention are as indicated in the claims of the present invention.

For example, polymers composed of these monomers by monopolization or two or more of these The polymer may be a copolymer of the monomers of the above. Copolymerization with monomers other than those monomers, graft polymerization or copolymerization of polymers may be used. or by using a mixture of monopolizers and copolymers of these monomers. may also be used. The temperature-stimulus-responsive polymer may also be cross-linked to the extent that the intrinsic properties of the polymer are not impaired.

The lower critical dissolution temperature of the temperature-stimulus-responsive polymer in water can be adjusted by selecting the monomers that make up the temperature-stimulus-responsive polymer as described above according to the properties of each monomer.

Copolymers of various stimulus-responsive monomers and other monomers such as dimethylaminopropylacrylamide (DMAPAA) can be used as polymer-containing molecules that are responsive to temperature, pH, and light, because they are excellent for delivery into the cell and easily inhibit cell death after delivery into the cell. The molar number of various stimulus-responsive monomers and other monomers in the polymer, it is more preferable that the various stimulus-responsive monomers are 90-99 and the other monomers are 1-10.

For example, the copolymer of N-isopropyl (meth)acrylamide (NIPAA) and dimethylaminopropyl acrylamide (DMAPAA) can be used as a temperature-stimulus-responsive polymer because it is excellent in delivering into the cell and easily inhibits cell death after delivery into the cell. As for the molar number of NIPAA and DMAPAA in the polymer, it is more preferable that NIPAA is 90-99 and DMAPAA is 1-10.

The molecular weight of the molecules in the present invention is not particularly limited to the temperature, pH, and molecular weight of the light-stimulus-responsive-polymer containing molecules, for example, the weight average molecular weight may be 1000 to 1000, but it is preferable to have a weight average molecular weight of 2000 to 7000 because it is excellent for delivery into the cell and it is easy to inhibit cell death after delivery into the cell. The weight average molecular weight can be measured by gel filtration chromatography (GPC).

To modify the surface of a delivery carrier into the cell with a temperature-stimulus-responsive polymer, for example, when preparing a delivery carrier into the cell from a cationic or anionic lipid and a membrane fusion lipid, the temperature-stimulus-responsive polymer is chemically modified in advance by either the membrane fusion lipid or the cationic or anionic lipid, and the lipid-modified temperature-stimulus-responsive polymer is mixed with the lipid during the preparation of the delivery carrier into the cell, so that after preparation of the delivery carrier into the cell, the surface becomes a structure modified by the temperature-stimulus-responsive polymer.

The method of preparing a Delivery carrier into cell of the present invention can be a conventional method. For example, when the delivery carrier into the cell of the invention is prepared from a cationic or anionic lipid or anionic lipid and a membrane-fused lipid, the cationic or anionic lipid or anionic lipid and the membrane-fused lipid are dissolved in a solvent (e.g., chloroform, etc.), the solvent is removed, the thin film of lipid formed is hydrated with phosphate-buffered saline, etc., and then the particle size of the delivery carrier into the cell is adjusted by ultrasonication and extruder treatment.

The particle size of the delivery carrier into the cell is not particularly limited, for example, an average particle size of 0.05 to 1 μm can be used. The average particle size of The delivery carrier into cell was measured by dynamic scattering (DLS).

The delivery carrier into the cell of the present invention may have a structure in which one or more of the vitamin derivatives and the stimulus-responsive-polymer containing molecules constitute an emulsion film of the delivery carrier into the cell. The delivery carrier into the cell of the present invention may also have a structure in which one or more of the vitamin derivatives and the stimulus-responsive-polymer containing molecules are ion-linked to the surface of the delivery carrier into the cell.

The cells to be delivered by The delivery carrier into cell of the present invention are not particularly limited, and include, for example, keratinocytes, spinous cells, granular cells, keratinocytes, fibroblasts, pigment cells, dendritic cells, Langerhans cells, Merkel cells, vascular endothelial cells, sebaceous gland cells, eccrine gland cells, apocrine gland cells, adipocytes, Merkel's disc cells Hair follicle cells, hair papilla cells, hair matrix cells, hair matrix cells, hair fiber cells, inner hair root sheath cells, outer hair root sheath cells, cuboidal epithelial cells, podocyte cells, erector pili muscle cells, skin stem cells, hair follicle stem cells, pigment stem cells, sweat gland cells, sebaceous gland cells, hair follicle funnel cells, lung cells, colon cells, rectal cells, anus cells, bile duct cells, small intestine cells, stomach cells, esophageal cells, gallbladder cells, liver cells, pancreas cells, appendix cells, breast cells, ovary cells, cervix cells, prostate cells, kidney cells, glioblastoma cells, skin cells, lymphocytes, choriocarcinoma cells, head and neck cells, osteogenic sarcoma cells, blood cells, etc., or These cancer cells (cervical cancer cells, lung cancer cells, colon cancer cells, rectal cancer cells, anal cancer cells, bile duct cancer cells, small intestine cancer cells, gastric cancer cells, esophageal cancer cells, gallbladder cancer cells, liver cancer cells, pancreatic cancer cells, appendiceal cancer cells, breast cancer cells, ovarian cancer cells, prostate cancer cells, kidney cancer cells, cancer cells of the central nervous system, glioblastoma cells, skin cancer cells cancer cells, pigment cancer cells, lymphoma cells, choriocarcinoma tumor cells, head and neck cancer cells, osteogenic sarcoma cells, blood cancer cells, etc.). The cells to which The delivery carrier into cell of the present invention is delivered are particularly suitable for delivery to cells in the skin because of their intracellular delivery efficiency, antioxidant effect, tissue mobility, skin barrier permeability, and ease of inhibiting cell death after delivery.

In addition to vitamin derivatives, the delivery carrier into the cell of the present invention may also contain as an active ingredient one or more substances selected from Table 8 as an active ingredient. In addition, known active ingredients can be blended as active ingredients that can be included in the delivery carrier into the cell of the present invention, and these can be active ingredients described in known official documents and literature, for example, representative official documents and literature include, but are not limited to, the following For example, the Seventeenth Revision of the Japanese Pharmacopoeia (Tokyo, Japan) ISBN 978-4840748315, The United States Pharmacopeia and National Formulary 2018, USP41-NF36, ISBN 978-3-7692-7022-8, International Cosmetic Ingredient Dictionary and Handbook (2016) 16th EDITION (Personal Care Products Council, Washington, D.C. USA) ISBN 1-882621-55-7, List of quasi-drug additives, revised edition, Pharmaceutical Affairs Nippo-sha (Tokyo, Japan), 2017, ISBN: 978-4-8408-1492-8° C.3047, List of active ingredients in so-called quasi-drug cosmetics as described in Notification No. 1225001 of the Director of the Examination and Control Division, Pharmaceutical and Food Safety Bureau, Ministry of Health, Labour and Welfare. 2006, Pharmaceutical Affairs Nipposha (Tokyo, Japan), 2013 ISBN: 978-4-8408-1227-6 C3047, Quasi-drug Ingredients Standard: Integrated Version 2006 Addendum 2, Pharmaceutical Affairs Nipposha (Tokyo, Japan), 2018 ISBN: 978-4-8408-1464-5 C3047. The concentration of the active ingredients in the case of inclusion of these active ingredients in The delivery carrier into cell is not particularly limited and can be changed according to the concentration of the effective expression of the active ingredients and the purpose, for example, it can be selected from the range of 1 ppm to 50% by weight.

If a vitamin derivative is used in the delivery carrier into the cell of the present invention, other inclusionary active ingredients may not necessarily be present, since the effect of this vitamin derivative can be expressed. In addition, the concentration of the active ingredient is not particularly limited and can be changed according to the concentration of the active ingredient and the purpose, for example, it can be selected from 1 ppm to 50% by weight.

The dose of The delivery carrier into cell of the present invention is not particularly limited and can be appropriately changed depending on the effective expression concentration of the active ingredient and the purpose. A formulation can be obtained by adding 0.001% to 50% by weight of The delivery carrier into cell of the present invention to the agent can be applied to the skin surface area in 1 to 10 divided doses of 1 μg to 10 g/1 cm2/day.

The method of administration of the delivery carrier into the cell of the invention is not particularly limited and can be selected according to the type of cell to be targeted. For example, it may be administered topically, or orally, or by injection (intravenous, subcutaneous, or intramuscular injection, etc.).

In addition, various devices such as iontophoresis, electroporation, sound waves, ultrasound, low frequency, high frequency, heaters, various lasers, and various optical energy devices, and tools such as gauze, nonwoven fabric, paper, film, towels, mask sheets, carbonic acid generators, steam generators, and oxygen generators can also be used during administration. In addition, microneedles and mesotherapy devices can be used.

The delivery carrier into the cell of the present invention can be used for all applications where the effect can be demonstrated, but it is preferable to use them for applications selected from pharmaceuticals, quasi-drugs, cosmetics, supplements, veterinary drugs, and miscellaneous goods.

Furthermore, the formulation of the delivery carrier into the cell of the invention when used for these applications is not particularly limited, but preferably it can be selected from topical, oral, suppository, oral drink, poultice, pack, spray, injection, dressing, liquid, ointment, aerosol, powder, mold, cream, topical dispersant, dispersant, granule, tablet, soft capsule, round, plate, troche, paste, solid, moisturizing and tic-like formulations. In addition, if the application of these delivery carrier into the cell is for cosmetics or quasi-drugs, their efficacy or effect can be selected from Table 9 above, including but not limited to.

The target animal of the delivery carrier into the cell of the present invention is not particularly limited and can be applied to any organism, including humans. Examples include mice, rats, dogs, cats, monkeys, pigs, bovines, sheep, rabbits, fish, edible water animals, useful plants, and useful fungi.

In addition to known active ingredients, nucleic acids, fungi, viruses, cell, or those extract ingredient, protein and the like can be included as inclusion components of the delivery carrier into the cell of the present invention.

The vitamin derivative of the subject of the delivery carrier into the cell of the present invention must promote the activity of both autophagy-related genes and cathepsin synthesis genes.

The vitamin derivatives that are simultaneous activators of autophagy-related genes and cathepsin synthesis genes that can be used as carriers for cell delivery of the invention are shown in Table 2. They promoted the activity of both autophagy-related genes and cathepsin synthesis genes, as shown in the embodiment. In the present invention, it is necessary to include at least one or more of these vitamin derivatives in a Delivery carrier into cell. More preferably, when two or more vitamin derivatives of different types are selected from Table 2 and blended, cell adhesion is enhanced and the delivery rate of substances in the carrier can be increased.

The stimulus-responsive-polymer containing molecules that can be used in the present invention are polymers that are used in chemical and biological applications, such as drug delivery (DDS), bio-conjugation, tissue engineering, biosensors, and bioseparation, and are also referred to as smart polymers or environmentally responsive polymers, due to their properties that change with external stimuli.

A stimulus-responsive-polymer containing molecule that can be used in the present invention is a polymer containing a stimulus-responsive molecule whose microstructure changes reversibly or chemically depending on the surrounding external stimulus, such as temperature, pH, ionic strength, magnetic field, electric field, light, sound waves, pressure, solvent, acceleration, or chemical species, and all of them can be used in the present invention.

The stimulus-responsive-polymer containing molecules are classified according to their physical shape as (a) linear polymers free in solution, (b) covalently cross-linked reversible gels, (c) surface-adsorbed polymers or surface-grafted polymers reversibly bound by ionic bonds, hydrogen bonds, etc. Any of the above can be used in the present invention, but preferably the stimulus-responsive-polymer containing molecules are bound to one of the amphiphilic antioxidant vitamin derivatives or lipids, and more preferably the bonds are either covalent, ionic or hydrogen bonds. This is because the effects of molecular changes in response to external stimuli can be rapidly and directly exerted by the coupled delivery carrier into the cell.

For the molecules containing stimulus-responsive polymers used in the present invention, polymers containing molecules that respond to any one or more of the three external stimuli (temperature, pH, and light) are suitable.

In the present invention, the stimulus-responsive-polymer containing molecules may be present in the emulsion composition, preferably bound to, encapsulated in, or penetrated by the outermost membrane of the delivery carrier into the cell, and preferably some or all of the stimulus-responsive-polymer containing molecules are present in the outermost carrier of the delivery carrier into the cell. This is because when the change in responsive state is photoresponsive or pH-responsive, the stimulus is often transmitted from the outside to the inside, and it is important that the molecules with the responsive part of the sensor are in contact with the outside of the delivery carrier into the cell. In addition, this point is important because it is easiest to convey to the external environment the change in properties caused by the change in molecular shape after the stimulus response.

The form in which the stimulus-responsive-polymer containing molecule of the present invention is bound to any one of the amphiphilic antioxidant vitamin derivatives or lipids to which eight or more carbons other than the aforementioned amphiphilic antioxidant vitamin derivatives are continuously bound, it can be either the form in which the stimulus-responsive-polymer containing molecule is bound to the amphiphilic antioxidant vitamin derivative or the form in which the stimulus-responsive-polymer containing molecule is bound to the lipid, and the binding form can be either an ionic bond, a covalent bond, or a hydrogen bond.

As an example of the form in which the stimulus-responsive-polymer containing molecule of the present invention is bonded to a lipid, the stimulus-responsive-polymer containing molecule is bonded to a lipid, a fatty acid, and a lamellamellar surfactant respectively, all of which can be used in the present invention, however, the form in which the stimulus-responsive-polymer containing molecule is covalently bonded to a fatty acid and the stimulus-responsive-polymer containing molecule is covalently bonded to a lamellar surfactant is the most suitable because of its extremely high stability, simplicity of synthesis, low cost, and high yield.

As a specific example of a case in which a molecule containing a stimulus-responsive polymer is covalently bonded to a fatty acid, alkyl-polyisopropylacrylamide is known (Non-Patent Document 12), and the form in which a molecule containing a stimulus-responsive polymer is covalently bonded to a liposome is known as dioleoylphosphoethanolamine, mercaptopropionyl (isopropylacrylamide/dimethylaminopropylacrylamide) copolymer (Patent Document 7), etc. Any of these polymers can be used in the present invention.

In all of the known cases described above, when the polymer was used alone, it was ineffective in protecting the active ingredient against the attack of reactive oxygen species, etc. Especially, there was a problem that the easily oxidized active ingredient was oxidized and lost its activity in the formulation.

The temperature-stimulus-responsive-polymer containing molecules of the present invention form a hydration layer and dissolve in water at temperatures below the minimum critical dissolution temperature for water, but at temperatures above the minimum critical dissolution temperature, they become hydrophobic and the cell membrane permeability of the carrier increases.

For this reason, the lower critical dissolution temperature of the conventional temperature-stimulus-responsive-polymer containing molecules is preferred to be 37-42° C., which is close to the body temperature. However, the upper limit of the distribution temperature of most products, including medicines, foods, and cosmetics, to which the products including the present invention are applied, may be 45° C. in the summer. Therefore, when the lower limit of the critical dissolution temperature is set at 36-42° C. of body temperature, problems such as the delivery carrier into the cell binding with other hydrophobic components and separating them, or when the container is made of plastic, the active components remain in the container due to adhesion. For this reason, the minimum critical dissolution temperature of this invention is 35° C. or more. The lower critical dissolution temperature of the invention should be 35° C. to 70° C. or lower. The lower critical dissolution temperature of the invention should be 35° C. to 70° C. or lower, because irreversible burns often occur at 70° C. or higher. More preferably, the temperature should be 45° C. to 60° C. In the present invention, the lower critical dissolution temperature of the temperature-stimulus-responsive polymer in water is measured by differential scanning calorimetry (DSC).

Polyglucosamine having glucosamine as a monomer is a suitable example of a pH stimulus-responsive polymer that can be used in the present invention, and chitosan having glucosamine as a constituent unit can also be used. In addition, a polymer made of chitosan as a raw material can be used, as well as a low molecular weight chitosan cut with enzymes or an alkali-treated neutral chitosan.

Known Non-Patent Documents 13, 14, and 15 include examples of chitosan-coated liposomes in which chitosan is processed into liposomes, but the chitosan described in these references may also be used in the present invention.

When the delivery carrier into the cell containing the pH-stimulating polymer-containing molecule of the present invention is a chitosan-containing delivery carrier into the cell, the manufacturing process is as follows: The manufacturing step of reacting a chitosan aqueous solution with a delivery carrier into the cell that does not contain the chitosan of the present invention and ionizing the chitosan to the surface of the delivery carrier into the cell can be taken. The preparation of chitosan solutions usually requires dissolution in acid, and therefore, the pH must be less than or equal to 5. When this is applied to the human body, the acidity causes inflammation of the skin. In addition, under these acidic conditions, the delivery carrier into the cell are destroyed and problems such as separation and precipitation occur. Neutralization with alkali induced whiteness and separation of the solution, and the formation of neutralizing salts, such as NaCl, caused skin irritation problems. Therefore, it is preferable to use a neutral chitosan with a pH of 6-8 as the chitosan itself used in the present invention. After dissolving neutral chitosan in acids such as lactic acid, citric acid, ascorbic acid, etc., it is desirable to remove the acid by adsorption and adjust the pH to 6-8 by contacting with an anion exchange resin or mixing with chitosan derived from natural products.

The stimulus-responsive polymer that can be used for the carrier of the invention can be used as long as it is a liquid in the range of 15° C. to 70° C. and the decay rate of the vitamin derivative is suppressed to 20% or less and kept stable in an accelerated test at 40° C., 80% humidity for six months or less when used together with the vitamin derivative in Table 2. It was found that the stimulus-responsive polymer in which one or more chemical substances selected from a specific group of substances are chemically modified with covalent bonds is suitable for the stimulus-responsive polymer that satisfies these conditions, and the group of substances was identified. In other words, the present inventors have found that a stimulus-responsive polymer, in which one or more chemical substances selected from the group of substances in Table 7 are chemically modified with covalent bonds, can make a Delivery carrier into cell that can clear the stability of these conditions. In addition, the present inventors examined the stability of the carrier by inclusion of various active ingredients in The delivery carrier into cell of the present invention. This is because the stability of the delivery carrier into the cell of the present invention changes not only with the constituents of the carrier, but also with the type of inclusion components included in the carrier. As a result of the test, it was found that the material selected from Table 8 can be stably encapsulated in the carrier of the present invention even after the accelerated test under the above-mentioned conditions. By applying the delivery carrier into the cell of the present invention encompassing the active ingredients selected from Table 8 to humans, the inventors were able to confirm that the effect of Table 9 was expressed. These effects can be achieved by encapsulating the carrier with a temperature-stimulus-responsive polymer whose effective temperature of the carrier is 45 to 70° C. and artificially raising the tissue temperature at the administration site at the same time.

In addition, the present invention may include polyvalent alcohols, synthetic antioxidants, UV absorbers, and preservatives used as stabilizers in ordinary emulsion formulations, which are necessary in making the carrier. Among these substances, those which are in liquid form in the range of 15° C. to 70° C. and which can suppress the decay rate of vitamin derivatives to less than 20% and maintain a stable lamellar structure in an accelerated test at 40° C., 80% humidity, for 6 months when used together with the vitamin derivatives in Table 2, the lipids in Table 3, the lipids having a surfactant action in Table 4, and the stimulus-responsive polymers in Table 5 are the most suitable for the present invention, and screening of these substances confirmed that one or more of the ingredients selected from the emulsion stabilizers shown in Table 6 correspond to these substances.

The best form for implementing the present invention is a Delivery carrier into cell in which one or more of the substances for simultaneous activation of autophagy-related genes and cathepsin synthesis genes and stimuli-responsive polymer-containing molecules constitute part of a membrane molecule composed mainly of lipids, as shown in FIG. 2 above. Yet another best form for implementing the present invention is a delivery carrier into cell in which the stimuli-responsive polymer-containing molecule shown in FIG. 3 above is ionically bound to a lipid. Specific applications of The delivery carrier into cell s of the present invention include pharmaceuticals, quasi-pharmaceuticals, cosmetics, supplements, veterinary drugs, and miscellaneous goods. Delivery carrier into cell s selected from tablets, soft capsules, rounds, platelets, lozenges, pastes, solids, moisturizers, and stic-like preparations are more suitable as distribution dosage forms.

ATG and CTS Activity of Vitamin Derivatives

Three different vitamin derivatives with ascorbic acid-2-phosphate esters, namely, ascorbyl-3Na phosphate (APS), ascorbyl-3Na palmitate (APPS), and ascorbyl/tocopheryl-K phosphate (EPC) mixtures, were used in the following experiments: normal human epidermal fibroblasts were cultured at a density of 5x105 cell/well using DMEM (low glucose) containing 5% FBS at 37° C. for 24 hours, and then changed to medium containing mixed test samples (APS: 100 μM, APPS: 100 μM, EPC: 100 μM for a total concentration of 300 μMn) and cultured at 37° C. for 24 hours. Next, each cell was collected, RNA was protected with RNA protect cell Reagent (QIAGEN) and stored at −80° C. until analysis. after quality check of total RNA, whole transcriptome analysis was performed using 3D-Gene whole genotype DNA chip. The results were obtained for each factor from the autophagy-related gene (ATG) and cathepsin (CTS), a lysosome-localized protease, and compared with the RNA levels in the non-additive control. As for the mean values of the test samples, those with an increase of 1.2-fold or more in ATG RNA biosynthesis were marked with ◎, those with an increase of 1.2-fold or more in CTS were marked with X, and those with no increase were marked with X. The results are shown in Table 12 below.

Results of ATG and CTS Activities of Vitamin Derivatives

TABLE 12

| Gene abbreviation | Protein name | Result |
|---|---|---|
| ATG2A | autophagy related 2A | ◎ |
| ATG14 | autophagy related 14 | ◎ |
| ATG9B | autophagy related 9B | ◎ |
| ATG5 | autophagy related 5 | ◎ |
| ATG4B | autophagy related 4B cysteine peptidase | ◎ |
| ATG2A | autophagy related 2A | ◎ |
| ATG16L2 | autophagy related 16 like 2 | ◎ |
| ATG13 | autophagy related 13 | ◎ |
| ATG3 | autophagy related 3 | ◎ |
| ATG101 | autophagy related 101 | ◎ |
| AMBRA1 | autophagy/beclin-1 regulator 1 | ◎ |
| ATG7 | autophagy related 7 | ◎ |
| ATG12 | autophagy related 12 | ◎ |
| ATG4A | autophagy related 4A cysteine peptidase | ◎ |
| ATG2B | autophagy related 2B | ◎ |
| ATG2B | autophagy related 2B | X |

TABLE 12-continued

| Gene abbreviation | Protein name | Result |
|---|---|---|
| ATG9A | autophagy related 9A | X |
| ATG10 | autophagy related 10 | X |
| ATG4C | autophagy related 4C cysteine peptidase | X |
| ATG16L1 | autophagy related 16 like 1 | X |
| CTSK | cathepsin K | ◇ |
| CTSE | cathepsin E | ◇ |
| CTSF | cathepsin F | ◇ |
| CTSH | cathepsin H | ◇ |
| CTSS | cathepsin S | ◇ |
| CTSL | cathepsin L | ◇ |
| CTSV | cathepsin V | ◇ |
| CTSW | cathepsin W | ◇ |
| CTSD | cathepsin D | ◇ |
| CTSB | cathepsin B | ◇ |
| CTSG | cathepsin G | ◇ |
| CTSZ | cathepsin Z | ◇ |
| CTSLP6 | cathepsin L pseudogene 6 | ◇ |
| CTSD | cathepsin D | X |
| CTSO | cathepsin O | X |
| CTSC | cathepsin C | X |

Test 2

The same experiment was performed on 84 vitamin derivatives described below, and the same evaluation as above was performed, and ○ was assigned to those in which 1 or more of each of ◎ and ◇ was present and the total of them was 10 or more, Δ was assigned to those in which 1 or more of each of ◎ and ◇ was present and the total of them was 5 or more, and X was assigned to the other. Note that X includes those whose sample volume did not reach the specified volume for this test. As a result, there were 53 samples of vitamin derivatives corresponding to X and Δ that could be used in the present invention, and 32 samples of X were unknown. The comparison of the three derivatives having ascorbic acid-2-phosphate ester in the structure used in the comparative experiments of the present invention shows that ascorbic acid (AA) and ascorbyl-3Na phosphate (APS) are X, ascorbyl-3Na palmitate (APPS) is Δ, and (ascorbyl/tocopheryl)-phosphate K (EPC) is ○. For ATG and CTS activity, from the higher activity, EPC>APPS>APS and AA.

Results of the ATG and CTS Activities of 84 Vitamin Derivatives (Ascorbyl/tocopheryl)phosphate K: ○, (ascorbic acid/PCA) Mg: X, (linoleic acid/oleic acid) tocopherol: X, ethyl 2,4-dicarboethoxypantothenate: ○, 3-O-ethyl ascorbic acid: ○, 3-O-cetyl ascorbic acid: ○, 3-ascorbyl carbonyl dipeptide-17: Δ, ascorbyl ethyl: ○, ascorbyl methylsilanol pectin: ○, ascorbic acid (orange/lemon/lime) polypeptide: X, ascorbic acid allantoin: X, ascorbic acid glyceryl diester tocopherol: ○, ascorbic acid diester tocopherol: ○, tetrahexyldecyl ascorbic acid: ○, ascorbic acid polypeptide: Δ, ascorbic acid methylsilanol: Δ, acetylpantothenyethyl: X, allantoinpantothenyl alcohol: X, isostearyl Ascorbyl phosphate 2 Na: ○, ascorbyl isostearate: ○, ascorbyl palmitate 3Na: Δ, caprylyl 2-glyceryl ascorbic acid: ○, caprylyl 3-glyceryl ascorbic acid: ○, glycyrrhetinic acid pyridoxine: X, tocopherol succinate: ○, succinoyltri Peptide-34 Copper ascorbyl phosphate: X, Succinoyl pentapeptide-12 Ascorbyl phosphate: X, Diethyl ascorbate: ○, Dioleyl tocopherylmethylsilanol: ○, DiCaprylyl pyridoxine: ○, Ethyl dicarboethoxypantothenate: ○, Pyridoxine dipalmitate: ○, Ascorbyl stearate: Δ, Diacetylresveratryl thioctoate: X, Stearate thioctoate: ○, Palmitate thioctoate: ○, Margarate thioctoate: ○, Thioc Methoxy PEG-45 toxate: X, Ascorbyl tetrahexyl decanoate: ○, Riboflavin tetrabutyrate: ○, Ethyldimonium ethosuccinate dimonium ethosulfate: X, Tocopheryloxypropyltrisiloxane: ○, Tocopheryl glucoside: ○, Tocopheryl dimethyl glycine: ○, Tocopheryl dimethyl glycine HCl: ○, Tocopheryl phosphate Na: ○, Tocofersoran: ○, Tocopheryl tranexamate HCL: X, Trihexyldecanoic acid pyridoxine: ○, Tripalmitic acid pyridoxine: X, Tocopherol nicotinate: ○, Ascorbyl palmitate: X, Ascorbyl hyaluronate: X, Ascorbyl propyl hyaluronate: ○, Bis (hydroxyethyl tocopheryl succinoylamide) Hydroxypropane: X, Bislaurylsulfate thiamine: X, Hydroxydecylubiquinone: Δ, Hydroxypropyltrimonium ascorbic acid: X, Retinol propionate: ○, Ascorbyltocopheryl maleate: ○, Thioctamidoethyldimethylamine maleate: X, Ubiquinol: X, ubiquinone: X, ubiquinone 2Na: X, laurimino dipropionate tocopheryl phosphate 2Na: A, linoleic acid tocopherol: ○, linoleic acid retinol: ○, ascorbyl phosphate 3Na: X, ascorbyl phosphate Mg: X, Ascorbyl aminopropyl phosphate: X, Tocopheryl aminopropyl phosphate: X, Tocopherol phosphate 2Na: ○, Tocopheryl retinoate: ○, Hydroxypinacolone retinoate: X, Retinoin Retinyl: ○, Retinol: X, Retinoxytrimethylsilane: X, Pantothenylethyl benzoate: X, Tocopherol acetate: ○, Retinol acetate: ○, Retinol palmitate: Δ, (Ascorbyl/cholesteryl) sodium phosphate: ○, (Linoleic acid/oleic acid) tocopherol: ○, ascorbic acid: X, ascorbic acid glucoside: Δ, non-added control: X.

Stability Test

APS, APPS, and EPC so that the concentration of each ascorbate derivative is 0.02 mol/L. Dissolve them in purified water and store them at 50° C. for one month to determine their potency in a high performance liquid The starting titers of each substance were measured by chromatography, and the results after one month were used as the starting titer of 100%. If more than 95% of the result was remaining in the material, it is ○, and if less than 95% or more than 80% of the result was less than 95%, it is ○. Table 13 below shows the results with a negative value for those that remained and an X for those that were less than 80%. Sodium ascorbic acid-2-phosphate: APS; Sodium ascorbic acid-2-phosphate-6-palmitate 3: APPS; Potassium tocopheryl ascorbic acid-2-phosphate: EPC; ascorbic acid: AA.

Stability Test Results

TABLE 13

| Test substance name | Remaining rate | Evaluation results |
|---|---|---|
| EPC | 96% | ○ |
| APS | 91% | Δ |
| APPS | 78% | x |
| AA | 56% | x |

From the above results, the physical stability was determined to be EPC>APS>APPS>AA from the higher stability. It was found that ATG and CTS activities did not correlate with physical stability, because ATG and CTS activities detected EPC>APPS>APS and AA from the higher activity.

Surfactant Force Test

The ascorbic acid derivatives of APS, APPS, EPC, and AA were dissolved in purified water at a concentration of 0.5% by weight, and the time to defoam the bubbles was measured with a sponge under the same conditions. The results are shown in Table 14, where the defoaming time of the APPS with the longest defoaming time was set to 100% and the defoaming time of each was calculated as a percentage, with 90% or more being considered O (best), 80% or more to 90% or less being considered B (good), and 80% or less being considered X (poor). Description of abbreviations: ascorbic acid-2-phosphateNa:APS, ascorbic acid-2-phosphate-6-palmitate3Na:APPS, ascorbic acid-2-tocopheryl potassium:EPC, ascorbic acid:AA.

Surfactant Force Test

TABLE 14

| Test substance name | Remaining rate | Evaluation results |
|---|---|---|
| APPS | 100% | ○ |
| EPC | 85% | Δ |
| APS | 3% | x |
| AA | 1% | x |

From the above results, the surface activity obtained from the defoaming time in the aqueous solution was APPS>EPC APS>AA from the highest. As for ATG and CTS activity, it was found that ATG and CTS activity did not correlate with surfactant activity, because ATG and CTS activities detected EPC>APPS>APS and AA from the higher activity.

The following experiments show that ATG and CTS activities are correlated with cell delivery rate.

A Comparison Experiment with the Present Invention

The total amount of the next lipid was 20 mg, the molar ratio of (lipid 1,2-diore oil-3-trimethylammonium propane): (total weight of lamella-forming surfactant diore oil phosphatidylethanolamine and DOPEMP (NIPAA/DMAPAA 5%) Cop) was 3:7. Each was dissolved in chloroform. Further, the fluorescent dye Rhodamine B (1 mg) was added and dissolved. The lower limit critical dissolution temperature of DOPEMP (NIPAA/DMAPAA 5%) Cop used in this experiment in water was 40° C. The molar ratio of (dioleoylphosphatidylethanolamine: DOPEMP (NIPAA/DMAPAA) Cop.) added by total weight was 6.5:0.5.

The solution was transferred to an eggplant flask and the solvent was blown off by an evaporator to prepare a lipid film. EPC, APPS, APS and AA (ascorbic acid), which are three types of Vitamin derivatives having different ATG activity and CTS activity (hereinafter abbreviated as ATG-CTS activity), were prepared. To this lipid film, EPC, APPS, APS and AA (5 mg each) dissolved in PBS (1 ml) were added. The lipid film was hydrated and then dispersed by vortexing. After that, sonication was performed for 30 minutes in an ultrasonic bath to reduce the size of the liposome, and then the liposome was passed through a 200 nm filter using an extruder to adjust the size of the liposome. The average particle size of the examples and comparative examples was 111 nm±10 nm. Then, the liposomes were separated and purified by gel filtration. By the above method, a Delivery carrier into cell of the present invention containing an ATG-CTS activator, a temperature-responsive polymer and a hydrocarbon was prepared. When these delivery carriers into cell were observed with a transmission electron microscope by the staining method, a multilayer vesicle structure (lamella liquid crystal structure) was confirmed, and it was confirmed that these delivery carriers into cell had a lamella liquid crystal structure.

Next, normal human epidermal fibroblasts were cultured in DMEM (low glucose) containing 5% FBS for 24 hours at 37° C. at a density of 5×105 cell/well in 6-well plates, and then the medium containing four delivery carrier into the cell (added to achieve a final rhodamine concentration of 1 μM), including the embodiments and comparative examples prepared as described above, was exchanged for each medium and cultured at 35° C. for 1 hour. After that, it was incubated at 40° C. for 20 min, and then at 35° C. for 1 h. It was then washed five times with PBS and immobilized with 4% paraformaldehyde phosphate buffer solution for 20 min, washed twice with PBS again, and the relative concentration of the fluorescent material taken up into the cell was determined by measuring the fluorescence intensity with a fluorescent microplate reader. cell of delivery carrier into the cell without vitamin derivatives were also cultured in the same way as additive-free controls and the fluorescence intensity was measured.

As a result, when the fluorescence intensity of the EPC-added groups was set to 100%, it was 78% for APPS, 49% for APS, and 52% for AA. Therefore, the cell absorption rate was EPC>APPS>APS, AA from the highest, and the ATG and CTS activities were EPC>APPS>APS, AA from the highest activity. From this, it was found that the cell absorption rate and the ATG-CTS activity correlate with each other.

The present inventors found that the reason why the vitamin derivatives enhanced ATG and CTS activity was completely unrelated to the stability and surfactant power of the vitamin derivatives, and speculated the reason as follows. That is, vitamins are important nutrients for human cell in the first stage, and their intracellular concentration is higher than that of blood. Therefore, it is thought that vitamins attach to some kind of vitamin receptors on the cell surface in the first stage and are actively transported by specific channel proteins in the second stage. We thought that stable vitamin derivatives could adhere to vitamin receptors, but could not be actively transported by specific channel proteins or other means in the second step.

That is, the vitamin receptor on the cell surface recognizes a part of the vitamin molecule and adheres only to that part, but in the second stage specific channel protein, most of the vitamin derivatives are not actively transported to the cell. I thought it would stick to the surface and stay. We thought that a vitamin derivatives are considered to be taken up into cell while bound to cell membrane receptors by a type of endocytosis, pinocytosis, and it forms vesicles (endosomes) .acellular fluid.

Vitamin receptors bound to the vitamin derivatives are thought to be recovered and degraded by endosomes to regenerate new vitamin receptors. Endosomes activate CTS to form lysosomes that fuse with them to digest vitamin derivatives in vesicles. Some vitamin derivatives are thought to be released intracellularly without being degraded. The cell recognize these as foreign substances and are recognized by some system in the autophagy system. It is thought that the ATG gene is activated to form autophagosomes, and in addition, CTS is activated to form lysosomes. These will degrade vitamin derivatives in the vesicles. In this way, the vitamin derivatives taken up into the cell will eventually become reusable materials for the cell. Therefore, by using the ATG-CTS-active vitamin derivatives as the carrier for delivery to cell of the present invention, the adhesive force of the carrier for delivery to cell can be enhanced, and I thought the efficiency of carrier uptake into cell can be improved and dramatically increased.

In the following experiments, we investigated whether the addition of vitamin derivatives with different ATG and CTS activities to the delivery carrier into the cell altered their uptake into the cell. Based on the results of the above-mentioned experiments, ATG and CTS activities were found to be X for ascorbyl palmitate (PA), Δ for isopalmitate ascorbyl phosphate 3 Na (APPS), and ○ for (ascorbyl/tocopheryl)phosphate K (EPC).

Create a Delivery carrier into cell in a comparison experiment To investigate the effects of vitamin derivatives with different ATG-CTS activities on cell uptake, the following experiments were performed on delivery carrier into the cell without stimulus-responsive polymers. Six g of glycerin, 1 g of sodium cocoyl glutamate, and 1 g each of three vitamin derivatives (PA, APPS, and EPC) with different ATG-CTS activities were mixed with an electric hand mixer, and 0.1 g of rhodamine B, a fluorescent dye, was added to 20 g of jojoba oil and stirred for 20 minutes. To this, PBS was added to 100 g and stirred for 10 minutes with an electric hand mixer to prevent foaming. 3 types of cell carriers were obtained by completely dispersing them. A Delivery carrier into cell of vitamin derivative-free was also created using the same method as an additive-free control.

Normal human epidermal fibroblasts were incubated in DMEM (low glucose) containing 5% FBS at a density of 5×105 cell/well at 37° C. for 24 hours in 6-well plates, and then the medium containing the three delivery carrier into the cell of the invention (final concentration of PA, APPS, and EPC was added to 200 μM each) was replaced with the medium prepared as described above and incubated at 37° C. for 1 hour. Then, the cell were washed five times with PBS and immobilized with 4% paraformaldehyde phosphate buffer solution for 20 min, washed twice with PBS again, and the relative concentration of the fluorescent material taken up into the cell was determined by measuring the fluorescence intensity at the excitation wavelength of 555 (nm) and the fluorescence wavelength of 580 (nm) with a fluorescent microplate reader. cell of delivery carrier into the cell without vitamin derivatives were also cultured in the same way as additive-free controls and the fluorescence intensity was measured.

As a result, when the fluorescence intensity of EPC was set at 100%, that of APPS was 76%, that of PA was 58%, and that of The delivery carrier into cell without the vitamin derivative was 45%. The ATG and CTS activities of the three vitamin derivatives were EPC>APPS>PA, from the largest to the smallest, and the uptake rate of the fluorescent substances conjugated with The delivery carrier into cell was also EPC>APPS>PA, from the largest to the smallest, and the uptake rate of the vitamin derivatives into the cells of The delivery carrier into cell was proportional to the magnitude of the ATG and CTS activities.

Synthesis of Stimulus-Responsive Polymer Step 1-01 (Temperature

The molar ratio of N-isopropylacrylamide, the first stimulus-responsive monomer, and methylaminopropylacrylamide, the second stimulus-responsive monomer (temperature), was made to be 95%:5%. The total amount of monomer was set to 10 g. After dissolution, 3-mercaptopropionic acid was added by 0.03 ml of N-isopropylacrylamide, and 60 mg of azobisisobutyronitrile was added. After nitrogen substitution in the solvent and deaeration by ultrasound, radical polymerization was carried out at 70° C. for 6 hours. The temperature of the post-reaction liquid was brought back to room temperature and then dripped into pre-chilled diethyl ether for recalcification. Subsequently, the precipitates were recovered by filtration. This reprecipitation process was carried out two more times to recover the polymer. This polymer was dialyzed with water and then lyophilized to obtain a (temperature) stimulus-responsive polymer, mercaptopropionic acid (isopropylacrylamide/dimethylaminopropylacrylamide 5%) copolymer. The molecular weight of this temperature-stimulated polymer was 5500, and the lower critical dissolution temperature in water was 40° C.

Synthesis of Stimulus-Responsive Polymer-Bound Lipids

The molar ratio of the stimulus-responsive polymer made above, mercaptopropionic acid (Isopropylacrylamide/Dimethylaminopropylacrylamide 5%) copolymer: N,N'-dicyclohexylcarbodiimide: N-hydroxysuccinimide=1:2.5:2.5 The mixture was dissolved in methyl chloride in a ratio of 0.1 to 0.1 and allowed to react at room temperature for 24 h. The reaction was followed by removal of dicyclohexyl urea as a by-product by suction filtration. After the reaction, dicyclohexyl urea as a by-product was removed by suction filtration, and the reaction was followed by the use of diethyl ether to remove the Re-sedimentation was carried out and the precipitate was found to be N-succinimidylmercapto propionic acid (Isopropylacrylamide/Dimethylaminopropylacrylamide 5%) copolymer (5%) (MPA stimulus-responsive polymers) were recovered.

The N-succinimidyl mercaptopropionic acid (isopropylacrylamide/dimethylaminopropylacrylamide 5%) copolymer prepared above and 1,2-dioreoil-sn-glycero-3-phosphoethanolamine (lamella-forming surfactant), which is a lipid having an ethanolamine group, was dissolved in dioxane at a molar ratio of 1:1. And those was reacted at room temperature for 24 hours. Dioleoylephosphatidylethanolamine mercaptopropionyl (isopropylacrylamide/dimethylaminopropylacrylamide 5%) copolymer, a temperature-stimulus-responsive polymer-binding lipid as indicated by chemical formula 1 below, was prepared by vacuuming the post-reaction solution in an evaporator and skipping the solvent. This temperature-stimulus-responsive polymer-bound lipid is abbreviated to DOPEMP (NIPAA/DMAPAA 5%) Cop. In the following, DOPEMP (NIPAA/DMAPAA 5%) Cop is sometimes referred to as DOPEMP (NIPAA/DMAPAA)-Cop. Further below, DOPEMP (NIPAA/DMAPAA) Cop is sometimes used as an abbreviation for the dioleoylphosphatidylethanolamine mercaptopropionyl (isopropylacrylamide/dimethylaminopropylacrylamide) copolymer.

[Chemical formula 1]

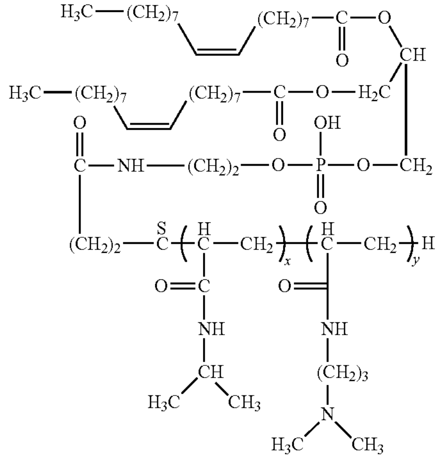

Chemical formula 1 is the chemical formula for a dioleoylphosphatidylethanolamine mercaptopropionyl (isopropylacrylamide/dimethylaminopropylacrylamide) copolymer that can be used in the present invention. The abbreviated name is indicated below as DOPEMP (NIPAA/DMAPAA) Cop.

By replacing N-isopropylacrylamide, the first monomer in the above example, with another first monomer listed in Table 15 below, a lipid-bound thermo-stimuli-responsive polymer could be produced by the same method as above. By the way, the use of a second monomer is described in the above process, and the second monomer could be selected from the same group of first monomers, a substance different from the first monomer used. Furthermore, this second monomer does not have to be added, and in that case, the blending ratio can be increased by increasing the amount of the first monomer to the extent that the second monomer is reduced. The results of the aforementioned manufacturing process and stability test at 40° C., 80% humidity, for 6 months showed that the temperature-responsive first monomers with a decomposition rate of 10% or less can be used in the present invention, as shown in Table 15.

TABLE 15

| |
|---|
| (Polyoxyethylene octyl phenyl ether) acrylate, (polyoxy ethylene octyl phenyl ether) methacrylate, (polyoxy ethylene nonyl phenyl ether) acrylate, (polyoxy ethylene nonyl phenyl ether) methacrylate, (polyoxy ethylene lauryl ether) acrylate, (Polyoxyethylene lauryl ether) methacrylate, 1,2,4,5-tetrakis (N,N-dithiocarbamylmethyl) benzene, 1,3,5-tri (bromomethyl) benzene, 2-n-propyl-2-oxazoline, 2-N,N-dimethylaminoethyl acrylate, 2-N,N-dimethylaminoethyl methacrylate DMAEMA, 2-amino-2-hydroxymethyl-1,3-propanediol 2-amino-2-hydroxymethyl-1,3-propanediol (Tris), 2-amino-2-hydroxymethyl-1,3-propanediol, 2-hydroxy-3-phenoxypropyl acrylate, 2-hydroxybutyl acrylate, 2-hydroxybutyl methacrylate, 2-hydroxypropyl acrylate, 2-hydroxypropyl methacrylate, 3,5-tri (N,N-dithiocarbamylmethyl) benzene, 3-N,N-dimethylaminopropylacrylamide, N-acryloyl Asparaginamide, N-acryloylglycinamide, N-acryloylglutamineamide, N-acetylacrylamide, N-methylacryloylasparaginamide, N,N-dimethylmethacrylamide, N,N-dimethylacrylamide N,N-methylenebisacrylamide, N,N-ethylmethylacrylamide, N, N-ethylmethylamide, N,N-ethylmethylmethacrylamide, N,N-dialkyl-dithiocarbamylmethyl, N,N-dialkylacrylamide N,N-diethylacrylamide, N,N-diethylamide, N,N-diethylmethacrylamide, N,N-dithiocarbamic acid, N,N-dithiocarbamate, N,N-dimethylacrylamide, N,N-dimethyl Methacrylamide, N,N-propylacrylamide {, N,N-propylmethacrylamide}, N-acryloylpiperidine, N-acryloylmorpholine, N-alkylacrylamide, N-alkylmethacrylamide, N-alkylsubstituted acrylamide, N Alkyl-substituted methacrylamide, N-allenylphthalimide, N-isopropylacrylamide, N-isopropylamide, N-isopropylbuta-2,3-dienamide, N-isopropylmethacrylamide, N-ethylacrylamide, N-ethylmethacrylamide, N-Ethoxyethylacrylamide, N-ethoxyethylamide, N-ethoxyethylmethacrylamide, N-cyclopropylacrylamide N-cyclopropylamide, N-cyclopropylmethacrylamide, N-tetrahydrofurfurylacrylamide, N-tetrahydrofurfuryl methacryl Amide, N-biotinyl-N'-methacrylyl trimethyleneamide, N-vinylacrylamide, N-vinylalkylacrylamide N-vinylmeth Acrylamide, N-propylacrylamide, N-methacryloylpiperidine, N- or N,N-dialkyl-substituted methacrylamide, s-butylacrylamide, t-butylacrylamide, acroylglycinamide, acroylsarcosineamide, acroylnipecotamide, Acroylmethyluracil, acetylacrylamide, isopropylacrylamide, ethylisopropylacrylamide, ethylene glycol, ethylene glycol allenyl methyl ether, oxyethylene acrylate, oxyethylene sorbitan laurate, oxyethylene methacrylate, oxyethylene laurylamine, Oligoethylene glycol acrylate, diisopropylacrylamide, diethylacrylic Amide, diethylaminoacrylate, diethylaminomethacrylate, diethyleneglycolallenylmethylether, dibutylacrylamide, |

TABLE 15-continued

| |
|---|
| dipropylacrylamide, dimethylacrylamide, dimethylaminoacrylamide, dimethylaminoacrylate, dimethylaminopropylacrylamide, dimethylaminopropylmethacrylamide, dimethylaminomethacrylamide, dimethyl Amino methacrylate, sodium N,N-dithiocarbamate, propylene glycol, hexakis (N,N-dithiocarbamylmethyl) benzene, hexakis (bromomethyl) benzene, methylacrylamide |

In the following, mercaptopropionic acid may be abbreviated as MPA. After being manufactured in the above Examples, the substances having a decomposition rate of 10% or less as a result of the above-mentioned manufacturing process and stability test (40° C., humidity 80%, 6 months) are shown in Table 16.

TABLE 16

| |
|---|
| MPA ((polyoxyethylene octyl phenyl ether) acrylate/dimethylaminopropyl acrylamide) copolymer, MPA ((polyoxyethylene octyl phenyl ether) methacrylate/dimethylaminopropyl acrylamide) copolymer, MPA ((polyoxyethylene nonyl phenyl ether) acrylate/Dimethylaminopropylacrylamide) copolymer, MPA ((polyoxyethylene nonylphenyl ether) methacrylate/dimethylaminopropylacrylamide) copolymer, MPA ((polyoxyethylene lauryl ether) acrylate/dimethylaminopropylacrylamide) copolymer, MPA ((polyoxyethylene Lauryl ether) methacrylate/dimethylaminopropylacrylamide) copolymer, MPA (1,2,4,5-Tranakis (N,N-dithiocarbamylmethyl) benzene/dimethylaminopropylacrylamide) copolymer, MPA (1,3,5-tri (bromomethyl) benzene/dimethylaminopropylacrylamide) copolymer, MPA (2-n-propyl-2)-Oxazoline/dimethylaminopropyl acrylamide) copolymer, MPA (2-N,N-dimethylaminoethyl acrylate/dimethylaminopropyl acrylamide) copolymer, MPA (2-N,N-dimethylaminoethyl methacrylate DMAEMA/dimethylaminopropyl acrylamide) copolymer, MPA (2-amino-2-hydroxymethyl-1,3-propanediol/dimethylaminopropylacrylamide) copolymer, MPA (2-amino-2-hydroxymethyl-1,3-propanediol (tris)/di Methylaminopropylacrylamide) copolymer, MPA (2-amino-2-hydroxymethyl-1,3-propanediol/dimethylaminopropylacrylamide) copolymer, MPA (2-hydroxy-3-phenoxypropylacrylate/dimethylaminopropylacrylamide) copolymer, MPA (2-hydroxybutyl acrylate/ dimethylaminopropyl acrylamide) copolymer, MPA (2-hydroxybutyl methacrylate/dimethylaminopropyl acrylamide) copolymer, MPA (2-hydroxypropyl acrylate/dimethylaminopropyl acrylamide) copolymer, MPA (2-Hydroxypropyl methacrylate/dimethylaminopropylacrylamide) copolymer, MPA (3,5-tri (N,N-dithiocarbamylmethyl) benzene/dimethyl) Aminopropylacrylamide) copolymer, MPA (3-N,N-dimethylaminopropylacrylamide/dimethylaminopropylacrylamide) copolymer, MPA (N-acryloylasparaginamide/ dimethylaminopropylacrylamide) copolymer, MPA (N-acryloylglycinamide/dimethyl) Aminopropylacrylamide) copolymer, MPA (N-acryloylglutamineamide/dimethylaminopropylacrylamide) copolymer, MPA (N-acetylacrylamide/dimethylaminopropylacrylamide) copolymer, MPA (N-methylacryloylasparaginamide/ dimethylaminopropylacrylamide) copolymer, MPA (N,N-dimethylmethacrylamide/ dimethylaminopropylacrylamide) copolymer, MPA (N,N-dimethylacrylamide/Methylaminopropylacrylamide) copolymer, MPA (N,N-methylenebisacrylamide/dimethylaminopropylacrylamide) copolymer, MPA (N,N-ethylmethylacrylamide/dimethylaminopropylacrylamide) copolymer, MPA (N,N-ethylmethylamide)/ Dimethylaminopropylacrylamide) copolymer, MPA (N,N-ethylmethylmethacrylamide/ dimethylaminopropylacrylamide) copolymer, MPA (N,N-dialkyl-dithiocarbamylmethyl/ dimethylaminopropylacrylamide) copolymer, MPA (N,N-dialkylacrylamide/dimethylaminopropylacrylamide) copolymer, MPA (N,N-diethylacrylamide/dimethylaminopropylacrylamide) copolymer, MPA (N,N-diethylacrylamide)/Dimethylaminopropylacrylamide) copolymer, MPA (N,N-diethylmethacrylamide/ dimethylaminopropylacrylamide) copolymer, MPA (N,N-dithiocarbamic acid/dimethylaminopropylacrylamide) copolymer, MPA (N,N-Dithiocarbamate/dimethylaminopropylacrylamide) copolymer, MPA (N,N-dimethylacrylamide/dimethylaminopropylacrylamide) copolymer, MPA (N,N-dimethylmethacrylamide/ dimethylaminopropylacrylamide) copolymer, MPA (N,N-propyl) Acrylamide/dimethylaminopropylacrylamide) copolymer, MPA (N,N-propylmethacrylamide/dimethylaminopropylacrylamide) copolymer, MPA (N-acryloylpiperidine/dimethylamido) Propylacrylamide) copolymer, MPA (N-acryloylmorpholine/ dimethylaminopropylacrylamide) copolymer, MPA (N-alkylacrylamide/dimethylaminopropylacrylamide) copolymer, MPA (N-alkylmethacrylamide/dimethylaminopropylacrylamide) copolymer, MPA (N-alkyl substituted acrylamide/dimethylaminopropyl acrylamide) copolymer, MPA (N-alkyl substituted methacrylamide/ dimethylaminopropyl acrylamide) copolymer, MPA (N-allenylphthalimide/dimethylaminopropyl acrylamide) copolymer, MPA (N-isopropylacrylamide)/Dimethylaminopropylacrylamide) copolymer, MPA (N-isopropylamide/ dimethylaminopropylacrylamide) copoly-, MPA (N-isopropylbuta-2,3-dienamide/dimethylaminopropylacrylamide) copolymer, MPA (N-isopropylmethacrylamide/dimethylaminopropylacrylamide) copolymer, MPA (N-ethylacrylamide/dimethylaminopropylacrylamide) copolymer, MPA (N-ethylmethacrylamide/ dimethylaminopropylacrylamide) copolymer, MPA (N-ethoxyethylacrylamide/dimethylaminopropylacrylamide) copolymer, MPA (N-ethoxyethylamide/dimethylaminopropylacrylamide) copolymer, MPA (N-Ethoxyethyl methacrylamide/dimethylaminopropylacrylamide) copolymer, MPA (N-cyclopropylacrylamide/ dimethylaminopropylacrylamide) copolymer, MPA (N-cyclopropylamide/dimethylaminopropylacrylamide) copolymer, MPA (N-cyclopropylmethacrylamide/dimethylaminopropylacrylamide) copolymer, MPA (N-tetrahydrofurfurylacrylamide/dimethylaminopropylacrylamide) copolymer, MPA (N-Tetrahydrofurfuryl methacrylamide/dimethylaminopropyl acrylamide) copolymer, MPA (N-biotinyl-N'-methacryloyl trimethylene amide/dimethylaminopropyl acrylamide) copolymer, MPA (N-vinyl acrylamide/dimethylaminopropyl acrylamide) copolymer, MPA (N-vinyl alkyl acrylamide/dimethylaminopropyl acrylamide) copolymer, MPA (N-vinyl methacrylamide/dimethylaminopropyl amide) Rylamide) copolymer, MPA (N-propylacrylamide/ dimethylaminopropylacrylamide) copolymer, MPA (N-methacryloylpiperidine/dimethylaminopropylacrylamide) copolymer, MPA (N-dialkylmethacrylamide/dimethylaminopropylacrylamide) copolymer, MPA (s-Butylacrylamide/ dimethylaminopropylacrylamide) copolymer, MPA (t-butylacrylamide/dimethylaminopropylacrylamide) copolymer, MPA (acroylglycinamide/dimethylaminopropylacrylamide) copolymer, MPA (acroylsarcosinamide/ dimethylaminopropyl) Acrylamide) copolymer, MPA (Acroyl nipecotamide/dimethylaminopropyl acrylamide) copolymer, MPA (Acroyl methyl urea) Sil/dimethylaminopropylacrylamide) copolymer, MPA (acetylacrylamide/ dimethylaminopropylacrylamide) copolymer, MPA (isopropylacrylamide/dimethylaminopropylacrylamide) copolymer, MPA (ethylisopropylacrylamide/dimethylaminopropylacrylamide) copolymer, MPA (ethylene glycol)/ Dimethylaminopropyl acrylamide) copolymer, MPA (ethylene glycol allenyl methyl ether/dimethylaminopropyl acrylamide) copolymer, MPA (oxyethylene acrylate/dimethylaminopropyl acrylamide) copolymer, MPA (oxyethylene sorbitan laurate/dimethylaminopropyl) Acrylamide) copolymer, MPA (oxyethylene methacrylate/dimester) LMP, |

TABLE 16-continued

MPA (oxyethylene laurylamine/dimethylaminopropyl acrylamide) copolymer, MPA (oligoethylene glycol acrylate/
dimethylaminopropyl acrylamide) copolymer, MPA (diisopropyl acrylamide/dimethylaminopropyl acrylamide)
copolymer, MPA (Diethylacrylamide/dimethylaminopropylacrylamide) copolymer, MPA (diethylaminoacrylate/
dimethylaminopropylacrylamide) copolymer, MPA (diethylaminomethacrylate/dimethylaminopropylacrylamide)
copolymer, MPA (diethylene glycol allenyl methyl ether/dimethylaminopropyl acrylamide) copolymer, MPA
(dibutylacrylamide/dimethylaminop Propylacrylamide) copolymer, MPA (dipropylacrylamide/
dimethylaminopropylacrylamide) copolymer, MPA (dimethylacrylamide/dimethylaminopropylacrylamide)
copolymer, MPA (dimethylaminoacrylamide/dimethylaminopropylacrylamide) copolymer, MPA
(dimethylaminoacrylate/Dimethylaminopropylacrylamide) copolymer, MPA (dimethylaminopropylacrylamide/
dimethylaminopropylacrylamide) copolymer, MPA (dimethylaminopropylmethacrylamide/
dimethylaminopropylacrylamide) copolymer, MPA (dimethylaminomethacrylamide/
dimethylaminopropylacrylamide) copolymer, MPA (dimethylaminomethacrylate/dimethylaminopropylacrylic acid)
Copolymer), MPA (sodium N,N-dithiocarbamate/dimethylaminopropylacrylamide) copolymer, MPA (propylene
glycol/dimethylaminopropylacrylamide) copolymer, MPA (hexakis (N,N-dithiocarbamylmethyl) benzene/
dimethylamino) Propylacrylamide) copolymer, MPA (hexakis (bromomethyl) benzene/
dimethylaminopropylacrylamide) copolymer, MPA (methylacrylamide/dimethylaminopropylacrylamide) copolymer Further, Table 17 shows the stimulus-responsive polymer-bound lipids that can be used in the present invention in which the decomposition rate as a result of the above-mentioned manufacturing process and the stability test at 40° C., humidity 80% and 6 months is 10% or less. Dioleoyleophosphatidylethanolamine mercaptopropionyl is hereinafter referred to as DOPEAMP. Further, we abbreviate dimethylaminopropyl acrylamide as DMAPAA.

TABLE 17

DOPEAMP ((polyoxyethylene octylphenyl ether) acrylate/dimethylaminopropyl acrylamide) copolymer, DOPEAMP
((polyoxyethylene octyl phenyl ether) methacrylate/dimethylaminopropyl acrylamide) copolymer, DOPEAMP
((polyoxyethylene nonyl phenyl ether) acrylate/Dimethylaminopropyl acrylamide) copolymer, DOPEAMP
((polyoxyethylene nonylphenyl ether) methacrylate/dimethylaminopropyl acrylamide) copolymer, DOPEAMP
((polyoxyethylene lauryl ether) acrylate/dimethylaminopropyl acrylamide) copolymer, DOPEAMP
((polyoxyethylene Lauryl ether) methacrylate/dimethylaminopropylacrylamide) copolymer, DOPEAMP (1,2,4,5-
tetrakis (N,N-dithiocarbamylmethyl) benzene/dimethylaminopropylacrylamide) copolymer, DOPEAMP (1,3,5-tri
(bromomethyl) benzene/dimethylaminopropylacrylamide) copolymer, DOPEAMP (2-n-propyl-2-oxazoline/
dimethylaminopropyl acrylamide) copolymer, DOPEAMP (2-N,N-dimethylaminoethyl acrylate/
dimethylaminopropyl acrylamide) copolymer, DOPEAMP (2-N,N-dimethylaminoethyl) Methacrylate DMAEMA/
dimethylaminopropylacrylamide) copolymer, DOPEAMP (2-amino-2-hydroxymethyl-1,3-propanediol/
dimethylaminopropylacrylamide) copolymer, DOPEAMP (2-amino-2-hydroxymethyl-l), 3-propanediol (tris)/
dimethylaminopropylacrylamide) copolymer, DOPEAMP (2-amino-2-hydroxymethyl-1,3-propanediol/
dimethylaminopropylacrylamide) copolymer, DOPEAMP (2-hydroxy-3-phenoxy) Propyl acrylate/
dimethylaminopropyl acrylamide) copolymer, DOPEAMP (2-hydroxybutyl acrylate/dimethylaminopropyl
acrylamide) copolymer, DOPEAMP (2-hydroxybutyl methacrylate/dimethylaminopropyl acrylamide) copolymer,
DOPEAMP (2-hydroxypropyl acrylate/dimethylamino) Propylacrylamide) copolymer, DOPEAMP (2-
hydroxypropyl methacrylate/dimethylaminopropylacrylamide) copolymer, DOPEAMP (3,5-Tri (N,N-
dithiocarbamylmethyl) benzene/dimethylaminopropylacrylamide) copolymer, DOPEAMP (3-N,N-
dimethylaminopropylacrylamide/dimethylaminopropylacrylamide) copolymer, DOPEAMP (N-acryloyl
asparaginamide/dimethylamino) Propylacrylamide) copolymer, DOPEAMP (N-acryloylglycinamide/
dimethylaminopropylacrylamide) copolymer, DOPEAMP (N-acryloylglutamineamide/
dimethylaminopropylacrylamide) copolymer, DOPEAMP (N-acetylacrylamide/dimethylaminopropylacrylamide)
copolymer, DOPEAMP (N-methylacryloyl asparaginamide/dimethylaminopropylacrylamide) copolymer,
DOPEAMP (N,N-dimethylmethacrylamide/dimethylamine) Minopropylacrylamide) copolymer, DOPEAMP (N,N-
dimethylacrylamide/dimethylaminopropylacrylamide) copolymer, DOPEAMP (N,N-methylenebisacrylamide/
dimethylaminopropylacrylamide) copolymer, DOPEAMP (N,N-ethylmethylacrylamide/dimethyl)
Aminopropylacrylamide) copolymer, DOPEAMP (N,N-ethylmethylamide/dimethylaminopropylacrylamide)
copolymer, DOPEAMP (N,N-ethylmethylmethacrylamide/dimethylaminopropylacrylamide) copolymer, DOPEAMP
(N,N-dialkyl-dithio) Carbamylmethyl/dimethylaminopropylacrylamide) copolymer, DOPEAMP (N,N-
dialkylacrylamide/dimethylaminopropylacrylamide) copolymer, DOPEAMP (N,N Diethylacrylamide/
dimethylaminopropylacrylamide) copolymer, DOPEAMP (N,N-diethylamide/dimethylaminopropylacrylamide)
copolymer, DOPEAMP (N,N-diethylmethacrylamide/dimethylaminopropylacrylamide) copolymer, DOPEAMP (N,
N-dithiocarba) Myric acid/dimethylaminopropylacrylamide) copolymer, DOPEAMP (N,N-dithiocarbamate/
dimethylaminopropylacrylamide) copolymer, DOPEAMP (N,N-dimethylacrylamide/
dimethylaminopropylacrylamide) copolymer, DOPEAMP (N,N-dimethylmethacryl) Amide/
dimethylaminopropylacrylamide) copolymer, DOPEAMP (N,N-propylacrylamide/dimethylaminopropylacrylamide)
copolymer, DOPEAMP (N,N-Propyl methacrylamide/dimethylaminopropylacrylamide) copolymer, DOPEAMP (N-
acryloylpiperidine/dimethylaminopropylacrylamide) copolymer, DOPEAMP (N-acryloylmorpholine/
dimethylaminopropylacrylamide) copolymer, DOPEAMP (N-alkylacrylamide/dimethylaminopropyl) Acrylamide)
copolymer, DOPEAMP (N-alkyl methacrylamide/dimethylaminopropyl acrylamide) copolymer, DOPEAMP (N-
alkyl substituted acrylamide/dimethylaminopropyl acrylamide) copolymer, DOPEAMP (N-alkyl substituted
methacrylamide/dimethylaminopropyl acrylamide) copolymer, DOPEAMP (N-Allenylphthalimide/
dimethylaminopropylacrylamide) copolymer, DOPEAMP (N-Isopro Pyracrylamide/
dimethylaminopropylacrylamide) copolymer, DOPEAMP (N-isopropylamide/dimethylaminopropylacrylamide)
copolymer, DOPEAMP (N-isopropylbut-2,3-dienamid/dimethylaminopropylacrylamide) copolymer, DOPEAMP (N-
isopropylmethacryl) Amide/dimethylaminopropylacrylamide) copolymer, DOPEAMP (N-ethylacrylamide/
dimethylaminopropylacrylamide) copolymer, DOPEAMP (N-ethylmethacrylamide/
dimethylaminopropylacrylamide) copolymer, DOPEAMP (N-ethoxyethylacrylamide/
dimethylaminopropylacrylamide)) Copolymer, DOPEAMP (N-ethoxyethylamide/dimethylaminopropylacrylamide)
copolymer, DOPEAMP (N-ethoxy Ethyl methacrylamide/dimethylaminopropylacrylamide) copolymer, DOPEAMP
(N-cyclopropylacrylamide/dimethylaminopropylacrylamide) copolymer, DOPEAMP (N-cyclopropylamide/
dimethylaminopropylacrylamide) copolymer, DOPEAMP (N-cyclopropylmethacrylamide/

TABLE 17-continued

| |
|---|
| Dimethylaminopropylacrylamide) copolymer, DOPEAMP (N-tetrahydrofurfurylacrylamide/ dimethylaminopropylacrylamide) copolymer, DOPEAMP (N-tetrahydrofurfurylmethacrylamide/ dimethylaminopropylacrylamide) copolymer, DOPEAMP (N-biotinyl-N'-metachloro) Yltrimethyleneamide/ dimethylaminopropylacrylamide) copolymer, DOPEAMP (N-vinylacrylamide/dimethylamido) Propylacrylamide) copolymer, DOPEAMP (N-vinylalkylacrylamide/dimethylaminopropylacrylamide) copolymer, DOPEAMP (N-vinylmethacrylamide/dimethylaminopropylacrylamide) copolymer, DOPEAMP (N-propylacrylamide/ dimethylaminopropylacrylamide) copolymer, DOPEAMP (N-methacryloylpiperidine/ dimethylaminopropylacrylamide) copolymer, DOPEAMP (N-dialkylmethacrylamide/ dimethylaminopropylacrylamide) copolymer, DOPEAMP (s-butylacrylamide/dimethylaminopropylacrylamide) copolymer, DOPEAMP (t-butylacrylamide/dimethyl) Aminopropylacrylamide) copolymer, DOPEAMP (Acroylglycinamide/dimethylaminopropylamine) Rylamide) copolymer, DOPEAMP (acroyl sarcosine amide/ dimethylaminopropyl acrylamide) copolymer, DOPEAMP (acroyl nipecotamide/dimethylaminopropyl acrylamide) copolymer, DOPEAMP (acroyl methyl uracil/dimethylaminopropyl acrylamide) copolymer, DOPEAMP (Acetylacrylamide/dimethylaminopropylacrylamide) copolymer, DOPEAMP (isopropylacrylamide/ dimethylaminopropylacrylamide) copolymer, DOPEAMP (ethylisopropylacrylamide/ dimethylaminopropylacrylamide) copolymer, DOPEAMP (ethylene glycol/dimethylaminopropylacrylamide) copolymer, DOPEAMP (ethylene Glycol allenyl methyl ether/dimethylaminopropyl acrylamide) copolymer-, DOPEAMP (oxyethylene acrylate/dimethylaminopropyl acrylamide) copolymer, DOPEAMP (oxyethylene sorbitan laurate/dimethylaminopropyl acrylamide) copolymer, DOPEAMP (oxyethylene methacrylate/dimethylaminopropyl acrylamide) copolymer, DOPEAMP (Oxyethylene laurylamine/dimethylaminopropyl acrylamide) copolymer, DOPEAMP (oligoethylene glycol acrylate/dimethylaminopropyl acrylamide) copolymer, DOPEAMP (diisopropyl acrylamide/dimethylaminopropyl acrylamide) copolymer, DOPEAMP (diethyl acrylamide/dimethylaminopropyl acrylamide) Copolymer, DOPEAMP (diethylaminoacrylate/dimethylaminopropyl Rylamide) copolymer, DOPEAMP (diethylaminomethacrylate/dimethylaminopropylacrylamide) copolymer, DOPEAMP (diethylene glycol allenyl methyl ether/dimethylaminopropyl acrylamide) copolymer, DOPEAMP (dibutyl acrylamide/dimethylaminopropyl acrylamide) copolymer, DOPEAMP (dipropyl acrylamide/Dimethylaminopropylacrylamide) copolymer, DOPEAMP (dimethylacrylamide/dimethylaminopropylacrylamide) copolymer, DOPEAMP (dimethylaminoacrylamide/ dimethylaminopropylacrylamide) copolymer, DOPEAMP (dimethylaminoacrylate/ dimethylaminopropylacrylamide) copolymer, DOPEAMP(methylacrylamide/dimethylaminopropylacrylamide) copolymer. |

Instead of the dioleoylphosphatidylethanolamine shown above, lipids with the ethanolamine group can be used in the present invention. In the results of the stability test (40° C., humidity 80%, 6 months), the decomposition rate of these substances was 10% or less. The lipid having an ethanolamine group that can be used for the stimulus-responsive polymer-bound lipid of the present invention is shown in Table 18.

TABLE 18

| |
|---|
| 2-alkyl-N-carboxymethyl-N-hydroxyethylimidazolinium betaineethanolamine, N-acylaspartate ethanolamine, N-acylglutamate ethanolamine, N-acylsarcosine ethanolamine, N-acylmethylalanineethanolamine, N-acylmethyltaurineethanolamine, N-stearoyldihydrosphingoethanolamine, N-stearoylphytosphingethanolamine, acyl (C12,14) aspartate ethanolamine, acyl N-methylamino acid ethanolamine, acylamino acid ethanolamine, acyl lactic acid Ethanolamine, acetylethylcarboxylmethylthiazolidinecarbonylethanolamine, betaineethanolamine aminoacetate, Kill (alkenyl) oligoglycolethanolamine, alkylphenol polyglycolethanolamine, alkoxylated triglycerylethanolamine, phytosterylethanolamine isostearate, caproylproline ethanolamine, glycerophosphate ethanolamine, glucuronic acid ethanolamine, cocoylalanine ethanolamine, Cocoyl glutamate ethanolamine, cocoyl methyl taurine ethanolamine, succinate ethanolamine, surfactin ethanolamine, distearoyl glutamate lysine ethanolamine, diphosphatidyl glycerol ethanolamine, dimyristoyl glutamate lysine ethanolamine, dilauroyl glutamate lysine ethanolamine, Linoleoyl lysine ethanolamine glutamate, dioctyldodecyl ethanolamine stearoyl glutamate, ethanolamine stearoyl glutamate, ethanolamine spiculisporate, sphingethanolamine, ceramide phosphoethanolamine, ceramide aminoethyl phosphoethanolamine, cerebroside ethanolamine, palm kernel oil fatty acid Amidopropyl betaine ethanolamine, ethanolamine palm fatty acid glutamate, ethanolamine palmitoyl aspartate, bis (Nε-lauroyl-L-lysine) sebacoilethanolamine, hydroxystearyl phytosphingosine ethanolamine, polyoxyethylene glycerylethanolamine pyroglutamate isostearate, Glycerylethanolamine pyroglutamate oleate, phosphatidylethanolamine, polyoxyethylene stearylethanolamine, polyoxyethylene sorbitan stearylethanolamine, polyoxyethylene sorbitan fatty acid ester, polyoxyethylene methyl glucose stearylethanolamine, polyoxyethylene stearylethanolamine, Polyoxyethylene laurylethanolamine, ethanolamine myristoylglutamate, hexyldecylethanolamine myristoylmethylaminopropionate, myristoylmethyltaurineethanolamine, polyoxyethylene sorbitan ethanolamine monooleate, coconut oil alkyl betaineethanolamine, coconut oil fatty acid N—Me Ethylamine, coconut fatty acid acylglycine ethanolamine, coconut oil fatty acylglutamate ethanolamine, coconut oil fatty acid amidopropyl betaine ethanolamine, coconut oil fatty acid glycerylethanolamine, coconut oil fatty acid glutamate ethanolamine, coconut oil fatty acid sarcosine ethanolamine, Coconut oil fatty acid methylalanine ethanolamine, coconut oil fatty acid methyltaurine ethanolamine, lauramide propyl betaine ethanolamine lauryl amino diacetate ethanolamine, lauryl diaminoethyl glycine ethanolamine, lauryl dimethyl amino acetate betaine ethanolamine, lauric amide propyl betaine, Ethanolamine laureth acetate, ethanolamine laureth sulfate, lauro Ethanolamine ruaspartate, dihexyldecylethanolamine lauroylglutamate, triethanolamine lauroylglutamate, methylalanineethanolamine lauroylglutamate, ethanolamine lauroylglutamate, triethanolamine lauroylglutamate, lauroylsarcosine triethanolamine, lauroylmethylalanylethanolamine, lauroylmethylamine Methylglycineethanolamine, lauroylmethyltaurineethanolamine, lauroylmonoethanolamide succinate ethanolamine, lysophosphatidylethanolamine |

pH, Production of Photo-Stimulus-Sensitive Polymers

In the case of pH and photo-stimulus-responsive polymers, the polymer containing N atoms can bind the polymer to the carrier particles for cell delivery by ionic bonding, so that polymerization can be carried out with only the first monomer without adding 3-mercaptopropionic acid, and in that case, the polymer described in the following can be produced. The degradation rate of these polymers was less than 10% according to the results of a stability test at 40° C., 80% humidity, and 6 months. Polyglucosamine, (alkylacrylamide/polyacrylic acid) copolymer, polyvinylalkylacrylamide, polyalkylacrylamide, poly(phenylazophenyl)acrylamide, poly[(4-pyridylazo)phenoxy]hexamethacrylate, N-vinylalkylacrylamide, poly[(vinyloxy)ethoxy]azobenzene.oly[(vinyloxy)ethoxy]azobenzene pH, Production of Photo-Stimulus-Sensitive MPA Polymers In the case of pH and photo-stimulus-responsive polymer, the polymerization reaction with the second monomer is not carried out because delicate temperature setting is not necessary, and the polymerization reaction with the first monomer only can be carried out to make the photo-stimulus-responsive polymer described in the following. In this case, the mixing ratio could be changed by reducing the second monomer and increasing the first monomer, and the following polymers could be produced. Mercaptopropionic acid is hereinafter referred to as MPA. The degradation rate of these polymers was less than 10% according to the results of a stability test at 40° C., 80% humidity, and 6 months. pH stimuli-responsive polymer: MPA (polyglucosamine), MPA (poly (ethoxyethyl vinyl ether)), MPA (alkylacrylamide/polyacrylic acid) copolymer, MPA (poly(vinylalkylacrylamide)), MPA (poly((vinyloxy (Ethoxy)benzoic acid), MPA (poly((vinyloxyethoxy) hexanoic acid)), MPA (poly((vinyloxy) hexanoic acid)), MPA (poly(isobutyl vinyl ether)), photostimuli-responsive polymer: MPA (poly(Alkyl acrylamide)), MPA (poly((4-phenylazophenyl) acrylamide)), MPA (poly([(pyridylazo) phenoxy]hexamethacrylate)), MPA (poly(vinylalkylacrylamide)), MPA (poly(((Vinyloxy) ethoxy) azobenzene)), MPA (poly((ethoxy) ethoxyethyl vinyl ether)))

Production of pH and Photo-Stimulus-Sensitive Polymer-Bound Lipids

The above MPA derivatives were used to modify the lamellar structure-forming lipid, dioleoylphosphatidylethanolamine, to similarly produce the stimulus-sensitive polymer-bound lipids. Dioleoylephosphatidylethanolamine mercaptopropionyl is hereinafter referred to as DOPEAMP. pH stimuli-responsive polymer: DOPEAMP (polyglucosamine), DOPEAMP (poly (ethoxyethyl vinyl ether)), DOPEAMP (alkylacrylamide/polyacrylic acid) copolymer, DOPEAMP (poly(vinylalkylacrylamide)), DOPEAMP (poly((vinyloxy (Ethoxy)benzoic acid), DOPEAMP (poly ((vinyloxyethoxy) hexanoic acid)), DOPEAMP (poly((vinyloxy) hexanoic acid)), DOPEAMP (poly(isobutyl vinyl ether)), photostimulant-responsive polymer: DOPEAMP (poly(Alkyl acrylamide)), DOPEAMP (poly((4-phenylazophenyl) acrylamide)), DOPEAMP (poly([(pyridylazo) phenoxy]hexamethacrylate)), DOPEAMP (poly(vinylalkylacrylamide)), DOPEAMP (poly(((Vinyloxy) ethoxy) azobenzene)), DOPEAMP (poly((ethoxy) eth) Xyethyl vinyl ether))

Preparation of a Triplicate Delivery Carrier into the Cell Comprising Stimulus-Responsive Polymer-Bound Lipids, Vitamin Derivatives with ATG-CTS Activity, and a Lamellar Surfactant Comprising Hydrocarbons The total amount of lipid is 20 mg, the molar ratio of VCIPs (ascorbyl tetrahexyl decanoate) which are vitamin derivatives with high ATG-CTS activity,: lamella-forming surfactants DOPE and DOPEMP (NIPAA/DMAPAA) Cop., was 3:7. Each was dissolved in chloroform. The molar ratio of the lamella-forming surfactant dioleoylphosphatidylethanolamine (DOPE) to the temperature-stimulated responsive polymer-binding lipid DOPEMP (NIPAA/DMAPAA) Cop. Was 6.5:0.5. The solution was transferred to an eggplant flask and the solvent was blown off by an evaporator to prepare a lipid film. 1 ml of purified water was added to this lipid film, the lipid film was hydrated, and then dispersed by vortexing. Then, sonication was performed in an ultrasonic bath for 30 minutes to reduce the size of the liposomes, and then the liposomes were sized through a 200 nm filter using an extruder. The average particle size was 152 nm. Then, the liposomes were separated and purified by gel filtration to prepare a Delivery carrier into cell of the present invention containing an ATG-CTS activator, a temperature-responsive polymer and a hydrocarbon. When these delivery carriers into cell were observed with a transmission electron microscope by a staining method, a multilayer vesicle structure (lamella liquid crystal structure) was confirmed, and it was confirmed that these delivery carriers into cell had a lamella liquid crystal structure was confirmed.

Preparation of Delivery Carrier into the Cell Comprising Stimulus-Responsive Polymer-Bound Lipids, Vitamin Derivatives with ATG and CTS Activities, and Lamellar Surfactants and Lipids Composed of Hydrocarbons Lecithin 2%, glycerin 50%, behenyl alcohol 8%, stearyl alcohol 7%, PEG-20 phytosterols 4%, cetanol 3%, phytosterols 1%, glyceryl stearate 1%, tri(caprylic/capric acid) glyceryl 2%, cholesterol 0.3%, GOVC (glyceryl octyl ascorbyl) 1% and DOPEMP (NIPAA/DMAPAA) Cop 0.2% and squalane 10%, which are vitamin derivatives with high ATG and CTS activity, were added and kneaded with a spinning and rolling agitator. To this, purified water was added and dispersed by vortexing as 100%. The liposomes were then sonicated in an ultrasound chamber for 30 min to reduce the size of the emulsion particles, and then passed through a 200 nm filter using an extruder to size up the liposomes. The average particle size was 122 nm. The liposomes were then separated and purified by gel filtration to prepare the delivery carrier into the cell of the present invention containing ATG-CTS activators and temperature-stimulus-responsive polymers and hydrocarbons. The delivery carrier into the cell were observed by transmission electron microscopy using a staining method, and the multi-layered vesicle structure (lamellar liquid crystal structure) was confirmed. confirmed.

A Comparison Experiment with the Present Invention

The total amount of lipid is 20 mg, the molar ratio of VCIP: (lipid 1,2-diore oil-3-trimethylammonium propane):

(total weight of lamella-forming surfactant DOPE and DOPEMP (NIPAA/DMAPAA 5%) Cop.) was 1:2:7. Each was dissolved in chloroform. Furthermore, 1 mg of rhodamine (Carboxyrhodamine 110-PEG4-alkyne), which is a fluorescent dye, was added and dissolved. The lower limit critical dissolution temperature of DOPEMP (NIPAA/DMAPAA 5%) Cop. used in this experiment in water was 40° C. The molar ratio of DOPE to DOPEMP (NIPAA/DMAPAA) Cop. was 6.5:0.5. The solution was transferred to an eggplant flask and the solvent was blown off by an evaporator to prepare a lipid film. 1 ml of PBS was added to this lipid film, the lipid film was hydrated, and then dispersed by vortexing. Then, sonication was performed in an ultrasonic bath for 30 minutes to reduce the size of the liposomes, and then the liposomes were sized through a 200 nm filter using an extruder. The average particle size of Examples and Comparative Examples was 114 nm±13 nm. Separately, filters having an average particle size of 252 nm, 312 nm, 578 nm, and 812 nm were also prepared using filters of different large sizes only in the examples of the present invention. Then, the liposomes were separated and purified by gel filtration to prepare a Delivery carrier into cell of the present invention containing an ATG, CTS activator, a temperature-responsive polymer and a hydrocarbon. When these delivery carriers into cell were observed with a transmission electron microscope by a staining method, a multilayer vesicle structure (lamella liquid crystal structure) was confirmed, and it was confirmed that these delivery carriers into cell had a lamella liquid crystal structure. liquid crystal structure) was confirmed.

Comparative Example 1

Lipofectamine (Lipofectamine (registered trademark) RNAiMAX) manufactured by Invitrogen was used as the liposome of Comparative Example 1. This was inoculated with rhodamine so that the final concentration was the same as in the embodiment.

Comparative Example 2

Liposomes were prepared in the same way as in Example 1 except that DOPEMP (NIPAA/DMAPAA) Cop was not added in the preparation of liposomes. Comparative Example 2 is similar to Example 1 except that the temperature-stimulus-responsive polymer is not present.

Comparative Example 3

Liposomes were prepared in the same way as in Example 1 except that PEG (polyethylene glycol, molecular weight: 2000) was used instead of DOPEMP (NIPAA/DMAPAA) Cop.

Normal human epidermal fibroblasts were cultured in DMEM (low glucose) containing 5% FBS for 24 hours at 37° C. at a density of 5x105 cell/well in 6-well plates, and then the plates were changed to medium containing four delivery carrier into the cell (rhodamine was added to a final concentration of 1 μM), including the embodiments and comparative examples described above, and cultured at 35° C. for 1 hour. Afterwards, in the group of only the embodiments of the invention, we differentiated between groups that were kept at the same culture temperature for 20 min and groups that were treated at 40° C. for 20 min, and both groups were incubated at 35° C. for 1 h. Then, the cell were washed five times with PBS and immobilized with 4% paraformaldehyde phosphate buffer solution for 20 min, washed twice with PBS again, and the relative concentration of fluorescent substances taken up into the cell was determined by measuring the fluorescence intensity at the excitation wavelength of 555 (nm) and the fluorescence wavelength of 580 (nm) with a fluorescent microplate reader. cell of delivery carrier into the cell without vitamin derivatives were also cultured in the same way as additive-free controls and the fluorescence intensity was measured.

As a result, when the fluorescence intensity of the particle size of 114 nm in the group treated at 40° C. for 20 min was set to 100%, the fluorescence intensity of the comparative example 1, 2, and 3 was 82%, 35%, and 22%, respectively. From these results, it was found that the delivery carrier into the cell of the present invention has a very high cell uptake performance.

When the fluorescence intensity of a particle with a diameter of 114 nm in the group treated at 40° C. for 20 minutes was set at 100%, the fluorescence intensity of a particle with a diameter of 114 nm in the group kept at 35° C. for 20 minutes was 80% in the embodiment, and it is clear that the absorption rate into cell increased in the group treated at 40° C. for 20 minutes. The fluorescence intensities of the average particle size of the embodiments of the present invention of further different sizes were 94% at 252 nm, 81% at 382 nm, 72% at 578 nm, and 51% at 812 nm, and it was confirmed that the average particle size of 300 nm showed high cellular absorption.

a Comparison Experiment Between Lamellar and Non-Lamellar

A-10: A Delivery carrier into cell with lamellar liquid crystal structure: 15 g of glycerin, 3.6 g of diglycerin, 2 g of sodium cocoyl glutamate, 1 g of GOVC (an amphiphilic vitamin derivative that combines a substrate comprising 2-glyceryl-3-Caprylyl ascorbate, glycerin:Caprylyl:ascorbate in a weight ratio of 0.223:0.35:0.427), 1 g of DOPEMP (NIPAA/DMAPAA) Cop and 0.05 g of cholesterol, 0.1 g of PEG-25 Phytostanol (INCI name: PEG-25 Phytostanol) were added at 70° C., and kneaded well for 10 minutes while cooling naturally with a electric hand mixer, and 5 g of squalane containing 5% retinol was added and kneaded well for 10 minutes with an electric hand mixer. This lipid-adding kneading process is repeated four times in total to add a total of 20 g of squalane containing 5% retinol by weight. To this, purified water which 8% phenoxyethanol was added was added to make 100 g. The composition, which is a lamellar liquid crystal emulsion containing the retinol of the present invention, was completely dispersed by stirring with an electric hand mixer for 10 minutes so as not to form bubbles. These delivery carrier into the cell were microfluidized and further sized into nano-ordered capsules using a 400 nm pore size filter. A Delivery carrier into cell with an average particle diameter of 253 nm was obtained. Transmission electron microscopy of these delivery carrier into the cell by staining revealed a multi-layered vesicle structure (lamellar liquid crystal structure), confirming that these delivery carrier into the cell have a lamellar liquid crystal structure.

B-10: Control: GOVC was changed from A-10 above to the base ingredient as a control. The amount of glycerin was increased from 0.22 g of glycerin added from the beginning, 0.35 g of Caprylyl was added to squalane beforehand, and 0.6 g of 3Na ascorbate phosphate (the same molar mass of ascorbate) was added to the purified water added at the end to make it the same molar mass as A-10.

Sample C-10: Non-lamellar delivery carrier into the cell with amphiphilic antioxidant vitamins (control 2): 15 g glycerin, 3.6 g diglycerin, 2 g Na cocoyl glutamate, 1 g GOVC and 1 g DOPEMP (NIPAA/DMAPAA) Cop. 1 g, 0.05 g cholesterol, 0.1 g PEG-25 phytostanol, 25 g 5% weight squalane containing retinol and 52.25 g 8% weight purified phenoxyethanol water were mixed with DOPEMP (NIPAA/DMAPAA) Cop 1 g, 0.05 g cholesterol, 0.1 g PEG-25 phytostanol, 25 g 5% weight squalane containing retinol and 52.25 g purified water with 8% weight phenoxyethanol. These were crushed and stirred with a high-speed mixer without going through the process of forming a lamellar structure. The delivery carrier into cell was then sonicated and then microfluitad with his iser to obtain a delivery carrier into cell with an average particle diameter of 300 nm. Furthermore, they were sized into nano-order capsules using a filter with a pore size of 400 nm.

Sample D-10: Control of carriers for delivery of non-lamellar cell containing no parentomogenic antioxidant vitamins: glycerin 15.22 g, diglycerin 3.6 g, cocoyl glutamate Na 2 g, GOVC 1 g and DOPEMP (NIPAA/DMAPAA) Cop 1 g, Cholesterol 0.05 g, PEG-2 5 phytostanol 0.1 g, capric acid 0.35 g, 5% weight retinol-containing squalane 25 g, ascorbic acid phosphate 3Na salt 0.6 g, and purified water 52.25 g with 8% weight phenoxyethanol were mixed. These were crushed and stirred with a high-speed mixer without going through the process of forming a lamellar structure, and then ultrasonically treated, and this delivery carrier into cell was treated with a microfluitizer to obtain a delivery carrier into cell having an average grain diameter of 300 nm. It also was sized into nano-order capsules using a 400 nm pore size filter.

The retinol content of A-10, B-10, C-10, and D-10 was measured by HPLC at the beginning and end of the experiment after 3 months of storage at 40° C. in the shaded condition. The analytical conditions are as follows. Column: Shim-pack FC-ODS (75 mm L.×4.6 mm), solvent: Methanol, flow rate: 1.2 mL/min, column temperature: 35° C., detection wavelength: 350 nm.

As a result, the stability of retinol of A-10 was 95.67%, B-10 was 73.2%, C-10 was 32.5%, and D-10 was 22.7%, respectively, at the end of the experiment, when the retinol content at the start of the experiment was 100%. Furthermore, when the active ingredient such as retinol is easily oxidized, antioxidants have been used to prevent the oxidation of the active ingredient, but the problem is that the active ingredient is oxidized due to the short effective period of antioxidants.

The delivery carrier into cell of the present invention of Example A-10, The delivery carrier into cell of B-10, C-10, D-10, E-10, and the placebo cream containing no delivery carrier into cell witch be used as a negative control. A cream was prepared according to the following prescription, and its anti-wrinkle, anti-acne, moisturizing, barrier function-enhancing, UV-derived inflammation-suppressing, and radical-suppressing effects were evaluated.

For the formula of the test cream, A-10, B-10, C-10, and D-10 were added to the cream substrate made by ITO Co. Ltd. (Nishi-Tokyo City, Tokyo) with 10% weight each, and mixed with a rotary mixer for 5 minutes.

A total of 100 people suffering from healthy people and wrinkles, acne, pigmentation, and dry skin, 20 people each in 5 groups (A-10, B-10, C-10, D) so that the symptoms in each test group are uniform. −10 Addition plot and placebo plot). Each effect was evaluated for these subjects. In the case of a healthy person, 0.01 ml of the above-mentioned external preparation was applied to the cheek and other patients twice a day in the morning and evening, and the applied part was covered with a hot steaming towel for 5 minutes after the application. The colors of the lesions before the start of the application test and 10 days after the start of the test were photographed with a digital camera under the same lighting conditions. Wrinkles, acne, and pigmentation were quantified from this image using the image processing device VISIA. In addition, for healthy subjects, the amount of lipid peroxide in the skin fat was measured by impregnating the filter paper with sebum, and the amount of lipid peroxide in the sebum was measured using the filter paper of the lipid peroxide measurement kit. Drying and barrier functions were compared by measuring the water content of the stratum corneum and the water evaporation of the epidermis. Pressure ulcers were quantified by comparing the degree of improvement with the naked eye according to the pressure ulcer standard manual. As for the results, 60 days after the start of the test, the total score of 20 people was calculated for each test group, and the percentage of the test group and the target group was calculated with the total score of placebo cream as 100%.

After 60 days of the test, when the placebo was set to 100%, the effect of A-1 was 44% on wrinkles, 27% on acne, and 35% on hyperpigmentation. Furthermore, the water content in the stratum corneum increased by 141% and the epidermal water transpiration improved by 132%, and dry skin was improved. It was confirmed that it was effective in anti-wrinkle, anti-acne, whitening, moisturizing, and strengthening barrier function. The effects of B-1 were 69% for wrinkles, 64% for acne, 72% for pigmentation, 119% for stratum corneum water content, and 116% for epidermal water transpiration; the effects of C-1 were 85% for wrinkles, 81% for acne, 91% for pigmentation, 105% for stratum corneum water content, and 104% for epidermal water transpiration; and the effects of D-1 were 91% for wrinkles, 89% for acne, 95% for pigmentation, 95% for stratum corneum water content, 106% for stratum corneum water content, and 109% for epidermal water transpiration.

In addition, the concentration of lipid peroxide in the sebum collected from the cheek skin of patients in the A-1 section was reduced by 36% compared to the negative control. As a result, it was confirmed that this product is very effective as a drug, quasi-drug, unapproved drug, and cosmetic.

Stability and uptake experiments of carriers for temperature-stimulus-responsive cell delivery Sample A-1) Carrier for delivery of temperature-responsive lamella cell containing amphipathic antioxidant vitamins (invention). Egg yolk-derived phosphatidylcholine 1 g, chloroform oil phosphatidylethanolamine 0.8 g, DOPEMP (NIPAA/DMAPAA) Cop. 3 g, cholesterol 0.05 g, PEG-25 phytostanol (INCI name PEG-25 Phytostanol) 0.1 g and GOVC (0.1 g of an amphipathic vitamin derivative in which a substrate comprising 2-glyceryl-3-caprylic ascorbic acid and glycerin: capric acid: ascorbic acid was bound at a weight ratio of 0.223: 0.35:0.427) was dissolved in 200 mL chloroform. Then, the solvent was removed from this with an evaporator to form a lamellar structure film.

1 mL of a peptide-bonded fluorescent substance solution (ovalbumin: fluorescein isothiocyanate=1:1 equimolar mixed aqueous solution) dissolved in PBS at a concentration of 0.2 mg/mL and mir-125a-siRNA duplex (1 mL of a diluted solution of luciferase activity-suppressing protein biosynthetic RNA) at a concentration of 200 nM in PBS (hereinafter referred to simply as siRNA solution) was mixed. The film was then crushed with a mixer, then sonicated, and then sized into nano-order capsules using a 400 nm pore size filter. Carriers for cell delivery were purified by gel filtration using a PD-10 column.

Sample B-1: temperature-stimulus-responsive lamellar delivery carrier into the cell containing substrates that constitute amphiphilic antioxidant vitamins (Control 1). 1 g of egg yolk-derived phosphatidylcholine, 0.8 g of dioleoylphosphatidylethanolamine, 3 g of DOPEMP (NIPAA/DMAPAA) Cop. and 0.05 g of cholesterol, 0.1 g of PEG-25 phytostanol and 0.035 of Caprylyl were dissolved in chloroform, and the solvent was removed with an evaporator to form a lamellar structural film. To this, 1 mL of peptide-binding fluorophore solution (same as sample A-1) was mixed with 0.043 g of ascorbate and 0.022 g of glycerin and 1 mL of siRNA solution. Next, the films were crushed with a high-speed mixer, then sonicated, and further sized into nano-order capsules using a 400 nm pore size filter; the carriers for cell delivery were purified by gel filtration using a PD-10 column.

Sample C-1) Non-lamellar delivery carrier into the cell with amphiphilic antioxidant vitamins (control 2). 1 g of egg yolk-derived phosphatidylcholine and 0.8 g of dioleoylphosphatidylethanolamine, 3 g of DOPEMP (NIPAA/DMAPAA) Cop. and 0.05 g of cholesterol, 0.1 g of PEG-25 phytostanol and 0.1 g of GOVC, mixed with 1 mL of peptide-bound fluorescent substance solution (same as sample A-1) and 1 mL of siRNA solution. These were crushed and stirred with a high-speed mixer without going through the process of forming lamellar structural films, then sonicated, and further passed through a filter with a pore size of 400 nm.

Sample D-1) Control for non-lamellar delivery carrier into the cell without amphiphilic antioxidant vitamins. 1 g of egg yolk-derived phosphatidylcholine and 0.8 g of dioleoylphosphatidylethanolamine and 3 g of DOPEMP (NIPAA/DMAPAA) Cop. and 0.05 g of cholesterol and 0.1 g of PEG-25 phytostanol were mixed with 1 mL of peptide-bound fluorescent substance solution (same as sample A-1) and 1 mL of siRNA solution. These were crushed and stirred with a high-speed mixer without going through the process of forming lamellar structural films, then sonicated, and further passed through a filter with a pore size of 400 nm.

Measurement of Particle Size of Delivery Carrier into the Cell

The particle sizes of the delivery carrier into the cell prepared for samples A-1, B-1, C-1 and D-1 were measured at room temperature and measured using a particle size analyzer (ZETASIZER Nano-ZS). The average particle size of A-1 was 314 nm (range 120-450 nm) with a sharp single The average particle size of B-1 in the following control was 252 nm (range 155-342 The single sharp peak of C-1 and D-1 was found to be sharp (1.5 nm), however, C-1 and D-1 were separated with time and the peak of No stable delivery carrier into the cell were obtained.

Cell Uptake Experiment

125 μl of the A-1, control B-1, C-1, and D-1 composition solution of the present invention prepared above was taken and made up to 1 ml with FBS medium. The medium of HeLa cell (cervical cancer cell) cultured using a 6-well plate at a concentration of 5.0×104 cell/ml was changed to a dispersion and incubated at 37° C. for 48 hours. After incubation, the medium was removed from each, and 5-fold diluted Pickagene cytolytic agent Lcβ (Toyo Ink) was added at 250 μl/well and incubated for 30 minutes. Then, the obtained solution was frozen at −80° C., thawed at 37° C., and centrifuged at 12000 rpm for 5 minutes. A 50 μl Pickagene solution was added to 10 μl of the obtained supernatant to measure luminescence, and the intracellular luciferase activity was measured to determine the intracellular uptake rate of nucleic acid (siRNA) by the following formula. The siRNA mir-125a used in this experiment suppresses luciferase activity when taken up by cell, so the smaller the amount of luciferase emitted, the more siRNA was taken up by cell.

Nucleic acid (siRNA) conjugation=luciferase luminescence: C (count per second)/protein amount: P (proton abundance).

In addition, 10 μl of the culture medium of cervical cancer cell that had not delivered siRNA into the cell was used for protein quantification using a BCA (bicinchoninic acid) assay kit, and a calibration curve was prepared using a BCA standard product, and the above C/P value was set to 100% (control), and the RNA conjugation rate of the above example was expressed as a percentage via luciferase activity. The results showed that the luciferase activity (The lower the luciferase activity, the higher the intracellular uptake rate.) was decreased in A-1 of the present invention, A-1 was 19%, B-1 was 62%, C-1 was 85%, and D-1 was 81%.

Measurement of Conjugation of Water-Soluble Fluorescent Dyes

The A-1 of the present invention prepared above and the B-1, C-1, D-1 composition solution of the following control were incubated for 1 week under a temperature stress of 40° C. Then, the stability of the fluorescence characteristics of each composition was investigated. That is, it was diluted 20-fold with PBS and its fluorescence intensity was measured with a fluorometer to determine the fluorescence intensity at the time of intracellular uptake of the peptide-bonded fluorescent substance. In addition, after adding 1% of Tri ton10× to completely disintegrate the Delivery carrier into cell, the peptide-bound fluorescent substance fraction was separated by gel filtration, and the fluorescence intensity of the fraction was taken as the fluorescence intensity after heat stress. Then, the difference from the fluorescence intensity at the time of intracellular uptake was obtained from the value of the fluorescence intensity when Triton was added. For relative comparison, the intracellular uptake rate of control was calculated with the calculated value of A-1 as 100%. As a result, A-1 of the present invention was 100%, B-1 of the control was 25%, C-1 was 2%, and D-1 was 3%. From this result, the cell uptake rate after heat stress of A-1, which is a carrier for delivery of amphipathic antioxidant vitamin-containing lamella cell of the present invention, was the highest.

Comparison of Skin Permeability Using Franz Cell (Comparison of skin permeability using Franz cell) LabCyte EPI-MODEL was used as an epidermal skin model. Artificial skin was sandwiched between Franz Cell and incubated at 37° C. 1 mL each of the A-1 (the invention) and control B-1, C-1, and D-1 composition solutions prepared above containing the prepared peptide-bonded fluorescent substance was administered to the donor chamber. Forty-eight hours after administration, 10 μL of 10% Triton X was added to 150 μL of the emulsified composition incorporating the sampling sample of the sampling port and the peptide-bonded fluorescent substance to prepare a sample solution. The fluorescence intensity of 100 μL of the sample solution was measured using a fluorometer infinite M1000. The skin permeability was calculated from the following formula. As a result, A-1 (the invention) of the present invention was 42%, B-1 of the control was 19%, C-1 was 5%, and D-1 was 4%. The skin permeability of A-1, which is a carrier for the drug, was the highest, and its superiority was confirmed. Permeation Rate (%)=(Fr/Fd)×100 (Fr: Fluorescence of sample from receptor, Fd: Fluorescence of donor)

The formulation using this lamellar liquid crystal is effective at low concentration if the effective concentration of GOVC in the formulation is 0.01% or more. This may be due to the increased skin absorption rate.

The concentration of GOVC (2-glyceryl-3-Caprylyl ascorbate) or OGVC (of 3-glyceryl-2-Caprylyl ascorbate,) in the formulation was increased to 1%, but no skin irritation was observed. This was due to the fact that the skin irritation of GOVC or OGVC was weakened by lamellar liquid crystal. These results indicate that the lamellar liquid crystal emulsions of the present invention are very effective as a source of ascorbic acid (ASA) as a pharmaceutical product, quasi-drug, unapproved drug, and cosmetics, and as a topical composition with suppressed ASA radical generation.

In Vitro Skin Irritation Test Inclusion in OECD TG-439

In Vitro Skin Irritation Test of Cultured Cell According to OECD Guidelines. OECD Guidelines for the Testing of Chemicals, 439. (2015)

LabCyte EPI-MODEL was used as a normal skin epidermis model, and a skin irritation test was performed and scored. As a result (the lower the score, the higher the toxicity), the score is 3 points for 5% SLS (positive control), 100 points for Water (negative control), 125 points for A-1 of the present invention, and B-1 was 101, C-1 was 89, and D-1 was 83, and the viable cell rate was 50% or higher in all the formulations. All skin irritation was denied. Among them, it was suggested that A-1 of the present invention has the highest safety. As a result of the test, no skin irritation of the test substance was observed in the normal skin model.

Preparation of Carrier for pH-Responsive Cell Delivery

Sample A-2: Carrier for delivery of pH-responsive lamella cell containing amphipathic antioxidant vitamins (invention) Egg yolk-derived phosphatidylcholine 3 g, chloroform oil phosphatidylethanolamine 0.8 g and cholesterol 0.15 g, PEG-25 phytostanol (INCI name PEG-25 Phytostanol) 0.3 g, GOVC (2-glyceryl-3-caprylic ascorbic acid, 0.1 g of an amphipathic vitamin derivative to which a substrate comprising glycerin: capric acid: ascorbic acid was bound at a weight ratio of 0.223:0.35:0.427) was dissolved in 150 mL of chloroform. Then, chloroform was removed under reduced pressure to prepare a film. 100 mL of a mixed solution of 0.5 mM calcein and 9.0% (w/v) sucrose was added thereto, and the lipid film was peeled off. After crushing using an ultrasonic tank, sizing was performed with a filter having a pore size of 100 nm. The average diameter of the carrier particles for cell delivery was 87 nm. The lamellar structure was confirmed by electron microscopic observation. Next, gel filtration was performed on the PD-10 column, and this was used as the pre-chitosan treatment solution. Next, this was added dropwise to a solution prepared by dissolving 0.1 (w/v) of chitosan solution in 1% (v/v) acetic acid solution. Then, the reaction was carried out at 40° C. for 5 hours and then cooled. This was used as the carrier for pH-responsive cell delivery of the present invention. Hereinafter, this is abbreviated as pH-GOVC-Chito.

Sample B-2: Carriers for pH-responsive lamellar cell delivery with substrates comprising amphiphilic antioxidant vitamins (Control 1): 3 g of egg yolk-derived phosphatidylcholine, 0.8 g of dioleoylphosphatidylethanolamine and 0.15 g of cholesterol, 0.3 g of PEG-25 phytostanol and 0.035 Caprylyl were dissolved in 150 mL of chloroform and chloroform was removed by an evaporator to make a film. To this, 100 mL of a mixture of 0.043 g of ascorbate, 0.022 g of glycerin, and 0.5 mM calcein and 9.0% (w/v) sucrose was added, the lipid film was removed and crushed by ultrasound using an ultrasonic chamber, and sizing was performed with a 100 nm pore diameter filter. This was then gel-filtered through a PD-1C column, and dripped into a chitosan solution of 0.1 (w/v) dissolved in 1% (v/v) acetic acid solution, and reacted at 40° C. for 5 hours and cooled.

Sample C-2: Amphiphilic antioxidant vitamin-containing non-lamellar delivery carrier into the cell (Control 2) 3 g of egg yolk-derived phosphatidylcholine, 0.8 g of diore-oil phosphatidylethanolamine and 0.15 g of cholesterol, 0.3 g of PEG-25 phytostanol and 0.1 g of GOCV, and 100 mL of a mixture of 0.5 mM calcein and 9.0% (w/v) sucrose were added, crushed with a high-speed mixer, sonicated, and passed through a 100 nm pore diameter filter. This was dropped into a solution of 0.1 (w/v) chitosan solution dissolved in 1% (v/v) acetic acid solution and reacted at 40° C. for 5 hours and then cooled.

Sample D-2: Amphiphilic non-lamellar delivery carrier into the cell without antioxidant vitamins (control 3) 3 g of egg yolk-derived phosphatidylcholine, 0.8 g of dioleoylphosphatidylethanolamine and 0.15 g of cholesterol, 0.3 g of PEG-25 phytostanol, and 100 mL of a mixture of 0.5 mM calcein and 9.0% (w/v) sucrose were added, crushed with a high-speed mixer, sonicated, and passed through a 100 nm pore diameter filter. This was dropped into a solution of 0.1 (w/v) chitosan solution dissolved in 1% (v/v) acetic acid solution and reacted at 40° C. for 5 hours and then cooled.

Since chitosan is positively charged, it has an ion bond to the oxygen atom bound to the phosphoric acid of phospholipids. Chitosan-conjugated delivery carrier into the cell, which were easily bound and densely covered with chitosan, were obtained. The delivery carrier into cell obtained here are described in Examples as 0.1% chitosan-bound delivery carrier into cell and 0.5% chitosan-bound delivery carrier into cell, respectively.

Particle Size Measurement

A delivery carrier into the cell solution diluted more than 100 times with 9.0% (w/v) Sucrose solution was placed in a microcuvette, and the particle size distribution at 25° C. was observed using dynamic light scattering (DLS). The particle size of the prepared cell carriers was 182 nm in the pre-chitosan-treated solution of A-2 pH-GOVC-Chito and 198 nm in the chitosan-conjugated cell carrier of A-2 pH-GOVC-Chito, indicating that the particle size increased with chitosan treatment.

Measurement of Surface Potential

The prepared delivery carrier into the cell solution was diluted 20-fold, and the surface potential was measured by electrophoretic light scattering (ELS) method using an ELS-Z2 zetasizer at 37° C. The Z potential of the surface potential of the prepared cell carriers was−15 mV in the pre-chitosan treatment solution of A-2 and 15 mV in the chitosan-conjugated cell carrier of A-2, and it was confirmed that the surface potential increased with chitosan binding. Since chitosan is positively charged, it was proved that chitosan can readily bind to negatively charged oxygen atoms bound to the phospholipid phosphate by ionic bonding to obtain a carrier for chitosan-bound cell delivery densely covered with chitosan.

Skin Permeability of pH-Reactive Delivery Carrier into the Cell

Using an epidermal skin model (LabCyte EPI-MODEL 12) and a Franz cell filled with PBS in the receptor, 1 mL of the delivery carrier into the cell solution of A-2 of the present invention and the following controls, B-2, C-2, and D-2, were added to the upper donor using 1 mL of the delivery carrier into the cell solution of the present invention and the following controls, B-2, C-2, and D-2, respectively, at 37° C. for 24 h. After incubation at 37° C., 150 μL of samples were taken from the PBS-filled lower receptor and upper donor sections, and 20 μL of Triton X-100 diluted 10-fold was added, and its fluorescence intensity was measured using Infinite M1000 (Ex 495 nm, Em 515 nm). From these values, the skin transmittance was calculated using the following equation. Cumulative % dose applied/$cm^2$=(Fluorescence of sample from receptor/Fluorescence of donor)×100%/0.64 $cm^2$ After 24 hours, the results were highest for the chitosan-bound delivery carrier into the cell of the A-2 of the present invention at 0.6, whereas the control B-2 was 0.3, C-2 and D-2 were 0.1. These results indicate that the pH-responsive lamellar delivery carrier into the cell with amphiphilic antioxidant vitamins of A-2 of the present invention showed much higher skin permeability than the pH-responsive lamellar delivery carrier into the cell with a substrate of antioxidant vitamins of B-2 (control 1), the non-lamellar delivery carrier into the cell with amphiphilic antioxidant vitamins of C-2 (control 2), and the non-lamellar delivery carrier into the cell without amphiphilic antioxidant vitamins of D-2 (control 3), which were used for comparison.

Melanin Production Inhibition Test

Pre-treatment: The following melanin production inhibition tests were performed using A-2, B-2, C-2, and D-2 pH-responsive delivery carrier into the cell (A-3, B-3, C-3, and D-3): HMV-II cell were seeded in 24 well dishes at a concentration of 1×105 cell/mL, incubated for 24 hours, and then added 200 μM of IBMX and A-3, B-3, C-3, and D-3 pH-responsive delivery carrier into the cell (A-3, B-3, C-3, and D-3) at an APS concentration of 100 μM. 2 hours later, the cell were washed with PBS, 200 μM of IBMX was added again, and incubated for 70 hours. The cell were then solubilized with 200 μL of NaOH at 1 mol/L, and melanin was extracted and quantified by measuring the absorbance at 405 nm. The melanin production was increased about 3-fold by the addition of IBMX (no carrier for pH-responsive cell delivery). When the amount of melanin produced at this time was assumed to be 100%, the amount of melanin produced by A-3 addition of the invention was 48%, B-3 was 78%, C-3 was 85%, and D-3 was 90%.

These results show that the pH-responsive lamellar delivery carrier into the cell with amphiphilic antioxidant vitamins of A-2 of the present invention had much higher inhibitory effect on melanin production than the pH-responsive lamellar delivery carrier into the cell with amphiphilic antioxidant vitamins of B-2 (control 1), non-lamellar delivery carrier into the cell with amphiphilic antioxidant vitamins of C-2 (control 2), and non-lamellar delivery carrier into the cell without amphiphilic antioxidant vitamins of D-2 (control 3).

Cellular Damage Assessment

HMV-II cell were seeded at a concentration of 1×105 cell/mL in 500 μL/well on a 6-well plate. After incubation for 24 hours, 200 μM of IBM X, a melanin-producing stimulant, was added. APS was added to 100 μM for each pH-responsive delivery carrier into cell of A-3, B-3, C-3, and D-3. 2 hours later, the cell were washed with PBS, 200 μM of IVMX was added again, and incubated for 70 hours. To this, 10 μL of Cell Counting Kit-8 was added, and the cytotoxicity of sample addition was compared by measuring absorbance at 450 nm after 1 h of incubation. As a result, cytotoxicity was confirmed by the addition of IBMX (no carrier for pH-responsive cell delivery), but no cytotoxicity was confirmed by the addition of A-3, B-3, C-3, and D-3 carriers for pH-responsive cell delivery.

Intracellular Distribution Test

HMV-II cell were seeded in glass bottom dishes at a concentration of $5\times10^4$ cell/mL in 2 mL each and incubated for 24 h (37° C.). A-2 and D-4 of the present invention were added and incubated for 2 h, washed twice in PBS and incubated for 70 h. After immobilization with 4% paraformaldehyde phosphate buffer solution for 20 min, washed twice in PBS again and observed by confocal laser microscopy. As a result, it was found that calcein, a fluorescent dye contained in A-4, was hardly taken up into the cell. In contrast, in the A-2 of this invention, calcein was taken up into the cytoplasm and nucleus, and in particular, calcein was concentrated in granular form in the cell nucleus. Calcein fluorescence intensity in the nucleus was lower than in the cytoplasm.

The above test results suggested the following. It was observed that Calcein, which is a water-soluble fluorescent substance, is not sufficiently taken up into cell by control alone, but is well taken up into cell by A-2 of the present invention. Since the encapsulated fluorescent substance was observed in the form of granules in D-2, it is considered that the D-2 liposome was taken up into the cell by endocytosis and stayed in the endosome. Furthermore, in A-2, it was confirmed that the intracellular localization of Rhodamine and Calcein was different, and it was observed that Calcein, which is a water-soluble fluorescent substance, was accumulated in the cell center. It is considered that A-2, which shows cationic properties, promotes intracellular uptake by endosomes due to its increased affinity with the cell surface, and then is released from endosomes and accumulates in the cell center.

Therefore, it is considered that the proton sponge effect of chitosan is involved in the release from endosomes. The protonation sponge effect is that when a compound that protonates in a weakly acidic environment is incorporated into the endosome, the protonation inhibits the decrease in pH in the endosome, and a large amount of protons and chloride ions enter the endosome. The influx increases the osmotic pressure inside the endosome, causing swelling and rupture of the endosome. The proton sponge effect is an effect of absorbing a large amount of protons as the pH decreases, and a large amount of his amino group-bearing cationic polymer or the like exhibits this effect. This hypothesis was proposed by Behr as a method to help it escape endosomes, especially in drug delivery. A proton pump called V-ATPase exists in the endosome membrane, and transports protons into the endosome until the pH in the endosome reaches about 5 to 6. Cationic macromolecules such as chitosan are thought to have this proton sponge effect, have a buffer range at pH 5 to 7, and absorb a large amount of proton as the endosome pH decreases. As a result, the decrease in endosome pH is suppressed, and more protons are required to decrease the pH. In addition, anions also flow in to maintain charge equilibrium inside and outside the endosome, increasing salt concentration and osmotic pressure. In order to eliminate this high osmotic pressure, a larger amount of water will flow into the endosome, and it will not be able to withstand the volume and the endosome membrane will collapse, which will promote the escape of the taken-in drug from the endosome.

Polyethylene imine (PEI) and polyamide amine dendrimers are known to have a proton sponge effect and have been widely used for efficient gene transfer.

Recently, it has been reported that the buffering capacity of chitosan is superior to that of PEI in the pH range (4.5~7) in endosomes.

It is also known that ascorbic acid sodium has an inhibitory effect on tyrosinase, a melanin-synthesizing enzyme, and inhibits the early stages of melanin synthesis. Furthermore, it has been reported that melanin is transported to dendrites as the synthesis stage progresses, suggesting that the initial stage of melanin synthesis takes place in the center of the cell. In conclusion, we believe that sodium ascorbate encapsulated chitosan-modified liposomes released from endosomes inhibited the early stages of melanin synthesis by accumulating at the center of the cell, and thus showed a remarkable inhibitory effect on melanin production.

Skin Irritation Test

In vitro skin irritation tests were conducted using cultured cell according to OECD guidelines. We used OECD GUIDELINES FOR THE TESTING OF CHEMICALS, 439. (2015) for guidelines. As a result of the skin irritation test using LabCyte EPI-MODEL as a normal dermal epidermis model (the lower the score, the higher the toxicity and the lower the safety), the scores were 3 points for 5% SLS (positive control) and 100 points for Water (negative control), 134 points for A-2, 109 points for B-2,95 points for C-2, and 91 points for D-2, and the percentage of viable cell was more than 50% for all the preparations and the skin irritation was denied. Among them, A-1 of the present invention was suggested to have the highest numerical value and the highest safety. The results of the study showed no skin irritation of the test substance in a normal skin model.

Preparation of Photoresponsive Polymers

A photoresponsive fluoropolymer was synthesized. 2,2,3, 3,4,4,4-heptafluorobutylryl (FMA) and 1'-[2-(methacryloyloxyl)ethyl]-3',3'-dimethyl-6-nitrospiro [2H-1-benzopyran-It was dissolved in DMF (ditylformamide) so that the molar ratio with 2,2'-indoline](SpMA) was 85:15. The total amount of FMA and SpMA was 10 g. MPA (3-mercaptopropionic acid) was added to the solvent after dissolution so as to be 0.028 mol times that of FMA, and AIBN (azobisisobutyronitril) was further added in an amount of 58 mg. After that, the solvent was substituted with nitrogen and degassed by ultrasonic waves, and then radical polymerization was carried out at 70° C. for 5 hours. After the temperature of the liquid after the reaction was returned to room temperature, the liquid was added dropwise to diethyl ether that had been chilled in advance, and reprecipitation purification was performed. The precipitate was then collected by filtration. This reprecipitation purification was performed twice more, and the polymer represented by Chemical formula 2 was recovered. This polymer was dialyzed against water and then freeze-dried to further purify the polymer.

[Chemical formula 2]

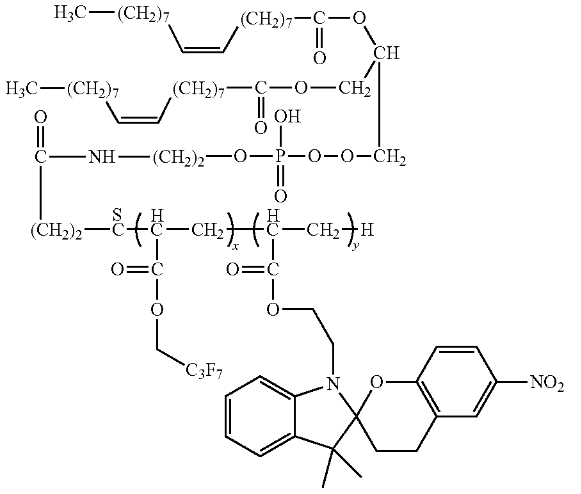

Preparation of Photoreactive Polymer-Bound Lipids

The following operation was performed to activate the polymer represented by the formula (1). That is, the molar ratio of the temperature-responsive polymer represented by the formula (1): DCC (N, N'-dicyclohexylcarbodiimide): NHS (N-hydroxysuccinimide)=1:2.5:2.5 was used. The above three substances were dissolved in methyl chloride at this molar ratio. The reaction was carried out at room temperature for 24 hours. After the reaction, the by-product dicyclohexylurea was removed by suction filtration, reprecipitation was performed with diethyl ether, and the succinyl polymer was recovered as a precipitate. This succinyl polymer and DOPE (1,2-diore oil-sn-glycero-3-phosphoethanolamine), which is a membrane fusion lipid, are dissolved in dioxane so as to have a molar ratio of 1:1 and reacted at room temperature for 24 hours. The solution after the reaction was vacuumed with an evaporator. By removing the solvent, a photoresponsive stimulus-responsive polymer-bound lipid represented by the formula (2) was prepared. This is abbreviated as DOPEMP (FMA/SpMA) Copo.

Sample A-1) Carriers for Delivery of Photoresponsive Lamella cell Containing Vitamin Derivatives (Invention). Egg yolk phosphatidylcholine 1 g, chloroform oil phosphatidylethanolamine 0.8 g, DOPEMP (FMA/SpMA) Copo. 1 g, cholesterol 0.05 g, PEG-25 phytosterol (INCI name PEG-25 Phytostanol) 0.1 g and GOVC (2-Glyceryl-3-caprylic acid ascorbic acid, glycerin: capric acid: ascorbic acid substrate bound at a weight ratio of 0.223:0.35:0.427) 0.1 g is dissolved in 200 mL chloroform, and then The solvent was removed with an evaporator to form a lamellar structure film. This was irradiated with ultraviolet rays (352 nm) for 3 minutes to block light. The following work was done under a red light source for a dark room.

1 mL of a peptide-bonded fluorescent substance solution (ovalbumin: fluorescein isothiocyanate=1:1 (isomol) mixed aqueous solution) dissolved in PBS at a concentration of 0.2 mg/mL was mixed with the above mixture. Next, 1 mL of a diluted solution of mir-125a siRNA duplex, an RNA for luciferase activity-suppressing protein biosynthesis, in PBS at a concentration of 200 nM (hereinafter simply referred to as siRNA solution) was mixed. The film was then crushed with a mixer, then sonicated, and then sized into nano-order capsules using a 400 nm pore size filter. The carriers for cell delivery were purified by gel filtration using a PD-10 column and stored in a light-shielding bottle.

Sample B-1) Carriers for temperature-responsive lamella cell delivery containing vitamins that are not vitamin derivatives (Control 1). 1 g of egg yolk-derived phosphatidylcholine, 0.8 g of dioreoil phosphatidylethanolamine, 1 g of DOPEMP (FMA/SpMA) Copo. The solvent was removed in 1 to form a lamellar structure film. This was irradiated with ultraviolet rays (352 nm) for 3 minutes to block light. The following work was done under a red light source for a dark room. To this, 1 mL of a peptide-bonded fluorescent substance solution (same as sample A-1), 0.043 g of ascorbic acid, 0.022 g of glycerin, and 1 mL of siRNA solution were mixed. Next, the film was crushed with a high-speed mixer, then ultrasonically treated, and then sized into nano-order capsules using a filter with a pore size of 400 nm. The carriers for cell delivery were purified by gel filtration using a PD-10 column and stored in a light-shielding bottle.

Sample C-1) Carriers for non-lamellar cell delivery containing vitamin derivatives (Control 2) Peptide bond fluorescent substance solution to egg yolk-derived phosphatidylcholine 1 g, dioreoil phosphatidylethanolamine 0.8 g, DOPEMP (FMA/SpMA) Copo. 1 g, cholesterol 0.05 g, PEG-25 phytostanol 0.1 g and GOVC 0.1 g. 1 mL (same as sample A-1) and 1 mL of siRNA solution were mixed. This was irradiated with ultraviolet rays (352 nm) for 3 minutes to block light. The following work was done under a red light source for a dark room. These were crushed and stirred with a high-speed mixer without going through the process of forming a lamellar structure film, then ultrasonically treated, passed through a filter having a pore size of 400 nm, and stored in a light-shielding bottle.

Sample D-1: Control for non-lamellar delivery carrier into the cell without vitamin derivatives. 1 g of egg yolk-derived phosphatidylcholine, 0.8 g of diore-oil phosphatidylethanolamine, 1 g of DOPEMP (FMA/SpMA) Copo. and 0.05 g of cholesterol and 0.1 g of PEG-25 phytostanol were mixed with 1 mL of peptide-binding fluorescent substance solution (same as sample A-1) and 1 mL of siRNA solution. This was exposed to ultraviolet light (352 nm) for 3 min and shaded. The following work was done under a red light source for a darkroom. These were crushed and stirred with a high-speed mixer without going through the process of forming lamellar structural films, then ultrasonically treated, passed through a filter with a pore size of 400 nm, and stored in a light-shielding bottle.

Measurement of Particle Size of Delivery Carrier into the Cell

The particle sizes of the cell carriers prepared for A-3, B-3, C-3, and D-3 were stored for one week and measured using a particle size analyzer (ZETASIZER Nano-ZS). The average particle size of A-1 showed a sharp single peak in the range of 314 nm (120-4550 nm), and the average particle size of B-1 showed a sharp single peak in the range of 118 nm (110-298 nm). They were exposed to ultraviolet (352 nm) or visible light (530 nm) for 3 min.

Cell Uptake Experiment

Using 6-well plates, the A-3 of the present invention, the B-3 of the control, and 125 μl of C-3 and D-3 composition solution was taken and meshed up to 1 ml in FBS medium. 5.0×10 Medium of HeLa cell (cervical cancer cell) cultured at a concentration of 4 cell/ml and meshed up as above It was incubated at 37° C. for 6 hours in a light-shielded environment, and then exposed to visible light (530 nm) for 30 The cell were irradiated for 1 min and incubated for 42 h. After incubation, the medium was removed from each of the solutions, and after incubation for 30 min with 250 μl/well of Piccadine cell lysate Lcβ (Toyo Ink) diluted 5-fold in PBS, the resulting solutions were frozen at −80° C. and centrifuged at 12,000 rpm for 5 min in a bathtub at 37° C. Then, 50 μl of Piccadine solution was added to 10 μl of the obtained supernatant, and the luminescence was measured, and the conjugation rate of nucleic acid (siRNA) was determined by measuring the intracellular luciferase activity using the following formula The siRNA, mir-125a, used in this experiment suppressed luciferase activity when taken up into the cell, so the lower the luciferase luminescence level, the more the siRNA was taken up into the cell, promoting protein synthesis and suppressing luciferase activity.

Nucleic acid (siRNA) conjugation rate=luciferase luminescence amount: C (Count per Secon d)/protein amount: P (Protein Abundant). A calibration curve was prepared using a BCA (bicinchoninic acid) assay kit for 10 μl of a medium of cervical cancer cell that did not deliver siRNA intracellularly, and then protein quantification was performed. rice field. The C/P value described above was set to 100% (control), and the RNA conjugation rate according to the above example was shown as a percentage via the luciferase activity. The results were 36% for A-1 of the present invention, 72% for B-1 of the control, 88% for C-1, and 85% for D-1. From this result, in A-1 of the present invention, the highest decrease in luciferase activity (conjugation rate) was observed, so that the effect of uptake of nucleic acid into cell was confirmed.

Measurement of Fluorescent Dye Attachment Ratio

The A-1 of the present invention prepared above and the B-1, C-1, D-1 composition liquids of the following controls were stored in a light-shielded environment under a temperature stress of 40° C. for 2 weeks, and each composition was stored. The stability of the fluorescence characteristics was investigated. That is, it was diluted 20-fold with PBS and its fluorescence intensity was measured with a fluorometer to obtain the fluorescence intensity at the time of conjugation of the peptide-bonded fluorescent substance. In addition, after adding 1% of Triton 10× to completely disintegrate the Delivery carrier into cell, the fraction of only the peptide-bonded fluorescent substance was separated by gel filtration, and the fluorescence intensity of the fraction was taken as the fluorescence intensity after heat stress. Then, the difference was calculated by subtracting the value of the fluorescence intensity at the time of conjugation from the value of the fluorescence intensity when Triton was added. For relative comparison, the hugging rate of the control was calculated with the calculated value of A-1 as 100%. As a result, A-1 of the present invention was 100%, B-1 of the control was 63%, C-1 was 11%, and D-1 was 15%. From this result, it was confirmed that A-1, which is an amphipathic antioxidant-containing lamella delivery carrier into cell of the present invention, has a significantly higher rate of uptake into cell by heat stress treatment.

(Comparison of Skin Tissue Permeability)

Using LabCyte EPI-MODEL as an epidermal skin model, artificial skin was sandwiched between Franz cell and incubated at 37° C. 1 mL of the A-1, control B-1, C-1, and D-1 composition solution of the real name invention prepared above containing the peptide-bonded fluorescent substance was administered to the donor chamber. The cell were incubated at 37° C. for 6 hours in the dark, irradiated with visible light (530 nm) for 30 minutes, and then incubated for 42 hours. Then, 10 μL of 10% TritonX was added to 150 μL of the sampling sample of the sampling port and the peptide-bonded fluorescent substance emulsified emulsified group to prepare a sample solution. Next, the fluorescence intensity of 100 μL of the sample solution was measured using a fluorometer infinite M1000, and the skin transmittance was calculated from the following formula. As a result, A-1 of the present invention was 25%, B-1 of the control was 15%, C-1 was 3%, and D-1 was 2%. From this result, it was confirmed that A-1, which is an amphipathic antioxidant vitamin-containing lamella delivery carrier into cell of the present invention, has high skin permeability. Permeation Rate (%)=(Fr/Fd)×100 (Fr: Fluorescence of sample from receptor, Fd: Fluorescence of donor)

Skin Irritation Tests:

In vitro skin irritation tests were performed on cultured cell according to OECD guidelines. The guidelines used were OECD GUIDELINES FOR THE TESTING OF CHEMICALS, 439. (2015). LabCyte EPI-MODEL was used as a normal skin epidermis model, and a skin irritation test was performed and scored. As a result (the higher the score, the higher the safety), the score is 5% SLS (positive control) 3 points, Water (negative control) 100 points, A-1 of the present invention is 111 points, B-1 was 98 points, C-1 was 87 points, and D-1 was 79 points. The viable cell rate of all the preparations was 50% or more, and skin irritation was denied. Among them, A-1 of the present invention has the highest numerical value, suggesting that it is highly safe. As a result of the test, no skin irritation of the test substance was observed in the normal skin model.

The delivery carrier into cell of the present invention was more effective than conventional ascorbic acid, Mg ascorbic acid phosphate, and all conventional ascorbic acid derivative in the following applications. Chemicals, industrial products, civil engineering and greening products, fertilizers, paints, cleaning agents, agricultural and forestry products, horticultural materials, granules, powders, miscellaneous goods, clothing, oral compositions, foods, culture compositions, animals Implementation of external compositions for drugs, photosensitizers, water treatment agents, air purifiers, pharmaceuticals, quasi-drugs, unapproved pharmaceuticals, and cosmetics. Furthermore, this composition is a chemical product, an industrial product, a civil engineering greening product, a fertilizer, a coating material, a cleaning agent, an agricultural and forestry product, a horticultural material product, a granule product, a powder product, a miscellaneous product, a clothing product, and an oral composition., Foods, culture compositions, veterinary drugs, photosensitive materials, water treatment agents, air purifiers, antioxidants.

The delivery carrier into cell of the present invention shown in the above-mentioned examples is a chemical product, an industrial product, a civil engineering greening product, a fertilizer, a paint, a cleaning agent, an agricultural and forestry product, a horticultural material product, a granule product, a powder product, a miscellaneous product, and clothing. It can also be used as an example of goods, oral compositions, foods, culture compositions, veterinary drugs, photosensitive materials, water treatment agents, and air purifiers. Furthermore, it can be used as an example of an external composition for a drug, a quasi drug, or an unapproved drug.

Formulation

The formulation including The delivery carrier into cell of the present invention was prepared in the following formulations. This water-soluble agent can be used as a liquid cosmetic, liquid quasi-drug, liquid pharmaceutical, liquid food, liquid supplement, and liquid feed additive. More specifically, it can be used as a base for the following forms of topical agents That is, the forms of topical agents that this prescription can be used are shampoo, conditioner, treatment, hair pack, hair spray, hair mist, lotion, toner, essence, hair grower, facial cleanser, cleansing lotion, lotion, emollient lotion, moisturizer lotion, milky lotion, nourishing lotion, skin moisturizer lotion, moisturizer emulsion, massage lotion, cleansing lotion, sun protector, sunscreen, makeup lotion, exfoliating smoother, elbow lotion, hand lotion, body lotion, liquid soap, pack, mask, moisturizer essence, whitening essence, UV protection essence, skin care basic makeup agent, makeup agent, perfume for skin, parfum, parfum, eau de perfume, eau de toilette, eau de cologne, kneaded perfume, deodorant lotion, deodorant powder, deodorant spray, deodorant cosmetics, bath additives, and agents for body and skin.

Preparation of Delivery Carrier into Cell of the Present Invention

Lecithin 2%, glycerin 50%, behenyl alcohol 8%, stearyl alcohol 7%, PEG-20 phytosterols 4%, cetanol 3%, phytosterols 1%, glyceryl stearate 1%, glyceryl tri(caprylic/capric acid) 2%, GOVC(2-glyceryl-3-octylascorbyl) 1%, cholesterol 0.3%, and DOPEMP(NIPAA/DMAPAA) Cop 0.2% and squalane 10% were added and kneaded with a spinning orbital agitator. To this, purified water was added and dispersed by vortexing as 100%. The liposomes were then sonicated in an ultrasound chamber for 30 min to reduce the size of the emulsion particles and then passed through a 100 nm filter to size the liposomes. The average particle size was 75 nm, and the lamellar structure was observed by electron microscopy. The liposomes were then separated and purified by gel filtration to prepare the delivery carrier into the cell of the present invention. Carriers for cell delivery with a temperature stimulus response of the present invention were prepared. This is hereinafter referred to as S-GOVC-DDS.

The total amount of lipid is 20 mg, and it is a vitamin derivative VCIP (ascorbic acid-2,3,5,6-tetraisopalmitate), DOTAP (1,2-dioreoil-3-trimethylammonium propane) and a lamella-forming surfactant DOPE: DOPEMP (NIPAA/D MAPAA) Cop was dissolved in chloroform at a molar ratio of 1:2:7. Of the DOPE dissolved in chloroform, the molar ratio between the lamellar surfactant DOPE and the lamellar surfactant DOPEMP (NIPAA/DMAPAA) Cop. which is a lamellar surfactant with a temperature-sensitive polymer expressed in formula (5) was 6.5:0.5. The solution was then transferred to an eggplant flask and the solvent was splashed in an evaporator to make a lipid film. To this lipid film, 1 ml of purified water was added and the lipid film was hydrated and then dispersed with vortex. Then, the liposomes were sonicated in an ultrasound chamber for 30 min to reduce the size of the liposomes, and then, using an extruder, the liposomes were sized through a 100 nm filter. The average particle size was 75 nm, and the lamellar structure was observed by electron microscopy. The liposomes were then separated and purified by gel filtration to prepare the delivery carrier into the cell of the present invention. Carriers for cell delivery with a temperature stimulus response of the present invention were prepared. This is hereinafter referred to as S-VCIP-DDS.

In the above examples, the following three invention stimulus-responsive delivery carriers into cell were created. That is, temperature-stimulated delivery carrier into cell s (SGOVC-DDS and S-VCIP-DDS), pH-stimulated delivery carrier into cell s (pH-GOVC-Chito), and light-stimulated delivery carrier into cell s (DOPEMP (FMA/SpMA)). Cop). The following formulations were made using these three types of delivery carriers into cell of the present invention. Unless otherwise stated, all the units "%" are shown in % (weight/weight) in the publication of the present invention including the following formulation example. In the following pharmaceutical formulations, a mixture of S-GOVC-DDS and S-VCIP-DDS at a mass ratio of 50%:50% is described as S-GOVC-DDS/S-VCIP-DDS. Furthermore, a mixture of S-GOVC-DDS, S-VCIP-DDS, pH-GOVC-Chito, and DOPEMP (FMA/SpMA) Cop at a mass ratio of 25%: 25%:25%:25% is described as S-VCIP-DDS/pH-GOVC-Chito/DOPEMP(FMA/SpMA)Cop.

Liquid Formulation (1)S-GOVC-DDS/S-VCIP-DDS: 0.5, (2)glycerin: 6.5, (3) 1,3-butylene glycol: 1.0, (4) phenoxyethanol: 0.5, (5) fragrance complex: 0.1, (6) essential oil complex: 0.1, (6) purified water: remaining amount (7) citric acid: 1.0, (8) pH was adjusted to 7 with NaOH.

Emulsion Formulation (1) Polyoxyethylene (10EO.) Sorbitan 1.0 Monostearate: 0.5, (2) Polyoxyethylene (60EO.) Sorbitan 0.5 Tetraoleate: 0.5, (3)) Glyceryl monostearate: 1.0, (4) F3:0.1, (5) Behenyl alcohol: 0.5, (6) Sorbitan: 8.0, (7) Beech sprout extract 1:2.0, (8) Grape extract 2:2.0, (9) Comfrey extract 3:2.0, (10) Dipotassium glycyrrhizinate 4:0.02, (11)S-GOVC-DDS/S-VCIP-DDS: 1.0, (12) Carboxyvinyl polymer: 0.1, (13) Sodium hydroxide: 0.05, (14) Ethyl alcohol: 5.0, (15) Purified water: Remaining amount, (16)) Appropriate amount of preservative, (17) Appropriate amount of fragrance (pH was adjusted to 7 f 1 with 1% citrate and NaOH. The total transition metal content of the above emulsion was 100 ppm or less).

Prescribing Ointment (1) stearic acid: 18.0, (2) cetanol: 4.0, (3) triethanolamine: 2.0, (4) F5: 1.0, (5) nettle extract: 1.0.05, (6) hawthorn extract: 2.0.05, (7) bodaiju extract: 3.0.05, (8) N,N'-diacetylcystin dimethyl 4.0.01, (9) tranexamic acid: 5.0.2, (10) purified water: remaining amount (pH was adjusted to 7±1 with 1% citric acid and NaOH. (The total transition metal content of the above ointment was less than 100 ppm). 1 Maruzen Seiyaku 2 Maruzen Seiyaku 3 Maruzen Seiyaku 4 Sigma Seiyaku 5 Sigma Seiyaku Gel Formulation (1) Carboxy vinyl polymer 1: 1.0, (2) triethanolamine: 1.0, (3) 1,3-butylene glycol: 10.0, (4) F6: 0.5, (5) aloe extract 2: 0.5, (6) allantoin 3: 1.0, (7)S-GOVC-DDS/S-VCIP-DDS: 2.0, (8) 2-hydroxy-4-methoxybenzophenone-5-sodium sulfate 5: 3.0, (9) purified water: remaining amount (pH was adjusted to 7±1 with 1% citric acid and NaOH). (The total transition metal content of the above gel ointment was less than 100 ppm).

Cream Formulation (1) polyoxyethylene (40EO) monostearate: 2.0, (2) glycerin monostearate (self-emulsifying type) 1: 5.0, (3) stearic acid: 5.0, (4) Behenyl alcohol: 0.5, (5) squalane: 15.0, (6) cetyl isooctanoate: 5.0, (7) 1,3-butylene glycol: 5.0, (8) F7: 1.0, (9) Birch extract 2: 0.1, (10) Saxifraga extract 3: 0.2, (11)S-GOVC-DDS/S-VCIP-DDS: 1.0, (12) Paramethoxycinnabar 2-ethylhexyl acid 5: 5.0, (13) riboflavin 6: 0.05, (14) cysteine Powder Prescription (1) Lanolin: 7.0, (2) liquid paraffin: 5.0, (3) stearic acid: 2.0, (4) cetanol: 1.0, (5) sunflower oil 1: 1.0, (6) glycerin: 5.0, (7) triethanolamine: 1.0, (8) carboxymethylcellulose: 0.7, (9) purified water: residual amount, (10) mica: 15.0, (11) Talc: 6.0, (12) Titanium oxide: 3.0, (13) Color pigment: 6.0, (14) F5: 0.5, (15) Tormentilla extract 3: 0.5, (16)S-GOVC-DDS/S-VCIP-DDS: 0.2, (17) Stearyl glycyrrhetinate 5: 0.1, (18) Preservative 0.5, (19) Perfume appropriate amount (1% citric acid and NaOH The pH was adjusted to 7±1. The total transition metal content was less than 100 ppm.)

Prescription of UV Care Agent (1) stearic acid: 2.0, (2) cetanol: 1.0, (3) polyoxyethylene sorbitan monooleate (20EO): 0.5, (4) sorbitan sesquioleate: 0.1. 5, (5) Cetyl 2-ethylhexanoate: 12.0, (6) Shea fat 1: 2.0, (7) Sesame oil 2: 1.0, (8) Orgonum extract 3: 0.1, (9) F3: 0.5, (10) ergocalciferol 5: 0.1, (11)S-GOVC-DDS/S-VCIP-DDS: 3.0, (12) 2-ethylhexyl paramethoxycinnamate 7: 8.0, (13) 2-hydroxy-4-methoxybenzophenone 8: 2.0, (14) 1,3-butylene glycol: 10.0, (15) carboxyvinyl polymer: 0.2, (16)) Purified water: residual amount, (17) proper amount of preservative, (18) titanium oxide: 3.0 (19) Triethanolamine: 0.5. (20) Perfume Appropriate amount (pH adjusted to 7±1 with 1% citric acid and NaOH. The total transition metal content of the sunscreen emulsion was 100 ppm or less.)

Pack Prescription (1) polyvinyl alcohol: 20.0, (2) ethyl alcohol: 20.0, (3) glycerin: 5.0, (4) kaolin: 6.0, (5)S-GOVC-DDS/S-VCIP-DDS: 0.5, (6) F2: 0.5, (7) lily extract 3: 0.05, (8) resorcin 4: 0.02, (9) riboflavin 5: 0.1, (10) tranexamic acid 6: 0.5, (11) preservative: 0.2, (12) fragrance: 0.1, (13) purified water: residue (pH was adjusted to 7±1 with 1% citric acid and NaOH. The total transition metal content of the above packs was less than 100 ppm).

Detergent Formulation (1) Stearic acid: 10.0, (2) palmitic acid: 8.0, (3) myristic acid: 12.0, (4) lauric acid: 4.0, (5) oleyl alcohol: 1.5, (6) purified lanolin: 1.0, (7) astaxanthin 1: 0.0005, (8) fragrance: 0.1, (9) preservative: 0.2, (10) glycerin: 18.0, (11) potassium hydroxide: 6.0, (12)S-GOVC-DDS/S-VCIP-DDS: 0.5, (13) Sapon grass extract: 0.5, (14) dipotassium glycyrrhizate: 4.0.2, (15) L-L-ascorbate palmitate: 5.0.05, (16) purified water: residue (pH was adjusted to 7±1 with 1% citric acid and NaOH. (The total transition metal content of the above detergent was less than 100 ppm).

Composition for Oral Use

A vitamin premix comprising 92.7 mass % of animal fat with a melting point of 28±3° C., comprising 50 mass % of chicken oil and 50 mass % of pork oil, 0.9 mass % of enzyme, 1.0% of vitamin premix with 1% of S-GOVC-DDS/S-VCIP-DDS, 0.9% of fungal powder, and 4.5 mass % of flavoring agent, was stirred and dispersed for 2 hours in a 200 L stirring and mixing machine manufactured by Meiji Machine Co. The oral compositions of the present invention are embodiments of feeds, feed additives, animal medicines, foods, food additives, functional foods, functional foods, and oral animal medicines.

Tablets

The following ingredients were uniformly mixed in the following composition ratios according to the normal method, and tablets of 400 mg per grain were made by tableting. Reduced malt syrup: 17%, agar: 12%, silicon dioxide: 1%, sucrose fatty acid ester: 3%, freeze-dried powder of S-GOVC-DDS/S-VCIP-DDS: 1%, powdered cellulose: residue Capsules:

The soft capsule was filled with 300 mg of lyophilized S-GOVC-DDS/S-VCIP-DDS (5% freeze-dried powder and 95% medium-chain fatty acid triglyceride) into 100 mg of soft capsule skin (70% gelatin and 25% glycerin) according to the normal method, and 440 mg of each soft capsule was obtained.

Drinks:

S-GOVC-DDS/S-VCIP-DDS: 80 g, royal jelly: 1 g, liquid sugar: 1000 g, S-GOVC-DDS/S-VCIP-DDS: 80 g Sodium DL-tartaric acid: 1 g, citric acid: 10 g, cyclodextrin: 25 g, potassium chloride: 2 g, magnesium sulfate: 1 g.

Liquid Formulation:

(1)S-GOVC-DDS/S-VCIP-DDS/PH-GOVC-CHITO/DOPEMP(FMA/SPMA)COP: 0.5, (2) glycerin 6.5, (3) 1,3-butylene glycol 1.0, (4) phenoxyethanol 0.5, (5) fragrance complex 0.1, (6) essential oil complex 0.1, (6) purified water: remaining amount (7) citric acid 1.0 (8) The pH was adjusted to 7 with NaOH.

Emulsion Formulation:

(1) Polyoxyethylene (10E. O.) Sorbitan 1.0 Monostearate: 0.5, (2) (2) Polyoxyethylene (60 E. O.) sorbit: 0.5 Tetraoleate: 0.5, (3) 5, (6) Squalane: 8.0, (7) Beech bud extract 1: 2.0, (8) Grape extract 2: 2 (9) Comfrey extract 3: 2.0, (10) Dipotassium glycyrrhizate 4: 0.02 (11)S-GOVC-DDS/S-VCIP-DDS/PH-GOVC-CHITO/DOPEMP(FMA/SPMA) COP: 1.0, (12)carboxy vinyl polymer: 0 (13) Sodium hydroxide: 0.05, (14) Ethyl alcohol: 5.0, (15) Purified water: Remaining amount, (16) Preservative: (16) Preservative: (17) Fragrance: (1)Citric acid and NaOH, pH 7±7 It was adjusted to 1. (The total transition metal content of the above emulsions was less than 100 ppm).

Prescribing Ointment:

(1) stearic acid: 18.0, (2) cetanol: 4.0, (3) triethanolamine: 2.0, (4) F5: 1.0, (5) nettle extract: 1.0.05, (6) hawthorn extract: 2.0.05, (7) bodaiju extract: 3.0.05, (8) N,N'-diacetylcystin dimethyl 4.0.01, (9) tranexamic acid: 5.0.2, (10) purified water: remaining amount (pH was adjusted to 7±1 with 1% citric acid and NaOH. (The total transition metal content of the above ointment was less than 100 ppm). 1 Maruzen Seiyaku 2 Maruzen Seiyaku 3 Maruzen Seiyaku 4 Sigma Seiyaku 5 Sigma Seiyaku Gel Formulation:

(1) Carboxyvinyl polymer 1: 1.0, (2) triethanolamine: 1.0, (3) 1,3-butylene glycol: 10.0, (4) F6: 0.5, (5) aloe extract 2: 0.5, (6) allantoin 3: 1.0, (7)S-GOVC-DDS/S-VCIP-DDS/PH-GOVC-CHITO/DOPEMP(FMA/SPMA)COP: 2.0, (8) 2-hydroxy-4-methoxybenzophenone-5-sodium sulfate 5: 3.0, (9) purified water: residue (pH was adjusted to 7±1 with 1% citric acid and NaOH. (The total transition metal content of the above gel ointment was less than 100 ppm).

Cream Formula:

(1) polyoxyethylene (40EO) monostearate: 2.0, (2) glycerin monostearate (self-emulsifying type) 1: 5.0, (3) stearic acid: 5.0, (4) Behenyl alcohol: 0.5, (5) squalane: 15.0, (6) cetyl isooctanoate: 5.0, (7) 1,3-butylene glycol: 5.0, (8) F7: 1.0, (9) Birch extract 2: 0.1, (10) Saxifraga extract 3: 0.2, (11)S-GOVC-DDS/S-VCIP-DDS/PH-GOVC-CHITO/DOPEMP (FMA/SPMA) COPO: 1.0, (12) 2-ethylhexyl paramethoxycinnamate 5: 5.0, (13) Riboflavin 6: 0.05, (14) Cysteine Wet Powder Formulation: (1) Lanolin: 7.0, (2) liquid paraffin: 5.0, (3) stearic acid: 2.0, (4) cetanol: 1.0, (5) sunflower oil 1: 1.0, (6) glycerin: 5.0, (7) triethanolamine: 1.0, (8) carboxymethylcellulose: 0.7, (9) purified water: residual amount, (10) mica: 15.0, (11) Talc: 6.0, (12) Titanium oxide: 3.0, (13) Color pigment: 6.0, (14) F5: 0.5, (15) Tormentilla extract 3: 0.5, (16)S-GOVC-DDS/S-VCIP-DDS/PH-GOVC-CHITO/DOPEMP (FMA/SPMA) COPO: 0.2, (17) Stearyl glycyrrhetinate 5: 0.1, (18) Preservative 0.5, (19) Appropriate amount of fragrance (pH was adjusted to 7±1 with 1% citric acid and NaOH. Total transition metal content was 100 ppm or less.)

Sunscreen Prescription:

(1) stearic acid: 2.0, (2) cetanol: 1.0, (3) polyoxyethylene sorbitan monooleate (20EO): 0.5, (4) sorbitan sesquioleate: 0.1. 5, (5) Cetyl 2-ethylhexanoate: 12.0, (6) Shea fat 1: 2.0, (7) Sesame oil 2: 1.0, (8) Orgonum extract 3: 0.1, (9) F3: 0.5, (10) Ergocalciferol 5: 0.1, (11)S-GOVC-DDS/S-VCIP-DDS/PH-GOVC-CHITO/DOPEMP (FMA/SPMA) COPO: 3 0.0, (12) 2-ethylhexyl paramethoxycinnamate 7: 8.0, (13) 2-hydroxy-4-methoxybenzophenone 8: 2.0, (14) 1,3-butylene glycol: 10.0, (15) Carboxyvinyl polymer: 0.2, (16) Purified water: Residual, (17) Preservative appropriate amount, (18) Titanium oxide: 3.0, (19) Triethanolamine: 0.5. (20) Perfume Appropriate amount (pH adjusted to 7±1 with 1% citric acid and NaOH. The total transition metal content of the sunscreen emulsion was 100 ppm or less.)

Pack Prescription:

(1) polyvinyl alcohol: 20.0, (2) ethyl alcohol: 20.0, (3) glycerin: 5.0, (4) kaolin: 6.0, (5)S-GOVC-DDS/S-VCIP-DDS/PH-GOVC-CHITO/DOPEMP (FMA/SPMA) COPO: 0.5, (6) F2: 0.5, (7) Lily extract 3: 0.05, (8) Resorcinol 4: 0.02, (9) riboflavin 5: 0.1, (10) tranexamic acid 6: 0.5, (11) preservative: 0.2, (12) fragrance: 0.1, (13) purified water: residual amount (The pH was adjusted to 7±1 with 1% citric acid and NaOH. The total transition metal content of the pack was less than 100 ppm.)

Detergent Formulation:

(1) stearic acid: 10.0, (2) palmitic acid: 8.0, (3) myristic acid: 12.0, (4) lauric acid: 4.0, (5) oleyl alcohol: 1.5, (6) purified lanolin: 1.0, (7) astaxanthin 1: 0.005, (8) flavor: 0.1, (9) preservative: 0.2, (10) glycerin: 18.0, (11)) Potassium hydroxide: 6.0, (12)S-GOVC-DDS/S-VCIP-DDS/PH-GOVC-CHITO/DOPEMP (FMA/SPMA) COPO: 0.5, (13) Soapwort extract 3: 0.5, (14) dipotassium glycyrrhizinate 4: 0.2, (15) LL-ascorbic acid palmitate 5: 0.05, (16) purified water: residual amount (pH is 1% with citric acid and NaOH) It was adjusted to 7±1. The total transition metal content of the above-mentioned detergent was 100 ppm or less.)

Composition for Oral Use

The oral composition of this invention was obtained by agitating and dispersing 92.7% (w/w) of animal fat with a melting point of 28±3° C., comprising 50%(w/w) of chicken oil and 50% (w/w) of pork oil, 0.9% of enzyme, 1.0% (w/w) of vitamin premix with 1% of S-GOVC-DDS/S-VCIP-DDS/PH-GOVC-CHITO/DOPEMP(FMA/SPMA)COP, 0.9% of powdered living bacterial agent, and 4.5% of flavoring agent in a 200 L agitating mixer manufactured by Meiji Kikai for 2 hours. The oral compositions of the present invention are embodiments of feeds, feed additives, animal medicines, foods, food additives, functional foods, functional foods, and oral animal medicines.

Tablets:

The following ingredients were uniformly mixed in the following composition ratios according to the normal method, and tablets of 400 mg per grain were made by tableting. Reduced malt syrup: 17%, agar: 12%, silicon dioxide: 1%, sucrose fatty acid ester: 3%, freeze-dried powder of S-GOVC-DDS/S-VCIP-DDS/PH-GOVC-CHITO/DOPEMP(FMA/SPMA)COP: 1%, powdered cellulose: residue Capsules:

The soft capsule was filled with 300 mg of S-GOVC-DDS/S-VCIP-DDS/PH-GOVC-CHITO/DOPEMP(FMA/SPMA)COP lyophilized powder (5%) and medium-chain fatty acid triglyceride (95%) into 100 mg of soft capsule skin (gelatin 70%, glycerin 25%) according to the normal method, and 440 mg of soft capsule was obtained.

Drinks:

S-GOVC-DDS/S-VCIP-DDS/PH-GOVC-CHITO/DOPEMP(FMA/SPMA)COP: 80 g, royal jelly: 1 g, liquid sugar: 1000 g, Sodium DL-tartaric acid: 1 g, citric acid: 10 g, cyclodextrin: 25 g, potassium chloride: 2 g, magnesium sulfate: 1 g.

Stability Test:

All of the above formulations of the present invention were tested for stability at 40° C. for 6 months. The evaluation of the stability test was made by evaluating the color change of the pharmaceutical product, the occurrence of precipitation, and the occurrence of odor with the following scores, and the average score was calculated and compared. The evaluation was individually evaluated by 10 men and women between the ages of 20 and 50, and he calculated the average score. Color change score: No change: 0 points, change observed: 2 points, drastic change observed: 3 points. Score of separation occurrence: No occurrence: 0 points, precipitation is observed: 2 points, severe precipitation is observed: 3 points. Score of change in odor: No change at all: 0 points, change is observed: 2 points, drastic change is observed: 3 points.

As a result of these tabulations, in the above formulation of the present invention, no change with time was observed in all of the color change, the occurrence of precipitation, and the change in odor, and the score was 0. From this result, the formulation of the present invention was excellent, the stability was proven.

Add 0.005 g of each of the lamella-forming lipids listed in Table 4 above and finally 2 g by lecithin. It is adjusted and added to the polyhydric alcohols, synthetic antioxidants, UV absorbers, and preservatives and the preservatives in Table 6. Add 0.005 g of each of the active ingredients of the invention in Table 8 and was finally adjusted to reach 50 g with glycerin. In addition, 8 g of behenyl alcohol, 7 g of stearyl alcohol, PEG-20 Phytosterol 4 g, cetanol 3 g, phytosterols 1 g, glyceryl stearate 1 g, 2 g of tri(caprylic/capric acid) glyceryl, 2 g of GOVC (2-glyceryl-3-) Octyl ascorbyl) 1 g, cholesterol 0.3 g, and DOPEMP (NIPAA/DMAPAA) Cop and 0.005 g of each of the lipids listed in Table 3 above, and finally It was adjusted and added with squalane to reach 30 g and kneaded with a self-rotating agitator. Purified water was added to the mixture and it was dispersed in a vortex as 100 g. The mixture was then sonicated in an ultrasonic bath for 30 minutes to reduce the size of the emulsion particles. The emulsion was then sonicated in an ultrasonic bath for 30 minutes to reduce the size of the emulsified particles, and then 100 The size of the liposomes was adjusted through a 1.5 nm filter. The average size of the particles was 79 nm, and lamellar structures were observed by electron microscopy. The liposomes were then separated and purified by gel filtration to produce the delivery carrier into the cell of the present invention. were prepared. A temperature-stimulus-responsive delivery carrier into the cell of the present invention was prepared. Next, this delivery carrier into the cell was used to make a liquid formulation. The formulation was as follows: (1) The cell delivery system was prepared using the above mentioned delivery carrier into the cell. The formula is as follows: (1) The above delivery carrier into the cell: 0.5, (2) glycerin 6.5, (3) 1,3 butylene glycol 1.0, (4) phenoxyethanol 0.5, (5) fragrance complex 0.1, (6) essential oil complex 0.1, (6) purified water: remaining (7) citric acid 1.0, the pH was adjusted to 7 with (8) NaOH.

The above-mentioned all formulations can be used for medicines, quasi-drugs, cosmetics, supplements, veterinary drugs, and miscellaneous goods. The above-mentioned all formulations can be used as topical, oral, suppository, oral, drink, poultice, pack, spray, injection, dressing, liquid, ointment, aerosol, powder form, mold, cream, topical dispersant, dispersant, granule, tablet, soft capsule, round, board form, troche, paste, solid form, moisturizer, and tic-like form. Furthermore, these formulations had the effects shown in Table 9 as cosmetics and quasi-drugs.

Carrier for different temperature-stimulus-responsive cell delivery One of the temperature-responsive delivery carriers of the present invention, DOPEMP (NIPAA/DMAPAA) Cop is a temperature-stimulus-responsive substance having a low critical melting temperature of 37-42° C., which is approximately equal to body temperature. Hereinafter, it is referred to as body temperature change type. Further, one of the other DOPEMP (NIPAA/DMAPAA) Cops is a temperature-stimulus-responsive substance having a high critical melting temperature of 45-60° C., which is higher than the body temperature. It is called high temperature change type. The effects of the two carriers were demonstrated in the following examples.

The method of preparing the carrier was the same: 1 g of egg yolk-derived phosphatidylcholine, 0.8 g of dioleoyl phosphatidylethanolamine, 3 g of DOPEMP (NIPAA/DMAPAA) Cop. and 0.05 g of cholesterol, 0.1 g of PEG-25 Phytostanol (INCI name: PEG-25 Phytostanol), and 0.1 g of GOVC (an amphiphilic vitamine derivative comprising 2-glyceryl-3-Caprylyl ascorbate, glycerin:Caprylyl:ascorbate in the weight ratio of 0.223:0.35:0.427) were dissolved in 200 mL chloroform, and the solvent was removed with an evaporator to form a lamellar structural film. To this, 1 mL of a solution of peptide-binding fluorophores dissolved in PBS at a concentration of 0.2 mg/mL (ovoalbumin:fluorescein:isothiocyanate=1:1 (equal moles) mixed with 1 mL of mir-125a siRNA duplex, which biosynthesizes proteins that inhibit luciferase activity in cell as nucleic acids, diluted in PBS at a concentration of 200 nM (hereinafter referred to as siRNA solution). Next, the films were crushed in a mixer, then sonicated, and further sized into nano-order capsules using a 400 nm pore size filter; the carriers for cell delivery were purified by gel filtration using a PD-10 column. Comparison of skin tissue permeability: A LabCyte EPI-MODEL was used as an epidermal skin model, and 1 mL of the compositional solution containing 1% by weight of the carriers of the body temperature- and high-temperature-change forms of the invention prepared as described above, containing fluorescent substances prepared by placing artificial skin in a Franz Cell and incubating at 37° C., was administered into a donor chamber, and incubated at 37° C. in the body temperature model and 45° C. in the steamed towel model, respectively, shaded by light for 0.5 hours, irradiated with visible light (530 nm) for 30 minutes, and incubated for 42 hours thereafter. Then, 10 μL of 10% TritonX was added to 150 μL of the sampling sample and peptide-binding fluorescent substance conjugated emulsions at the sampling port as a reference sample solution. The fluorescence intensity of 100 μL of sample solution was measured using a fluorometer, infinite® M1000, and the skin transmittance was calculated from the following equation. As a result, the absorption rate by fluorescence intensity at 37° C. incubation was 8% for the body temperature change type and 4% for the high temperature change type. From this result, at the body temperature model temperature of 37° C., the body temperature change type showed twice higher fluorescence intensity than the high temperature change type. It means that the absorption rate of the fluorescent dye transported into the cell by the temperature-changing carrier was higher than that of the high-temperature changing type. On the other hand, in the experiment at 45° C. incubation, the body temperature change type was 3% and the high temperature change type was 9%. At this steamed towel model temperature of 45° C., the high temperature change type showed three times higher fluorescence intensity than the body temperature change type. A part of the human body can be brought to 45° C. with a steaming towel, infrared, high frequency and low frequency phototherapy devices. It was confirmed that in such a high temperature environment, the high temperature change type carrier of the present invention exhibits higher drug transport capacity than the body temperature change type carrier.

Stability Tests of the Different Vitamin Derivatives

Stability tests were conducted on different vitamin derivatives of the delivery carrier into the cell of the present invention. The carrier was prepared by dissolving of following ingredients in 200 mL chloroform. 1 g of egg yolk-derived phosphatidylcholine, 0.8 g of dioleoylphosphatidylethanolamine, 3 g of DOPEMP (NIPAA/DMAPAA) Cop and 0.05 g of cholesterol, 0.1 g of PEG-25 phytostanol (INCI name: PEG-25 Phytostanol) and 0.1 g of different vitamin derivatives in next sentence. And then removing the solvent with an evaporator to form a lamellar structural film. To this, 1 mL of a solution of peptide-binding fluorophores dissolved in PBS at a concentration of 0.2 mg/mL (a mixture of oboalbumin and fluorescein isothiocyanate=1:1 (equal moles)) was mixed with 1 mL of the solution diluted in PBS (hereinafter referred to as the fluorescent solution). Next, the films were crushed with a mixer, then sonicated, and further sized into nano-ordered capsules using a 100 nm pore size filter, and the capsules were observed under normal optical and polarized light microscopy to confirm that the carriers encapsulated fluorescent dyes under the microscope and that malatase cross polarization was present under the polarized light microscope. After 6 months of storage in an environment of 40° C. and 80% humidity, the carrier state was observed under an ordinary optical microscope and a polarized light microscope. At this time, only those vitamin derivatives for which we could confirm that the carrier did not break down and that the carrier still contained the fluorescent dye under the microscope as it did at the start of the test and that maltase cross polarization was present under the polarizing microscope were classified as ○ group vitamin derivatives that could be effectively used in the present invention, and those for which either of these could not be confirmed were classified as X group vitamin derivatives.

Vitamin derivatives of group ○

Vitamin derivatives listed in Table 2.

Vitamin derivatives of group X ascorbic acid-2-sulfate, ascorbic acid-2-sulfate K, ascorbic acid-2-phosphate Na, ascorbic acid-2-phosphate Mg, ascorbic acid-2-phosphate-6-palmitate Na, ascorbyl stearate, isostearyl ascorbyl Phosphate 2Na, Ascorbyl isostearate, Ascorbyl palmitate, Ascorbyl dipalmitate, Ascorbyl isopalmitate Phosphate 3Na, Tocopheryldimethylglycine, Tocopheryldimethylglycine HCl Lipid Stability Test We tested the stability of our Delivery carrier into cell in different lipids. The carrier was prepared by adding 1 g of egg yolk-derived phosphatidylcholine, 0.8 g of dioleoylphosphatidylethanolamine, 3 g of DOPEMP (NIPAA/DMAPAA) Cop. 3 g, 0.05 g of cholesterol, 0.1 g of PEG-25 phytostanol (INCI name PEG-25 (INCI name PEG-25 Phytostanol), 0.1 g of cholesterol, 0.5 g of lipid, and 0.1 g of GOVC (2-glyceryl-3-caprylic acid ascorbic acid, a vitamin derivative) were dissolved in 200 mL chloroform, and the solvent was removed by evaporator to form a lamellar structure film. To this solution, 1 mL of peptide-linked fluorescent substance solution (aqueous mixture of ovoalbumin:fluorescein isothiocyanate=1:1 (equimolar)) dissolved in PBS at a concentration of 0.2 mg/mL was mixed with 1 mL of the solution diluted in PBS (hereinafter referred to simply as the fluorescent solution). The film was then crushed with a mixer, followed by sonication, and further sizing into nano-order capsules using a 100 nm pore size filter. The state of the capsules was observed by conventional optical microscopy and polarized light microscopy, and it was found that the carrier encapsulated the fluorescent dye under the microscope and that there was maltase cross polarization under polarized light microscopy. We confirmed that the carrier contained the fluorescent dye under the microscope and that maltase cross polarization was present under the polarized light microscope. After 6 months of storage at 40° C. and 80% humidity, the state of the carrier was observed using a conventional optical microscope and a polarizing microscope. It was confirmed that the carrier did not break down and still contained the fluorescent dye under the microscope as it did at the start of the test, and that maltase cross polarization was present under the polarizing microscope. Lipids for which the attenuation rate of the vitamin derivative was suppressed to less than 10% and the vitamin derivative was kept stable are listed in Table 3 as lipids that are particularly useful for the present invention.

Stability Test of Lipids with Surfactant Action

The stability of The delivery carrier into cell was tested in lipids with different surfactant activity. The carrier was prepared by combining 1 g of egg yolk-derived phosphatidylcholine, 0.8 g of dioleoylphosphatidylethanolamine, 3 g of DOPEMP (NIPAA/DMAPAA) Cop. 3 g, 0.05 g of cholesterol, 0.5 g of surfactant lipid, and 0.1 g of GOVC (2-glyceryl-3-caprylic ascorbate, a vitamin derivative). (a vitamin derivative, 2-glyceryl-3-caprylic acid ascorbic acid) were dissolved in 200 mL chloroform, and the solvent was removed by evaporator to form a lamellar structure film. To this solution, 1 mL of peptide-linked fluorescent substance solution (aqueous mixture of ovoalbumin:fluorescein isothiocyanate=1:1 (equimolar)) dissolved in PBS at a concentration of 0.2 mg/mL was mixed with 1 mL of the solution diluted in PBS (hereinafter referred to simply as the fluorescent solution). The film was then crushed with a mixer, followed by sonication, and further sizing into nano-order capsules using a 100 nm pore size filter. The state of the capsules was observed by conventional optical microscopy and polarized light microscopy, and it was found that the carrier encapsulated the fluorescent dye under the microscope and that there was maltase cross polarization under polarized light microscopy. We confirmed that the carrier contained the fluorescent dye under the microscope and that maltase cross polarization was present under the polarized light microscope. After 6 months of storage at 40° C. and 80% humidity, the state of the carrier was observed using a conventional optical microscope and a polarizing microscope. It was confirmed that the carrier did not break down and still contained the fluorescent dye under the microscope as it did at the start of the test, and that maltase cross polarization was present under the polarizing microscope. The lipids that were found to be particularly useful in the present invention are listed in Table 4, and those that were not found to be stable were excluded as having stability problems.

Stability Test of Stimulus-Responsive Substances

In this study, we tested the stability of The delivery carrier into cell in different stimuli-responsive substances. The carrier was prepared by dissolving 1 g of egg yolk-derived phosphatidylcholine, 0.8 g of dioleoylphosphatidylethanolamine, 3 g of different stimuli-responsive substances, 0.05 g of cholesterol, and 0.1 g of GOVC (2-glyceryl-3- caprylate ascorbic acid, a vitamin derivative) in 200 mL of chloroform. After dissolving in chloroform, the solvent was removed using an evaporator to form a lamellar structure film. To this solution, 1 mL of peptide-linked fluorescent substance solution (aqueous mixture of ovoalbumin:fluorescein isothiocyanate=1:1 (equimolar)) dissolved in PBS at a concentration of 0.2 mg/mL was mixed with 1 mL of the solution diluted in PBS (hereinafter referred to simply as the fluorescent solution). The film was then crushed with a mixer, followed by sonication, and further sizing into nano-order capsules using a 100 nm pore size filter. The state of the capsules was observed by conventional optical microscopy and polarized light microscopy, and it was found that the carrier encapsulated the fluorescent dye under the microscope and that there was maltase cross polarization under polarized light microscopy. We confirmed that the carrier contained the fluorescent dye under the microscope and that maltase cross polarization was present under the polarized light microscope. After 6 months of storage at 40° C. and 80% humidity, the state of the carrier was observed using a conventional optical microscope and a polarizing microscope. It was confirmed that the carrier did not break down and still contained the fluorescent dye under the microscope as it did at the start of the test, and that maltase cross polarization was present under the polarizing microscope. Table 5 lists the stimuli-responsive substances that are particularly useful in the present invention as those for which the decay rate of the vitamin derivative was suppressed to 20% or less and the vitamin derivative was kept stable. Those that could not be confirmed in either case were excluded as having stability problems.

Stability Test of Emulsion Stabilizer

The stability of The delivery carrier into cell was tested in emulsion stabilizers selected from polyhydric alcohols, synthetic antioxidants, UV absorbers, and preservatives. The carrier was prepared by adding 1 g of egg yolk-derived phosphatidylcholine, 0.8 g of dioleoylphosphatidylethanolamine, 3 g of DOPEMP (NIPAA/DMAPAA) Cop. 3 g of cholesterol, 0.05 g of GOVC (a vitamin derivative, 2-glyceryl-3-caprylate (2-glyceryl-3-caprylic acid ascorbic acid) were dissolved in 200 mL chloroform, and the solvent was removed by evaporator to form a lamellar film. To this, 0.5 g of an emulsion stabilizer selected from polyhydric alcohols, synthetic antioxidants, UV absorbers, and preservatives, and 1 mL of a peptide-linked fluorescent substance solution (a mixture of ovoalbumin:fluorescein isothiocyanate=1:1 (equimolar)) dissolved in PBS at a concentration of 0.2 mg/mL were mixed with 1 mL of the solution diluted in PBS. The film was then crushed with a mixer. The film was then crushed with a mixer, followed by sonication, and further sizing into nano-order capsules using a 100 nm pore size filter. We confirmed that the carrier contained the fluorescent dye under the microscope and that maltase cross polarization was present under the polarized light microscope. After 6 months of storage at 40° C. and 80% humidity, the state of the carrier was observed using a conventional optical microscope and a polarizing microscope. It was confirmed that the carrier did not break down and still contained the fluorescent dye under the microscope as it did at the start of the test, and that maltase cross polarization was present under the polarizing microscope. The emulsification stabilizers that were able to suppress the decay rate of the vitamin derivative to 10% or less and maintain the stability of the vitamin derivative are listed in Table 6 as emulsification stabilizers that are particularly useful for the present invention, and those that could not be confirmed in either case were excluded from the list as having stability problems.

Stability tests for different modified chain materials within the stimulus-responsive polymers We tested the stability of The delivery carrier into cell in different modified chain substances within the stimuli-responsive polymer. The carrier was prepared by dissolving 1 g of egg yolk-derived phosphatidylcholine, 0.8 g of dioleoylphosphatidylethanolamine, 3 g of DOPEMP (NIPAA/DMAPAA/modified chain substance), 0.05 g of cholesterol and 0.1 g of GOVC (2-glyceryl-3-caprylic acid ascorbic acid, a vitamin derivative) in 200 mL chloroform. 3 g, 0.05 g of cholesterol, and 0.1 g of GOVC (2-glyceryl-3-caprylic acid ascorbic acid, a vitamin derivative) were dissolved in 200 mL chloroform, and the solvent was removed using an evaporator to form a lamellar film. To this solution, 1 mL of peptide-linked fluorescent substance solution (aqueous mixture of ovoalbumin:fluorescein isothiocyanate=1:1 (equimolar)) dissolved in PBS at a concentration of 0.2 mg/mL was mixed with 1 mL of the solution diluted in PBS (hereinafter referred to simply as the fluorescent solution). The film was then crushed with a mixer, followed by sonication, and further sizing into nano-order capsules using a 100 nm pore size filter. The state of the capsules was observed by conventional optical microscopy and polarized light microscopy, and it was found that the carrier encapsulated the fluorescent dye under the microscope and that there was maltase cross polarization under polarized light microscopy. We confirmed that the carrier contained the fluorescent dye under the microscope and that maltase cross polarization was present under the polarized light microscope. After 6 months of storage at 40° C. and 80% humidity, the state of the carrier was observed using a conventional optical microscope and a polarizing microscope. It was confirmed that the carrier did not break down and still contained the fluorescent dye under the microscope as it did at the start of the test, and that maltase cross polarization was present under the polarizing microscope. Table 7 shows the modified chain materials that are particularly useful for the present invention. These materials were those that were able to suppress the decay rate of the vitamin derivatives to less than 10% and maintain the stability of the vitamin derivatives. Those that could not be confirmed in either case were excluded from the table as having stability problems.

(Stability Test of Inclusion Active Ingredient)

The stability of The delivery carrier into cell was tested in different inclusion active ingredients. The carrier was prepared by dissolving 1 g of egg yolk-derived phosphatidylcholine, 0.8 g of dioleoylphosphatidylethanolamine, 3 g of DOPEMP (NIPAA/DMAPAA) Cop. 3 g, 0.05 g of cholesterol, and 0.1 g of GOVC (2-glyceryl-3-caprylate ascorbic acid, a vitamin derivative) in 200 mL chloroform. (2-glyceryl-3-caprylic acid ascorbic acid) were dissolved in 200 mL chloroform, and the solvent was removed by evaporator to form a lamellar film. To this, 0.5 g of different active ingredients and 1 mL of a peptide-linked fluorescent substance solution (a mixture of ovoalbumin:fluorescein isothiocyanate=1:1 (equimolar)) dissolved in PBS at a concentration of 0.2 mg/mL were mixed with 1 mL of the solution diluted in PBS (hereinafter referred to simply as the fluorescent solution). The film was then crushed with a mixer, followed by sonication, and further sizing into nano-order capsules using a 100 nm pore size filter. The state of the capsules was observed by conventional optical microscopy and polarized light microscopy, and it was found that the carrier encapsulated the fluorescent dye under the microscope and that there was maltase cross polarization under polarized light microscopy. We confirmed that the carrier contained the fluorescent dye under the microscope and that maltase cross polarization was present under the polarized light microscope. After 6 months of storage at 40° C. and 80% humidity, the state of the carrier was observed using a conventional optical microscope and a polarizing microscope. It was confirmed that the carrier did not break down and still contained the fluorescent dye under the microscope as it did at the start of the test, and that maltase cross polarization was present under the polarizing microscope. Table 8 lists the inclusion active ingredients that are particularly useful in the present invention as those in which the attenuation rate of the vitamin derivative was suppressed to 10% or less and the vitamin derivative was maintained stably. Those that could not be confirmed stability in either of the stability tests were excluded from the table as having stability problems.

Stability Test of the Active Ingredient in the Inclusion

We asked dermatologists and plastic surgeons to conduct efficacy tests on The delivery carrier into cell s of the invention containing different active ingredients prepared above, and several efficacy results were confirmed, and their specific effects are shown in Table 9.

INDUSTRIAL APPLICABILITY

The delivery carrier into the cell of the present invention are applicable to all living cell such as animal cell, plant cell, yeast, bacteria, fungi, mucus, mycoplasma, amoeba, etc., and can be selected from pharmaceuticals, quasi-drugs, cosmetics, supplements, veterinary drugs, fertilizers, pesticides, culture media, sundries, etc., and can be used for all products that are useful for increasing cell delivery efficiency. It can be applied to topical, oral, suppository, oral, drink, poultice, pack, spray, injection, dressing, liquid, ointment, aerosol, powder, mold, cream, topical dispersant, dispersant, granule, tablet, soft capsule, round, plate, troche and paste.

BRIEF DESCRIPTION OF THE DRAWINGS

FIG. 1) This figure shows the effect of the Delivery carrier into cell. In FIG. 1, (5) represents the cell membrane, the upper side of (5) is extracellular, and the lower side of (5) is intracellular. (1) is a stimuli-responsive polymer-containing molecule bound to The delivery carrier into cell of the present invention. The active ingredient is shown in (2) and is conjugated in the Delivery carrier into cell. (1) contains a long tail-like structure, which represents the stimuli-responsive polymer, bound to the membrane of The delivery carrier into cell by a surfactant lipid (ellipse). (3) is a simultaneous activator of autophagy-related genes and cathepsin synthesis genes, such as a vitamin derivative, which is also connected to the membrane of The delivery carrier into cell due to its amphiphilic nature. In A, it is a delivery carrier into cell bound to a vitamin receptor (indicated by a square and a circle with the top missing) that penetrates the cell membrane (5). It is a Delivery carrier into cell. In this way, the vitamin derivative (3) binds to the vitamin receptor on the surface of the cell membrane. However, because the molecular shape is different from that of the original vitamin, the vitamin is not transported through the vitamin transport channel, and a part of the cell membrane is depressed to form a pouch B). C) The endosomal carrier becomes hydrophobic due to the contraction of the stimuli-responsive polymer on the cell surface by external stimuli such as temperature and light. The parallelism of the membranes collapses and the membrane of The delivery carrier into cell is easily destroyed, releasing the active ingredient into the endosome. On the other hand, (6) is a lysosome with digestive enzymes (small squares). D) The lysosome fuses with the endosome and transfers the digestive enzymes to the endosome. D) The lysosome fuses with the endosome and transfers digestive enzymes to the endosome, where they degrade (digest) the molecules in the endosome E). F) Finally, the endosome is destroyed and the vitamin derivative is converted into a vitamin that can be used by the cell. F) Eventually, the endosome is destroyed and the active ingredient (black ▲), vitamin (oval), and undigested vitamin derivative (7) are released into the cell. The undigested vitamin derivatives further activate the autophagy system and are digested by autophagosomes and finally converted into vitamins for use by the cells. In this way, they can be used by cells.

FIG. 2) Typical structure of a lipid bilayer membrane of The delivery carrier into cell of the present invention. The delivery carrier into cell can also be a lipid bilayer membrane, in which case the membrane structure shown at the top (outermost) of the figure can be used. The lipids of the outermost membrane molecules can bind to the lipids of the inner membrane molecules to form a bilayer structure. The outer membrane consists of stimuli-responsive polymer-containing molecules (1), simultaneous activators of autophagy-related genes and cathepsin synthesis genes such as vitamin derivatives (2), and lipids (3). These three elements (1), (2), and (3) constitute the membrane molecule of The delivery carrier into cell of the present invention. (1), a stimuli-responsive polymer, consists of a long tail-like structure and the lipid to which it is attached (gray rectangle), and the lipid portion is embedded in the membrane molecule of The delivery carrier into cell. (2) is an amphiphilic substance, such as a vitamin derivative, whose lipids (hexagons) are embedded in the membrane molecules of The delivery carrier into cell. (3) shows two typical molecules that make up the membrane of a delivery carrier into cell, comprising a lipid (hexagonal) and an amphiphilic substance (rectangular and circular combined) that forms an emulsion membrane. The circular part represents water-soluble molecules, which allow The delivery carrier into cell s to be dispersed and suspended in water-soluble solvents and extracellular fluids. The inner membrane molecules consist mainly of (2) and (3). In the present invention, these bilayers can be further continued inward to form a multilayer membrane structure (lamellar structure). FIG. 3) Typical structure of the lipid bilayer of The delivery carrier into cell of the present invention. The delivery carrier into cell can also be a lipid bilayer membrane, in which case the membrane structure shown at the top (outermost) of this figure can be used. The lipids of the outermost membrane molecules can bind to the lipids of the inner membrane molecules to form a bilayer structure. In the outermost membrane molecule, the stimuli-responsive polymer-containing molecule (1) is ionically bound (black dotted line) to the water-soluble molecule portion (circular) of the lipid (2). The lipid in (2) has a structure in which water-soluble molecules (circular) and liposoluble molecules (hexagonal) are bound, but the membrane can also contain molecules consisting only of liposoluble molecules (hexagonal). (3) is a substance that simultaneously activates autophagy-related genes and cathepsin synthesis genes, such as an amphiphilic vitamin derivative. (3) also has a structure in which a water-soluble molecule (water droplet-shaped part) and a liposoluble molecule (hexagonal part) are combined, and the liposoluble part is fused with the lipid of the membrane. In the present invention, these bilayers can be further continued inward to form a multilayer membrane structure (lamellar structure).

The invention claimed is:

1. A delivery carrier into cell comprising a mixture of one or more substances selected from each of the following three groups: substances that simultaneously activate autophagy-related genes and cathepsin synthesis genes, stimuli-responsive polymer-containing molecules, and lipids, wherein the simultaneous activator of the autophagy-related gene and the cathepsin synthesis gene is Caprylyl 2-glyceryl ascorbic acid or Caprylyl 3-glyceryl ascorbic acid, wherein the delivery carrier into cell has either a monolamellar structure or a polylamellar structure, and wherein the stimuli-responsive polymer-containing molecule contains a stimuli-responsive molecule that is responsive to one or more of the following three conditions: temperature, pH, and light.

2. The delivery carrier into cell of claim 1, wherein some or all of the lipid is a surfactant that forms lamellae.

3. The delivery carrier into cell of claim 1, wherein the autophagy-related gene and the cathepsin synthesis gene are genes registered with the Human Genome Nomenclature Committee of the Organization for Human Genetic Analysis selected from the group consisting of: Autophagy-related genes ULK1, ULK2, ATG2A, ATG2B, ATG3, ATG4A, ATG4B, ATG4C, ATG4D, ATG5, BECN1, ATG7, GABARAP, GABARAPL1, GABARAPL2, MAP1LC3A, MAP1LC3B, MAP1LC3B2, MAP1LC3C, ATG9A, ATG9B, ATG10, ATG12, ATG13, ATG14, ATG16L1, ATG16L2, RB1CC1, WIPI1, WIPI2, SNX30, SNX4, ATG101, and AMBRA1, and Cathepsin synthesis genes CTSA, CTSB, CTSC, CTSD, CTSD, CTSE, CTSF, CTSG, CTSH, CTSK, CTSL, CTSLP6, CTSO, CTSS, CTSV, CTSW, and CTSZ.

4. The delivery carrier into cell according to claim 1, wherein the molecule containing the stimuli-responsive polymer has a linear or branched polymer structure comprising one or more temperature, pH, and light-stimulating substances selected from the group consisting of: temperature-stimulus-responsive substances (Polyoxyethylene octylphenyl ether) acrylate, (Polyoxyethylene octylphenyl ether) methacrylate, (Polyoxyethylene nonylphenyl ether) acrylate, (Polyoxyethylene nonylphenyl ether) methacrylate (Polyoxyethylene lauryl ether) acrylate, (Polyoxyethylene lauryl ether) methacrylate, 1,2,4,5-tetrakis(1,2,4,5-tetrakis (N,N-dithiocarbamylmethyl)benzene, 1,3,5-tri(bromomethyl)benzene, 2-n-propyl-2-oxazoline, 2 N,N-dimethylaminoethyl acrylate, 2-N,N-dimethylaminoethyl methacrylate DMAEMA, 2-Amino-2-hydroxymethyl-1-hydroxymethyl-1-acrylate-2-hydroxymethyl-1,3-propanediol, 2 2-Amino-2-hydroxymethyl-1,3-propanediol (Tris), 2-Amino-2-hydroxymethyl-1,3-propanediol 2-Amino-2-hydroxymethyl-1,3-propanediol hydrochloride, 2-hydroxy-3-phenoxypropyl acrylate hydroxybutyl acrylate, 2-hydroxybutyl methacrylate, 2-hydroxypropyl acrylate, 2-hydroxypropyl methacrylate hydroxypropyl methacrylate, 3,5-tri(N,N-dithiocarbamylmethyl)benzene, 3-N,N-dimethylaminopropyl acrylamide, N-acryloyl aspartamide, N-acryloyl glycinamide, N-acryloyl glutamamide, N-acryloyl asparagamide N-methylacryloylaspartamide, N,N-dimethylmethacrylamide, N,N-dimethylacrylamide, N,N-methylenebisacrylamide N-methylenebisacrylamide, N,N-ethylmethylacrylamide, N,N-ethyl methylamide, N,N-ethyl methyl methacrylamide, N,N-dialkyl Dithiocarbamylmethyl, N,N-Dialkyl-Substituted Acrylamide Derivatives, N,N-Dialkyl-Substituted Methacrylamide Derivatives, N,N-Diethylacrylamide, N,N-Diethylamide, N,N-Diethylmethacrylamide N,N-Diethylmethacrylamide, N,N-Diethylamide, N,N-Diethylmethacrylamide, N,N-Diethylmethacrylamide, Sodium N,N-Dithiocarbamate-dithiocarbamate), N,N-dimethylacrylamide, N,N-dimethylmethacrylamide, N, N-propylacrylamide, N, N-propylmethacrylamide, N N-acryloyl piperidine, N-acryloyl morpholine, N-alkyl acrylamide, N-alkyl methacrylamide, N-acryloyl piperidine, N-acryloyl morpholine N-alkyl methacrylamide, N-alkyl substituted acrylamide, N-alkyl substituted methacrylamide N-alkyl methacrylamide, N-alkyl substituted acrylamide, N-alkyl substituted methacrylamide N-alkyl-substituted methacrylamide, N-allenylphthalimide, N-isopropylacrylamide, N-isopropylamide N-ethylethyl acrylamide, N-ethyl methacrylamide, N-ethoxyethyl acrylamide, N-ethoxyethyl amide, N-ethoxyethyl methacrylamide, N-cyclopropylacrylamide, N-cyclopropylamide, N-cyclopropylmethacrylamide, N-tetrahydrofurfurylacrylamide, N-cyclopropylamide, N-cyclopropylmethacrylamide tetrahydrofurfurylmethacrylamide, N-biotinyl-N'-methacloyltrimethylenamide, N-vinylacrylamide, N-vinylalkylacrylamide, N-vinylmethacrylamide, N-propylacrylamide, N-methacryloyl piperidine, N- or N,N-dialkyl-substituted methacrylamide derivatives, s-butylacrylamide, t-butylacrylamide, acroylglycinamide, acroylzarkosinamide, acroylnipecotamide, acroylmethyluracil, Acetyl Acrylamide, Ethyl Isopropyl Acrylamide, Ethylene Glycol/Propylene Glycol Copolymer, Ethylene Glycol Arenyl Methyl Ether, Oxyethylene Acrylate Derivatives, Oxyethylene Sorbitan Laureate, Oxyethylene Methacrylate Ester Derivatives, Oxyethylene Laurylamine, Acrylates with Oligoethylene Glycol Side Chains, Diisopropylacrylamide, Diethylacrylamide, Diethylaminoacrylate, Diethylaminomethacrylate, Diethylene Glycol Allenyl Methyl Ether, Dibutylacrylamide, Dipropylacrylamide, Dimethylacrylamide, Dimethylaminoacrylamide, Dimethylaminoacrylate, Dimethylaminopropylacrylamide, Dimethylaminopropylmethacrylamide, Dimethylaminomethacrylamide, Dimethylaminomethacrylate, Sodium N,N-dithiocarbamate, Hexakis(N,N-dithiocarbamylmethyl) Benzene, Hexakis (bromomethyl)benzene, Methylacrylamide/N-acetylacrylamide copolymers, and their salts of Na, Mg, K, Al, Zn, Ca, triethanolamine and their derivatives; pH stimulus-responsive substances Glucosamine, chitosan, 2-ethoxyethyl vinyl ether, N-alkylacrylamide/polyacrylic acid, N-vinylalkylacrylamide, 4-(2-vinyloxyethoxy) benzoic acid, 6-(2-vinyloxyethoxy) hexanoic acid, 6-(Vinyloxy) hexanoic acid, isobutyl vinyl ether, their alkali metal salts and their derivatives, their Na, Mg, K, Al, Zn, Ca, triethanolamine salts and their derivatives; and Light stimuli-responsive substances N-alkylacrylamide, n-(4-phenylazophenyl) acrylamide, 6-[4-(4-pyridylazo) phenoxy]hexamethacrylate, N-vinylalkylacrylamide, 4-[2-(vinyloxy) ethoxy]azobenzene, 2-(2-Ethoxy) ethoxyethyl vinyl ether, salts of these Na, Mg, K, Al, Zn, Ca, triethanolamine and their derivatives.

5. The delivery carrier into the cell of claim 1, wherein the application of the delivery carrier is one type selected from pharmaceuticals, quasi-drugs, cosmetics, supplements, and veterinary drugs.

* * * * *